United States Patent
Matsumura

(10) Patent No.: US 8,168,263 B2
(45) Date of Patent: May 1, 2012

(54) PHOTO-CURABLE COMPOSITION, INK COMPOSITION, AND INKJET RECORDING METHOD USING THE INK COMPOSITION

(75) Inventor: Tokihiko Matsumura, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 517 days.

(21) Appl. No.: 12/496,661

(22) Filed: Jul. 2, 2009

(65) Prior Publication Data
US 2010/0013899 A1   Jan. 21, 2010

(30) Foreign Application Priority Data

Jul. 16, 2008  (JP) ................... 2008-185205

(51) Int. Cl.
*C09D 11/00* (2006.01)
*B05D 1/32* (2006.01)

(52) U.S. Cl. ............. 427/466; 522/25; 522/53; 522/63; 522/75

(58) Field of Classification Search .............. 427/466; 522/25, 31, 53, 63, 75, 168, 170, 172
See application file for complete search history.

(56) References Cited

U.S. PATENT DOCUMENTS

| | | | | |
|---|---|---|---|---|
| 4,134,813 A | * | 1/1979 | Kuesters et al. | 522/14 |
| 4,315,807 A | * | 2/1982 | Felder et al. | 522/33 |
| 6,287,749 B1 | * | 9/2001 | Nagarajan et al. | 430/281.1 |
| 7,858,670 B2 | * | 12/2010 | Akiyama et al. | 522/83 |
| 7,985,785 B2 | * | 7/2011 | Matsumura et al. | 523/160 |
| 2005/0146544 A1 | * | 7/2005 | Kondo | 347/7 |
| 2008/0239045 A1 | * | 10/2008 | Umebayashi et al. | 347/102 |
| 2009/0087575 A1 | * | 4/2009 | Matsumura et al. | 427/487 |
| 2009/0186163 A1 | * | 7/2009 | Umebayashi et al. | 427/511 |
| 2010/0015352 A1 | * | 1/2010 | Matsumura | 427/511 |

FOREIGN PATENT DOCUMENTS

| | | |
|---|---|---|
| EP | 1876211 A | 1/2008 |
| EP | 1944173 A | 7/2008 |
| EP | 2085439 A | 8/2009 |
| JP | 11-199681 | 7/1999 |
| JP | 11-263804 | 9/1999 |
| JP | 3437069 | 8/2003 |

OTHER PUBLICATIONS

Corresponding EPO Search Report, Oct. 30, 2009.

\* cited by examiner

*Primary Examiner* — Susan W Berman

(74) *Attorney, Agent, or Firm* — SOLARIS Intellectual Property Group, PLLC

(57) ABSTRACT

A photo-curable composition including (A) a cationic polymerizable compound, (B) a sensitizing colorant represented by the following formula (I), and (C) an onium salt; an ink composition containing the photo-curable composition; an inkjet recording method using the ink composition are provided, and in formula (I), X represents O, S or NR, R represents a hydrogen atom, an alkyl group, or an acyl group, n represents 0 or 1, each of $R^1$ to $R^8$ independently represents a hydrogen atom, or a monovalent substituent.

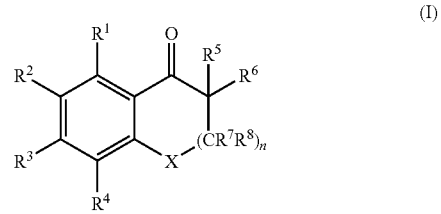

(I)

7 Claims, No Drawings

PHOTO-CURABLE COMPOSITION, INK COMPOSITION, AND INKJET RECORDING METHOD USING THE INK COMPOSITION

CROSS-REFERENCE TO RELATED APPLICATION

This application claims priority under 35 USC 119 from Japanese Patent Application No. 2008-185205 filed on Jul. 16, 2008, the disclosure of which is incorporated by reference herein.

BACKGROUND OF THE INVENTION

1. Field of the Invention

The present invention relates to a photo-curable composition, an ink composition primarily suitable for inkjet recording, and an inkjet recording method using the ink composition.

2. Related Art

As methods of recording images on a recording medium, such as paper, based on an image data signal, an electrophotographic method, sublimation and melting thermal transfer methods, and an inkjet recording method are known. The electrophotographic method requires processes of charging on a photoreceptor drum and exposure to form an electrostatic latent image, and therefore the system is complicated and manufacturing costs are high. With thermal transfer methods, although apparatuses are inexpensive, there are problems such that running costs are high and waste is generated since ink ribbons are used. On the other hand, the inkjet recording method is advantageous because recording apparatuses are inexpensive, and an image is directly formed on a recording medium by ejecting inks only on necessary image parts, so that ink can be efficiently used and running costs are inexpensive. Further, the inkjet recording method produces little noise, and is therefore excellent as an image recording method.

Ink compositions curable by irradiation with radiation such as UV rays, in particular, inkjet recording inks (radiation-curable inkjet recording inks), are required to have sufficiently high sensitivity and to be capable of producing high quality images. High sensitivity imparts various advantages such as high curability by radiation, a reduction in consumed electricity, an increase in the life of a radiation generator due to the reduction of a load on a radiation generator, and prevention of generation of a low molecular weight substance due to insufficient curing. When ink compositions, in particular, inkjet recording inks, are used as the image part of a planographic printing plate, the curing strength of the image part is heightened by high sensitivity and high printing durability can be obtained, and for these reasons they are preferable.

The acids of onium compounds, radical polymerization initiators, and cationic polymerization initiators are sparingly absorptive in wavelengths of 360 nm or greater, and thus curing properties conspicuously worsen when exposure is performed with light source having a wavelength longer than this. In particular, since conventional photo-polymerization initiators such as sulfonium salts and iodonium salts are sparingly absorptive of UV rays on the long wavelength side, curing properties worsen upon forming a thick curing film. Further, photo-curable compositions containing a large amount of white pigment, such as titanium oxide, and having absorption in UV region, have many problems of implementation.

To address these problems, sensitizers (sensitizing dyestuffs) have been examined. For example, as sensitizers of a diaryl iodonium salt photo-polymerization initiator, various dye derivatives have been reported to be effective, and thioxanthone derivatives are known in particular as inexpensive and general sensitizers (for example, refer to Japanese Patent Application Laid-Open (JP-A) No. 11-263804. However, thioxanthone derivatives alone are insufficient for photo-curing a photo-curable composition that uses additives such as a pigment or the like. Photo-curable compositions using anthracene compounds (refer to JP-A No. 11-199681) or 9,10-dialkoxyanthracene derivatives (for example, Japanese Patent No. 3437069) have also been examined as sensitizers. However, since these anthracene compounds and thioxanthone compounds are absorptive up to a long wavelength region, there is a problem that photo-curable compositions and cured products thereof tend to be yellowed.

It can be seen from the above that there is a desire for photo-curable compositions curable with high sensitivity by irradiation with actinic radiation, capable of forming a cured film excellent in adhesion to the surface of a solid such as a recording medium, and, when used with ink compositions, capable of restraining coloration of compositions.

SUMMARY OF THE INVENTION

The present invention has been made in view of the above circumstances and provides a photo-curable composition, an ink composition, and an inkjet recording method using the ink composition.

A first aspect of the invention provides a photo-curable composition containing:
(A) a cationic polymerizable compound,
(B) a sensitizing colorant represented by the following formula (I), and
(C) an onium salt:

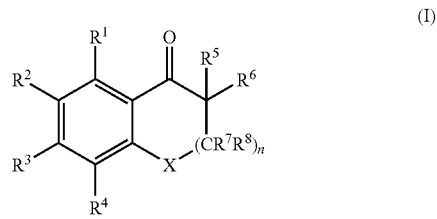

in formula (I), X represents O, S or NR; R represents a hydrogen atom, an alkyl group, or an acyl group; n represents 0 or 1; each of $R^1$ to $R^8$ independently represents a hydrogen atom, or a monovalent substituent, contiguous two of $R^1$, $R^2$, $R^3$ and $R^4$ may be linked to each other to form a ring, and $R^5$ and $R^6$, or $R^7$ and $R^8$ may be linked to each other to form an aliphatic ring, but they do not form an aromatic ring.

DETAILED DESCRIPTION OF THE INVENTION

As a result of earnest study, the present inventors have found that the above problems can be solved by the use of a specific sensitizing colorant and an onium salt in combination. Thus, the photo-curable composition of the invention, the ink composition containing the photo-curable composition, and the inkjet recording method using the ink composition have been accomplished.

The ink composition of the invention contains the photo-curable composition of the invention, and the ink composition is preferably used for inkjet recording.

The inkjet recording method in the invention includes (a) a process of ejecting the ink composition of the invention on a medium to be recorded, and (b) a process of irradiating the ejected ink composition with actinic radiation to cure the ink composition.

Further, in the inkjet recording method in the invention, the actinic radiation is preferably ultraviolet ray emitted from a light emitting diode emitting ultraviolet ray having light emission peak in the range of wavelengths of 340 to 370 nm, and maximum intensity of illumination on the surface of a medium to be recorded of 10 to 2,000 mW/cm$^2$.

The functions of the invention are not clearly known but presumably as follows.

Since sensitizing colorant (B) for use in the invention efficiently absorbs radiation, especially light of 365 nm, and is excited and electron-transfers to onium salt (C), it is presumed that sensitizing colorant (B) can accelerate decomposition of onium salt (C). Accordingly, by the combination of these components, conventionally used polymerization, crosslinking, decomposition, color developing reaction, and radical reaction using the acid generated by irradiation of radiation as catalyst can be swiftly and surely progressed. Since in addition to components (B) and (C), cationic polymerizable compound (A) is used in the invention, it becomes possible to increase sensitivity to radiations of various uses. It is also presumed that since polymerization and curing reaction sufficiently advance, a cured film having high adhesion to the surface of a solid can be formed.

[Photo-curable Composition]

The photo-curable composition in the invention contains (A) a cationic polymerizable compound, (B) a sensitizing colorant represented by the following formula (I), and (C) an onium salt.

The essential components constituting the photo-curable composition of the invention will be described below.

<Cationic Polymerizable Compound (A)>

The photo-curable composition in the invention contains cationic polymerizable compound (A).

Cationic polymerizable compounds (A) for use in the invention are not especially restricted so long as they are compounds capable of causing polymerization reaction and curing by the acid generated from the later-described onium salt (C), and various cationic polymerizable monomers known as photo-cationic polymerizable monomers can be used.

As the cationic polymerizable monomers, for example, epoxy compounds, vinyl ether compounds, and oxetane compounds as disclosed in JP-A Nos. 6-9714, 2001-31892, 2001-40068, 2001-55507, 2001-310938, 2001-310937 and 2001-220526 are exemplified.

Further, as cationic polymerizable compounds, cationic polymer-series photo-curable resins are also known and photo-cationic polymer-series photo-curable resins having been sensitized in visible light wavelength region of 400 nm or more are disclosed in JP-A Nos. 6-43633 and 8-324137 lately.

As the epoxy compounds, aromatic epoxide, alicyclic epoxide, and aliphatic epoxide are exemplified.

As the aromatic epoxide, di- or polyglycidyl ether manufactured by the reaction of polyhydric phenol having at least one aromatic nucleus or alkylene oxide adduct thereof and epichlorohydrin is exemplified. For example, di- or polyglycidyl ether of bisphenol A or alkylene oxide adduct thereof, di- or polyglycidyl ether of hydrogenated bisphenol A or alkylene oxide adduct thereof, and novolak type epoxy resins are exemplified. As the alkylene oxides, ethylene oxide and propylene oxide are exemplified.

As the alicyclic epoxides, cyclohexene oxide or cyclopentene oxidel-containing compounds obtained by epoxydation of compounds having at least one cycloalkane ring such as cyclohexene or cyclopentene ring with an appropriate oxidant such as hydrogen peroxide or peracid are preferably exemplified.

As the aliphatic epoxides, di- or polyglycidyl ethers of aliphatic polyhydric alcohols or alkylene oxide adducts thereof are exemplified. As the representative examples of the aliphatic epoxides, diglycidyl ethers of alkylene glycol such as diglycidyl ether of ethylene glycol, diglycidyl ether of propylene glycol, and diglycidyl ether of 1,6-hexanediol; and diglycidyl ethers of polyalkylene glycol represented by polyglycidyl ether of polyhydric alcohol such as di- or triglycidyl ether of glycerin or alkylene oxide adduct thereof, diglycidyl ether of polyethylene glycol or alkylene oxide adduct thereof, and diglycidyl ether of polypropylene glycol or alkylene oxide adduct thereof are exemplified. As the alkylene oxides, ethylene oxide and propylene oxide are exemplified.

Monofunctional and polyfunctional epoxy compounds for use in the invention will be described in detail below.

As the monofunctional epoxy compounds, e.g., phenyl glycidyl ether, p-tert-butylphenyl glycidyl ether, butyl glycidyl ether, 2-ethylhexyl glycidyl ether, allyl glycidyl ether, 1,2-butylene oxide, 1,3-butadiene monoxide, 1,2-epoxydodecane, epichlorohydrin, 1,2-epoxydecane, styrene oxide, cyclohexene oxide, 3-methacryloyloxymethylcyclohexene oxide, 3-acryloyloxymethylcyclohexene oxide, and 3-vinylcyclohexene oxide are exemplified.

As the polyfunctional epoxy compounds, e.g., bisphenol A diglycidyl ether, bisphenol F diglycidyl ether, bisphenol S diglycidyl ether, brominated bisphenol A diglycidyl ether, brominated bisphenol F diglycidyl ether, brominated bisphenol S diglycidyl ether, epoxy novolak resin, hydrogenated bisphenol A diglycidyl ether, hydrogenated bisphenol F diglycidyl ether, hydrogenated bisphenol S diglycidyl ether, 3,4-epoxycyclohexylmethyl-3',4'-epoxycyclohexane carboxylate, bis(3,4-epoxy-6-methylcyclohexylmethyl)adipate, 3,4-epoxy-6-methylcyclohexyl-3',4'-epoxy-6'-methylcyclohexane carboxylate, methylenebis(3,4-epoxycyclohexane), dicyclopentadiene diepoxide, di(3,4-epoxycyclohexylmethyl)ether of ethylene glycol, ethylenebis(3,4-epoxycyclohexane carboxylate), dioctyl epoxyhexahydrophthalate, di-2-ethylhexyl epoxyhexahydrophthalate, 1,4-butanediol diglycidyl ether, 1,6-hexanediol diglycidyl ether, glycerin triglycidyl ether, trimethylolpropane triglycidyl ether, polyethylene glycol diglycidyl ether, polypropylene glycol diglycidyl ethers, 1,13-tetradecadiene dioxide, limonene dioxide, 1,2,7,8-diepoxyoctane, and 1,2,5,6-diepoxycyclooctane are exemplified.

Of these epoxy compounds, aromatic epoxides and alicyclic epoxides are preferred from the point of being excellent in curing rate, and alicyclic epoxides are especially preferred.

As the vinyl ether compounds, di- or trivinyl ether compounds, e.g., ethylene glycol divinyl ether, diethylene glycol divinyl ether, triethylene glycol divinyl ether, propylene glycol divinyl ether, dipropylene glycol divinyl ether, butanediol divinyl ether, hexanediol divinyl ether, cyclohexanedimethanol divinyl ether, and trimethylolpropane trivinyl ether; and monovinyl ether compounds, e.g., ethyl vinyl ether, n-butyl vinyl ether, isobutyl vinyl ether, octadecyl vinyl ether, cyclohexyl vinyl ether, hydroxybutyl vinyl ether, 2-ethylhexyl vinyl ether, cyclohexanedimethanol monovinyl ether, n-propyl vinyl ether, isopropyl vinyl ether, dodecyl vinyl ether, diethylene glycol monovinyl ether, and octadecyl vinyl ether are exemplified.

Monofunctional vinyl ethers and polyfunctional vinyl ethers are described in detail below.

The examples of monofunctional vinyl ethers include methyl vinyl ether, ethyl vinyl ether, propyl vinyl ether, n-butyl vinyl ether, t-butyl vinyl ether, 2-ethylhexyl vinyl ether, n-nonyl vinyl ether, lauryl vinyl ether, cyclohexyl vinyl ether, cyclohexylmethyl vinyl ether, 4-methylcyclohexylmethyl vinyl ether, benzyl vinyl ether, dicyclopentenyl vinyl ether, 2-dicyclopentenoxyethyl vinyl ether, methoxyethyl vinyl ether, ethoxyethyl vinyl ether, butoxyethyl vinyl ether, methoxyethoxyethyl vinyl ether, ethoxyethoxyethyl vinyl ether, methoxypolyethylene glycol vinyl ether, tetrahydrofurfuryl vinyl ether, 2-hydroxyethyl vinyl ether, 2-hydroxypropyl vinyl ether, 4-hydroxybutyl vinyl ether, 4-hydroxymethylcyclohexylmethyl vinyl ether, diethylene glycol monovinyl ether, polyethylene glycol vinyl ether, chloroethyl vinyl ether, chlorobutyl vinyl ether, chloroethoxyethyl vinyl ether, phenylethyl vinyl ether, and phenoxypolyethylene glycol vinyl ether.

As polyfunctional vinyl ethers, divinyl ethers, e.g., ethylene glycol divinyl ether, diethylene glycol divinyl ether, polyethylene glycol divinyl ether, propylene glycol divinyl ether, butylenes glycol divinyl ether, hexanediol divinyl ether, bisphenol A alkylene oxide divinyl ether, and bisphenol F alkylene oxide divinyl ether; polyfunctional vinyl ethers, e.g., trimethylolethane trivinyl ether, trimethylolpropane trivinyl ether, ditrimethylolpropane tetravinyl ether, glycerin trivinyl ether, pentaerythritol tetravinyl ether, dipentaerythritol pentavinyl ether, dipentaerythritol hexavinyl ether, ethylene oxide addition trimethylolpropane trivinyl ether, propylene oxide addition trimethylolpropane trivinyl ether, ethylene oxide addition ditrimethylolpropane tetravinyl ether, propylene oxide addition ditrimethylolpropane tetravinyl ether, ethylene oxide addition pentaerythritol tetravinyl ether, propylene oxide addition pentaerythritol tetravinyl ether, ethylene oxide addition dipentaerythritol hexavinyl ether, and propylene oxide addition dipentaerythritol hexavinyl ether are exemplified.

As the vinyl ether compounds, di- or trivinyl ether compounds are preferred from the viewpoint of a curing property, adhesion to the solid surface of a cured product, and the surface hardness of a cured product, and divinyl ether compounds are especially preferred.

The oxetane compound in the invention means a compound having an oxetane ring, and known oxetane compounds as disclosed in JP-A Nos. 2001-220526, 2001-310937 and 2003-341217 can be arbitrarily selectively used.

The compounds having an oxetane ring that can be used in the photo-curable composition in the invention are preferably compounds having 1 to 4 oxetane rings in the structure are preferred. By the use of such compounds, the viscosity of the photo-curable composition can be easily maintained in a good handling range, and also a high adhesion property to the solid surface of a photo-curable composition after curing (a cured product) can be obtained.

As the compounds having 1 or 2 oxetane rings in the molecule, the compounds represented by any of the following formulae (1) to (3) are exemplified.

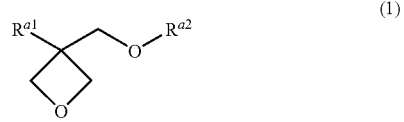
(1)

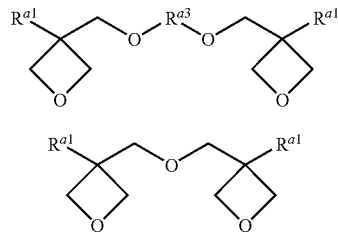
(2)

(3)

In the above formulae, $R^{a1}$ represents a hydrogen atom, an alkyl group having 1 to 6 carbon atoms, a fluoroalkyl group having 1 to 6 carbon atoms, an allyl group, an aryl group, a furyl group, or a thienyl group. When two $R^{a1}$ are present in the molecule, they may be the same with or different from each other.

As the examples of the alkyl groups, a methyl group, an ethyl group, a propyl group, and a butyl group are exemplified. As the fluoroalkyl groups, any hydrogen atom of these alkyl groups are substituted with a fluorine atom are exemplified.

$R^{a2}$ represents a hydrogen atom, an alkyl group having 1 to 6 carbon atoms, an alkenyl group having 2 to 6 carbon atoms, a group having an aromatic ring, an alkylcarbonyl group having 2 to 6 carbon atoms, an alkoxycarbonyl group having 2 to 6 carbon atoms, or an N-alkylcarbamoyl group having 2 to 6 carbon atoms. As the examples of the alkyl groups, a methyl group, an ethyl group, a propyl group, and a butyl group are exemplified. As the examples of the alkenyl groups, a 1-propenyl group, a 2-propenyl group, a 2-methyl-1-propenyl group, a 2-methyl-2-propenyl group, a 1-butenyl group, a 2-butenyl group, and a 3-butenyl group are exemplified. As the groups having an aromatic ring, a phenyl group, a benzyl group, a fluorobenzyl group, a methoxybenzyl group, and a phenoxyethyl group; as the alkylcarbonyl groups, an ethylcarbonyl group, a propylcarbonyl group, and a butylcarbonyl group; as the alkoxycarbonyl groups, an ethoxycarbonyl group, a propoxycarbonyl group, and a butoxycarbonyl group; and as the N-alkylcarbamoyl groups, an ethylcarbamoyl group, a propylcarbamoyl group, a butylcarbamoyl group, and a pentylcarbamoyl group are exemplified, respectively.

$R^{a3}$ represents a linear or branched alkylene group, a linear or branched poly(alkyleneoxy) group, a linear or branched unsaturated hydrocarbon group, a carbonyl group or an alkylene group containing a carbonyl group, an alkylene group containing a carboxyl group, an alkylene group containing a carbamoyl group, or a group shown below. As the alkylene group, e.g., an ethylene group, a propylene group, or a butylene group is exemplified. As the poly(alkyleneoxy) group, a poly(ethyleneoxy) group or a poly(propyleneoxy) group is exemplified. As the unsaturated hydrocarbon group, a propenylene group, a methylpropenylene group, or a butenylene group is exemplified.

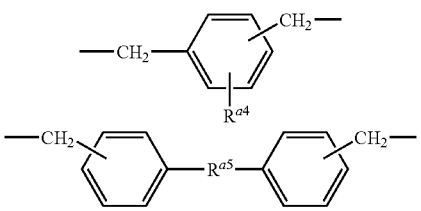

-continued

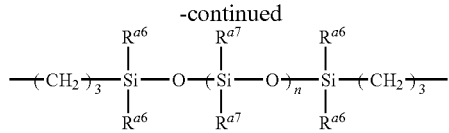

When $R^{a3}$ represents the above polyvalent group, $R^{a4}$ represents a hydrogen atom, an alkyl group having 1 to 4 carbon atoms, an alkoxy group having 1 to 4 carbon atoms, a halogen atom, a nitro group, a cyano group, a mercapto group, a lower alkylcarboxyl group, a carboxyl group, or a carbamoyl group.

$R^{a5}$ represents an oxygen atom, a sulfur atom, a methylene group, NH, SO, $SO_2$, $C(CF_3)_2$, or $C(CH_3)_2$.

$R^{a6}$ represents an alkyl group having 1 to 4 carbon atoms, or an aryl group; n represents an integer of 0 to 2,000.

$R^{a7}$ represents an alkyl group having 1 to 4 carbon atoms, an aryl group, or a monovalent group having the following structure.

In the following formula, $R^{a3}$ represents an alkyl group having 1 to 4 carbon atoms, or an aryl group; and m represents an integer of 0 to 100.

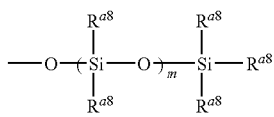

As the compound represented by formula (1), e.g., 3-ethyl-3-hydroxymethyl oxetane (OXT-101, manufactured by TOAGOSEI CO., LTD.), 3-ethyl-3-(2-ethylhexyloxy-methyl)oxetane (OXT-212, manufactured by TOAGOSEI CO., LTD.), 3-ethyl-3-phenoxy-methyl oxetane (OXT-211, manufactured by TOAGOSEI CO., LTD.) are exemplified.

As the compound represented by formula (2), e.g., 1,4-bis[(3-ethyl-3-oxetanylmethoxy)methyl]benzene (OXT-121, manufactured by TOAGOSEI CO., LTD.) is exemplified.

As the compound represented by formula (3), e.g., bis(3-ethyl-3-oxetanylmethyl)ether (OXT-221, manufactured by TOAGOSEI CO., LTD.) is exemplified.

As the compound having 3 or 4 oxetane rings, a compound represented by the following formula (4) is exemplified.

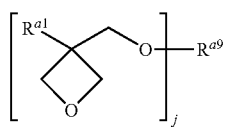

In formula (4), $R^{a1}$ has the same meaning as in formula (1). Further, as the polyvalent linking group $R^{a9}$, a branched alkylene group represented by any of the following formulae A to C having 1 to 12 carbon atoms, a branched poly(alkyleneoxy) group represented by the following formula D, and a branched polysiloxy group represented by the following formula E are exemplified. J is 3 or 4.

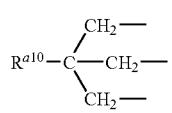

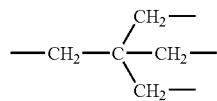

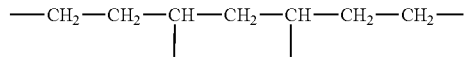

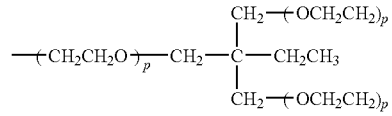

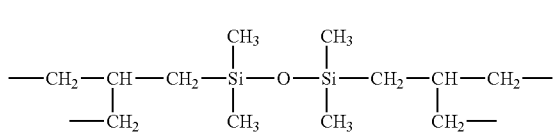

In formula A, $R^{a10}$ represents a methyl group, an ethyl group, or a propyl group. In formula D, p is an integer of 1 to 10.

As another embodiment of the oxetane compound preferably used in the invention, a compound having an oxetane ring in the side chain as represented by the following formula (5) is exemplified.

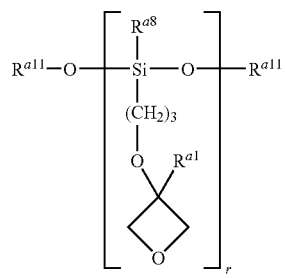

In formula (5), each of $R^{a1}$ and $R^{a8}$ has the same meanings as those in the above formula. $R^{a11}$ represents an alkyl group having 1 to 4 carbon atoms, e.g., a methyl group, an ethyl group, a propyl group, or a butyl group, or a trialkylsilyl group, and r is 1 to 4.

These compounds having an oxetane ring are disclosed in detail in JP-A No. 2003-341217, paragraphs [0021] to [0084], which can be preferably used in the invention. The oxetane compounds disclosed in JP-A No. 2004-91556, paragraphs [0022] to [0058] can also be used in the invention.

Of the oxetane compounds usable in the invention, it is preferred to use those having one oxetane ring in view of the viscosity and adhesion of the photo-curable composition.

These cationic polymerizable compounds may be used by one kind alone or two or more compounds may be used in combination in the photo-curable composition of the invention, but from the aspect of effectively restraining volume shrinkage of the photo-curable composition at the time of curing, it is preferred to use at least one compound selected from oxetane compounds and epoxy compounds in combination with a vinyl ether compound.

The content of cationic polymerizable compound (A) in the photo-curable composition of the invention is generally 10 to 95 mass % based on all the solids content of the composition, preferably 30 to 90 mass %, and more preferably 50 to 85 mass %.

<Sensitizing Colorant (B) Represented by Formula (I)>

For the acceleration of decomposition of a polymerization initiator on irradiation with actinic radiation, the photo-curable composition of the invention contains a sensitizing colorant. As the sensitizing colorant, a sensitizing colorant represented by the following formula (I) described in detail below (hereinafter, referred to as "specific sensitizing colorant") is contained as the essential component.

In general, a sensitizing colorant absorbs specific actinic radiation and becomes an electron excitation state. The sensitizing colorant in an electron excitation state comes into contact with a polymerization initiator to cause functions of electron transfer, energy transfer and heat generation, by which chemical changes of the polymerization initiator, that is, decomposition, and formation of active species, e.g., radical, acid, base, etc., are accelerated. The active seeds generated here cause and accelerate polymerization and curing reaction of the later-described polymerizable compounds.

As the sensitizing colorant, it is sufficient to use a compound corresponding to the wavelength of actinic radiation generating the initiating species in the polymerization initiator for use in the photo-curable composition, but considering to be used in the curing reaction of general photo-curable compositions, sensitizing colorants having absorption wavelengths in the region of 350 to 450 nm can be exemplified as preferred examples of sensitizing colorants.

The photo-curable composition in the invention requires containing a sensitizing colorant represented by the following formula (I) (specific sensitizing colorant).

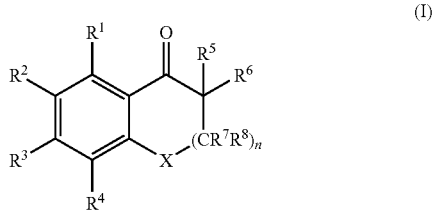

(I)

In formula (I), X represents O, S or NR; R represents a hydrogen atom, an alkyl group, or an acyl group; n represents 0 or 1; each of $R^1$, $R^2$, $R^3$, $R^4$, $R^5$, $R^6$, $R^7$ and $R^8$ independently represents a hydrogen atom, or a monovalent substituent, contiguous two of $R^1$, $R^2$, $R^3$ and $R^4$ may be linked to each other to form a ring, and $R^5$ or $R^6$ and $R^7$ or $R^8$ may be linked to each other to form an aliphatic ring, but they do not form an aromatic ring.

In formula (I), X preferably represents O or S, and more preferably S.

When n is 0, $(CR^7R^8)$ is not present, and the carbon atom bonding to $R^5$ and $R^6$ is directly bonded to X to come to form a 5-membered heterocyclic ring containing X.

Each of $R^1$, $R^2$, $R^3$, $R^4$, $R^5$, $R^6$, $R^7$ and $R^8$ independently represents a hydrogen atom or a monovalent substituent.

As the examples of the monovalent substituents when each of $R^1$, $R^2$, $R^3$, $R^4$, $R^5$, $R^6$, $R^7$ and $R^8$ represents a monovalent substituent, a halogen atom, an aliphatic group, an aromatic group, a heterocyclic group, a cyano group, a hydroxyl group, a nitro group, an amino group, an alkylamino group, an alkoxy group, an aryloxy group, an amido group, an arylamino group, a ureido group, a sulfamoylamino group, an alkylthio group, an arylthio group, an alkoxycarbonylamino group, a sulfonamide group, a carbamoyl group, a sulfamoyl group, a sulfonyl group, an alkoxycarbonyl group, a heterocyclic oxy group, an azo group, an acyloxy group, a carbamoyloxy group, a silyloxy group, an aryloxycarbonyl group, an aryloxycarbonylamino group, an imido group, a heterocyclic thio group, a sulfinyl group, a phosphoryl group, an acyl group, a carboxyl group, and a sulfo group are exemplified. Of these groups, an alkyl group, an alkoxy group and a halogen atom are preferred.

When each of $R^1$, $R^2$, $R^3$, $R^4$, $R^5$, $R^6$, $R^7$ and $R^8$ in formula (I) represents a monovalent substituent, as alkyl groups, alkyl groups having 1 to 10 carbon atoms are preferred, and alkyl groups having 1 to 4 carbon atoms, e.g., a methyl group, an ethyl group, a propyl group, an n-butyl group, a sec-butyl group, and a t-butyl group are more preferred.

Similarly as alkoxy groups, alkoxy groups having 1 to 4 carbon atoms, e.g., a methoxy group, an ethoxy group, a hydroxyethoxy group, a propoxy group, an n-butoxy group, an isobutoxy group, a sec-butoxy group, and a t-butoxy are preferably exemplified.

As halogen atoms, a fluorine atom, a chlorine atom, a bromine atom, and an iodine atom can be exemplified.

Contiguous two of $R^1$, $R^2$, $R^3$ and $R^4$ may be linked, e.g., condensed, to each other to form a ring.

As the ring structures to be formed, 5- or 6-membered aliphatic rings and aromatic rings are exemplified. These rings may be heterocyclic rings containing elements other than a carbon atom, and formed rings may further form a binuclear ring, e.g., a condensed ring by combination. These ring structures may further have substituents such as the substituents exemplified in the case where each of $R^1$, $R^2$, $R^3$, $R^4$, $R^5$, $R^6$, $R^7$ and $R^8$ in formula (I) represents a monovalent substituent. As the examples of the hetero atoms in the case where the formed ring structures are heterocyclic rings, N, O and S are exemplified.

When n represents 1, $R^5$ or $R^6$ and $R^7$ or $R^8$ may be linked to each other to form an aliphatic ring, but they do not form an aromatic ring. The aliphatic ring to be formed is preferably any of a 3- to 6-membered ring, and more preferably a 5- or 6-membered ring.

The sensitizing colorant is more preferably represented by the following formula (IA).

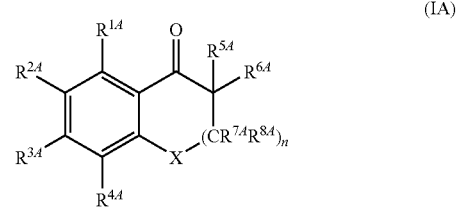

(IA)

In formula (IA), X represents O or S; n represents 0 or 1; each of $R^{1A}$, $R^{2A}$, $R^{3A}$, $R^{4A}$, $R^{5A}$, $R^{6A}$, $R^{7A}$, and $R^{8A}$ independently represents a hydrogen atom, an alkyl group, a halogen atom, a hydroxyl group, a cyano group, a nitro group, an amino group, an alkylthio group, an alkylamino group, an alkoxy group, an alkoxycarbonyl group, an acyloxy group, an acyl group, a carboxyl group, or a sulfo group, and contiguous two of $R^{1A}$, $R^{2A}$, $R^{3A}$ and $R^{4A}$ may be linked (condensed) to each other to form a ring. $R^{5A}$ or $R^{6A}$ and $R^{7A}$ or $R^{8A}$ may be linked to each other to form an aliphatic ring, but they do not form an aromatic ring.

The sensitizing colorant is still more preferably represented by the following formula (IB).

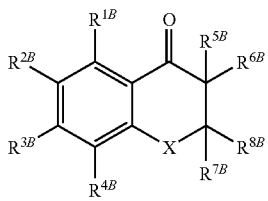

(IB)

In formula (IB), X represents O or S; each of $R^{1B}$, $R^{2B}$, $R^{3B}$, $R^{4B}$, $R^{5B}$, $R^{6B}$, $R^{7B}$, and $R^{8B}$ independently represents a hydrogen atom, an alkyl group, a halogen atom, a hydroxyl group, a cyano group, a nitro group, an amino group, an alkylthio group, an alkylamino group, an alkoxy group, an alkoxycarbonyl group, an acyloxy group, an acyl group, a carboxyl group, or a sulfo group, and contiguous two of $R^{1B}$, $R^{2B}$, $R^{3B}$ and $R^{4B}$ may be linked (condensed) to each other to form a ring. $R^{5B}$ or $R^{6B}$ and $R^{7B}$ or $R^{8B}$ may be linked to each other to form an aliphatic ring, but they do not form an aromatic ring.

The sensitizing colorant is still yet preferably represented by the following formula (IC).

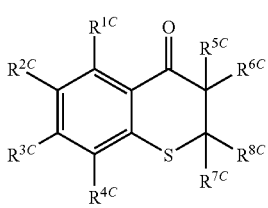

(IC)

In formula (IC), each of $R^{1C}$, $R^{2C}$, $R^{3C}$, $R^{4C}$, $R^{5C}$, $R^{6C}$, $R^{7C}$, and $R^{8C}$ independently represents a hydrogen atom, an alkyl group, a halogen atom, a hydroxyl group, a cyano group, a nitro group, an amino group, an alkylthio group, an alkylamino group, an alkoxy group, an alkoxycarbonyl group, an acyloxy group, an acyl group, a carboxyl group, or a sulfo group.

Contiguous two of $R^{1C}$, $R^{2C}$, $R^{3C}$ and $R^{4C}$ may be linked to each other to form a 5- or 6-membered aliphatic or aromatic ring. These rings may be heterocyclic rings containing elements other than a carbon atom, and formed rings may further form a binuclear ring, e.g., a condensed ring by combination. These ring structures may further have a substituent such as the substituents exemplified in the case where each of $R^1$, $R^2$, $R^3$, $R^4$, $R^5$, $R^6$, $R^7$ and $R^8$ in formula (I) represents a monovalent substituent. As the examples of the hetero atoms in the case where the formed ring structures are heterocyclic rings, N, O and S are exemplified. $R^{5C}$ or $R^{6C}$ and $R^{7C}$ or $R^{8C}$ may be linked to each other to form an aliphatic ring, but they do not form an aromatic ring.

It is preferred that at least one of $R^{1C}$, $R^{2C}$, $R^{3C}$, $R^{4C}$, $R^{5C}$, $R^{6C}$, $R^{7C}$, and $R^{8C}$ represents a halogen atom. As preferred substitution positions of halogen atoms, $R^{1C}$, $R^{2C}$, $R^{3C}$ and $R^{4C}$ are exemplified, and $R^{2C}$ is most preferred. The number of halogen atoms is preferably one or two, and more preferably one.

Further, $R^{2C}$ is preferably a substituent other than hydrogen, preferably an alkyl group, a halogen atom, an acyloxy group or an alkoxycarbonyl group, and especially preferably an alkyl group or a halogen atom, and in this case good matching with a light source is obtained, and high sensitivity can be ensured.

In addition, it is preferred that either $R^{7C}$ or $R^{8C}$ represents a substituent other than hydrogen, and it is more preferred both $R^{7C}$ and $R^{8C}$ represent substituents other than hydrogen. As preferred substituents, an alkyl group, a halogen atom, a carboxyl group, and an alkoxycarbonyl group are exemplified, an alkyl group and an alkoxycarbonyl group are more preferred, and an alkyl group is most preferred.

When any of $R^{1C}$, $R^{2C}$, $R^{3C}$, $R^{4C}$, $R^{5C}$, $R^{6C}$, $R^{7C}$, and $R^{8C}$ represents an alkyl group, the alkyl group is preferably an alkyl group having 1 to 10 carbon atoms, and more preferably the alkyl group is preferably an alkyl group having 1 to 4 carbon atoms, such as a methyl group, an ethyl group, a propyl group, an n-butyl group, a sec-butyl group, or a t-butyl group.

When any of $R^{1C}$, $R^{2C}$, $R^{3C}$, $R^{4C}$, $R^{5C}$, $R^{6C}$, $R^{7C}$, and $R^{8C}$ represents a halogen atom, the halogen atom is a fluorine atom, a chlorine atom, a bromine atom, or an iodine atom, and a chlorine atom, a bromine atom, and an iodine atom are preferred.

When any of $R^{1C}$, $R^{2C}$, $R^{3C}$, $R^{4C}$, $R^{5C}$, $R^{6C}$, $R^{7C}$, and $R^{8C}$ represents an acyloxy group, the acyloxy group is preferably an aliphatic acyloxy group having 2 to 10 carbon atoms, and more preferably an aliphatic acyloxy group having 2 to 5 carbon atoms.

When any of $R^{1C}$, $R^{2C}$, $R^{3C}$, $R^{4C}$, $R^{5C}$, $R^{6C}$, $R^{7C}$, and $R^{8C}$ represents an alkoxycarbonyl group, the alkoxycarbonyl group is preferably an aliphatic alkoxycarbonyl group having 2 to 10 carbon atoms, and more preferably an aliphatic alkoxycarbonyl group having 2 to 5 carbon atoms.

The examples of the specific sensitizing colorants [(exemplified compounds (I-1) to (I-133)] that can be preferably used in the invention are shown below, but the invention is by no means restricted thereto. In the exemplified compounds (I-1) to (I-133), Me represents methyl group, $Bu^t$ represents tertiary-butyl group and $Pr^i$ represents isopropyl group.

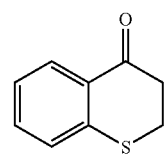

(I-1)

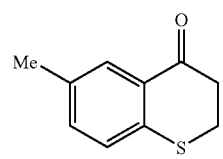

(I-2)

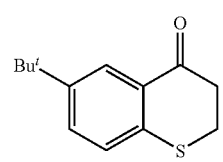

(I-3)

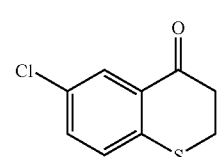

(I-4)

-continued
(I-5)
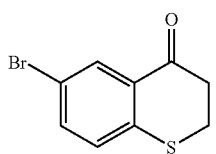
(I-6)
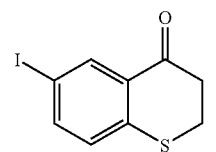
(I-7)
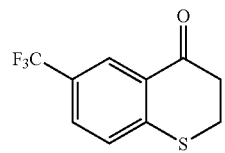
(I-8)
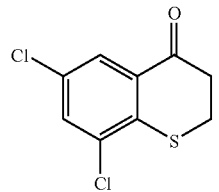
(I-9)
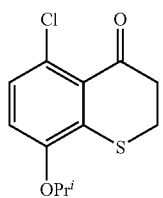
(I-10)
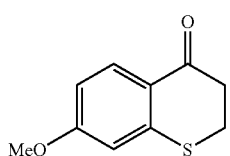
(I-11)
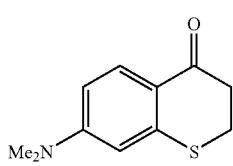
(I-12)
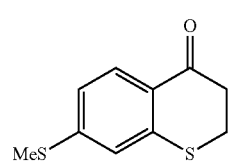
(I-13)
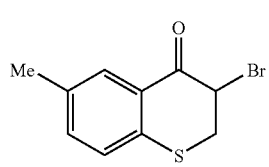
-continued
(I-14)
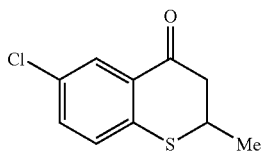
(I-15)
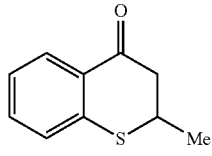
(I-16)
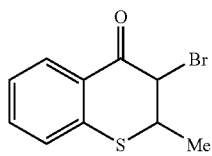
(I-17)
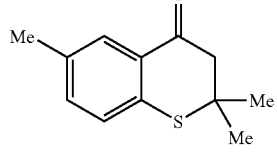
(I-18)
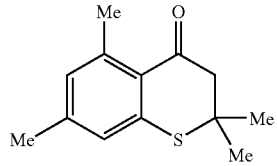
(I-19)
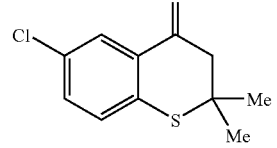
(I-20)
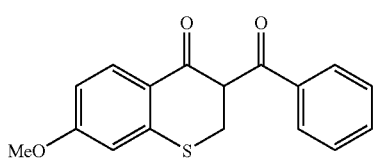
(I-21)
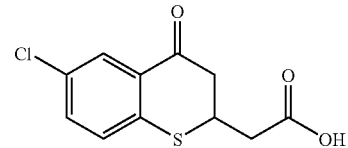
(I-22)
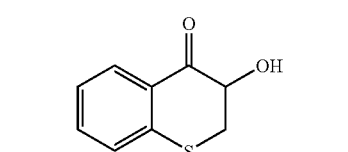
(I-23)
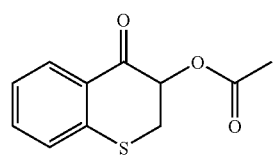

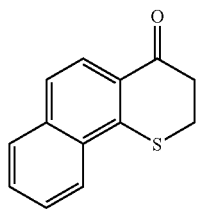 (I-24)
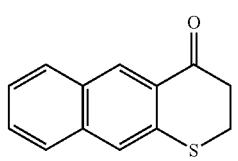 (I-25)
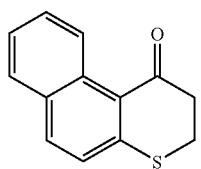 (I-26)
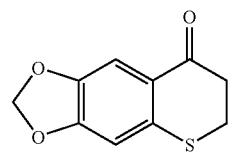 (I-27)
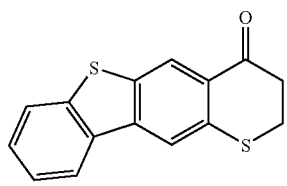 (I-28)
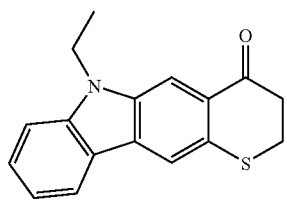 (I-29)
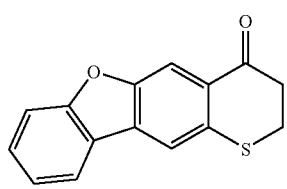 (I-30)
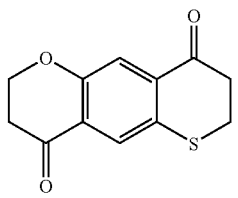 (I-31)
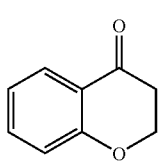 (I-32)
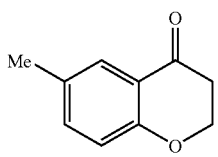 (I-33)
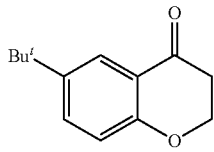 (I-34)
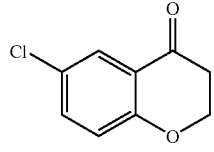 (I-35)
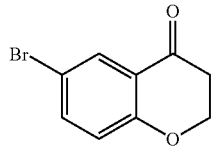 (I-36)
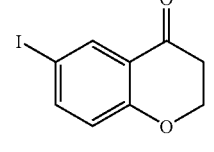 (I-37)
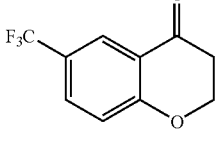 (I-38)
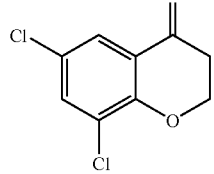 (I-39)
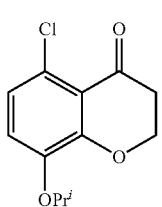 (I-40)

(I-41) 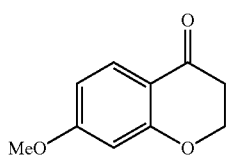
(I-42) 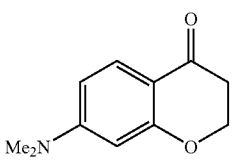
(I-43) 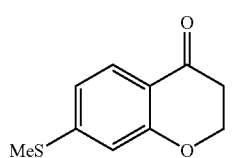
(I-44) 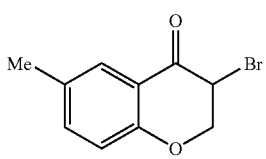
(I-45) 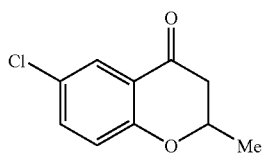
(I-46) 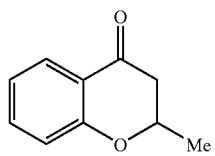
(I-47) 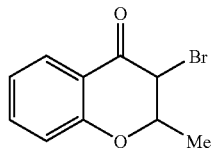
(I-48) 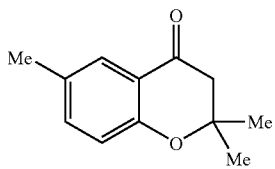
(I-49) 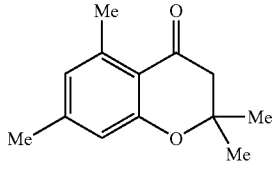
(I-50) 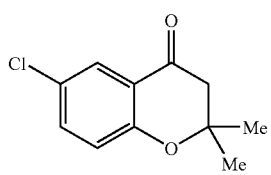
(I-51) 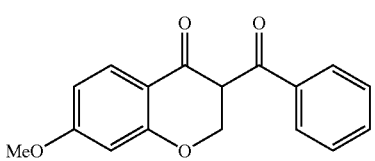
(I-52) 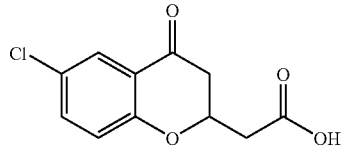
(I-53) 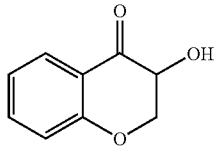
(I-54) 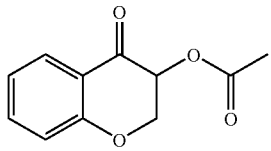
(I-55) 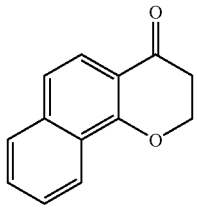
(I-56) 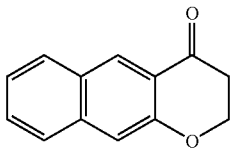
(I-57) 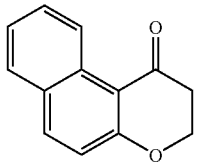
(I-58) 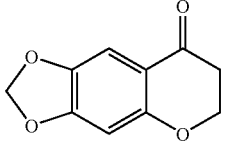

-continued
(I-59) 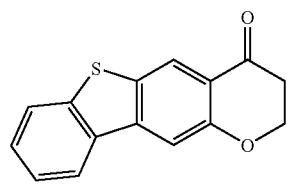
(I-60) 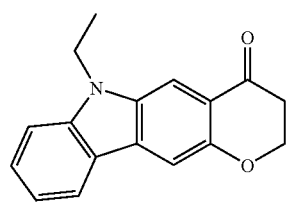
(I-61) 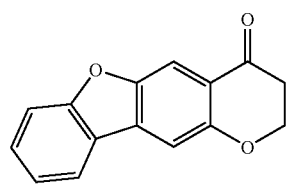
(I-62) 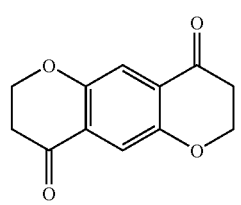
(I-63) 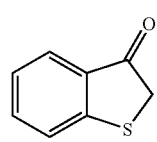
(I-64) 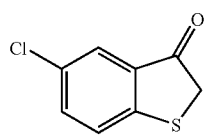
(I-65) 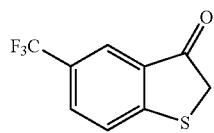
(I-66) 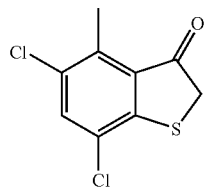
(I-67) 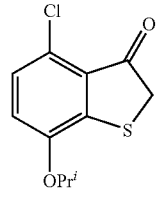
-continued
(I-68) 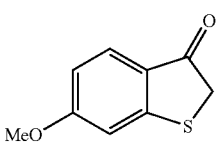
(I-69) 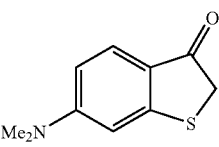
(I-70) 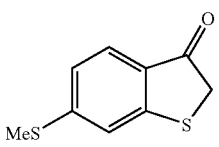
(I-71) 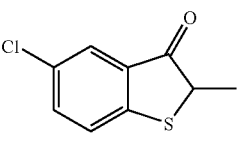
(I-72) 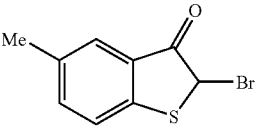
(I-73) 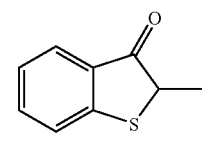
(I-74) 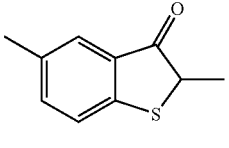
(I-75) 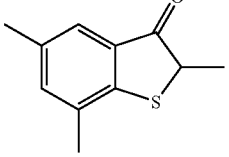
(I-76) 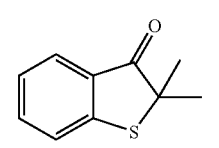
(I-77) 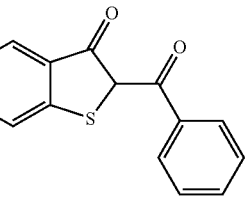

| 21 -continued | | 22 -continued | |
|---|---|---|---|
| 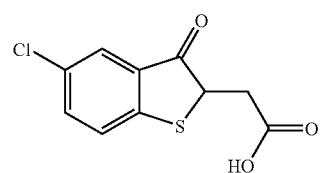 | (I-78) | 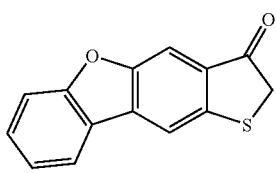 | (I-87) |
| 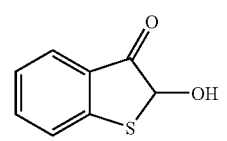 | (I-79) | 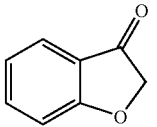 | (I-88) |
| 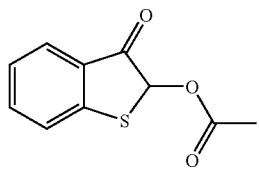 | (I-80) | 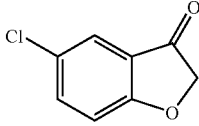 | (I-89) |
| 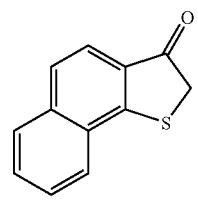 | (I-81) | 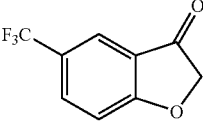 | (I-90) |
| 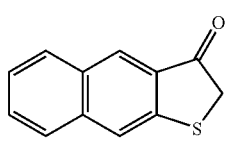 | (I-82) | 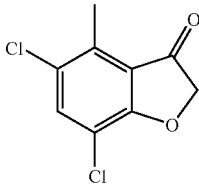 | (I-91) |
| 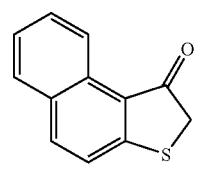 | (I-83) | 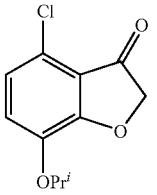 | (I-92) |
| 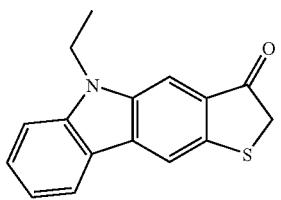 | (I-84) | 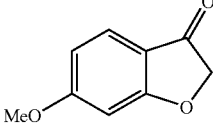 | (I-93) |
| 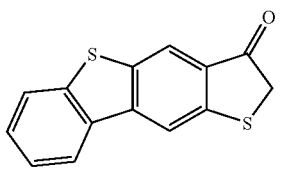 | (I-85) | 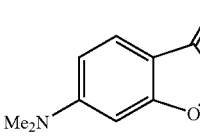 | (I-94) |
| | | 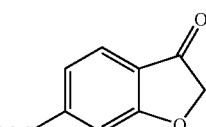 | (I-95) |
| 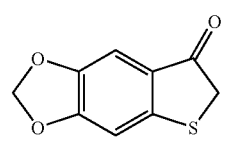 | (I-86) | 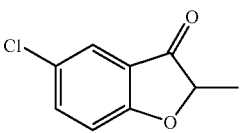 | (I-96) |

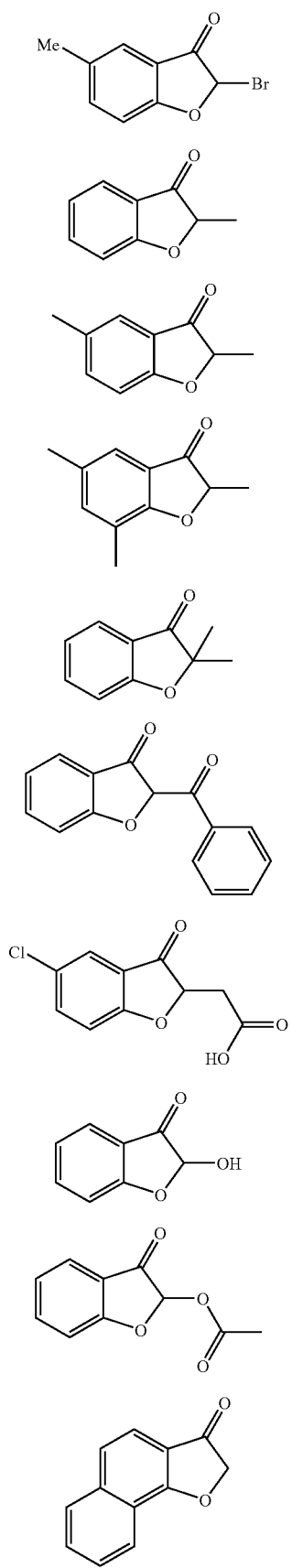
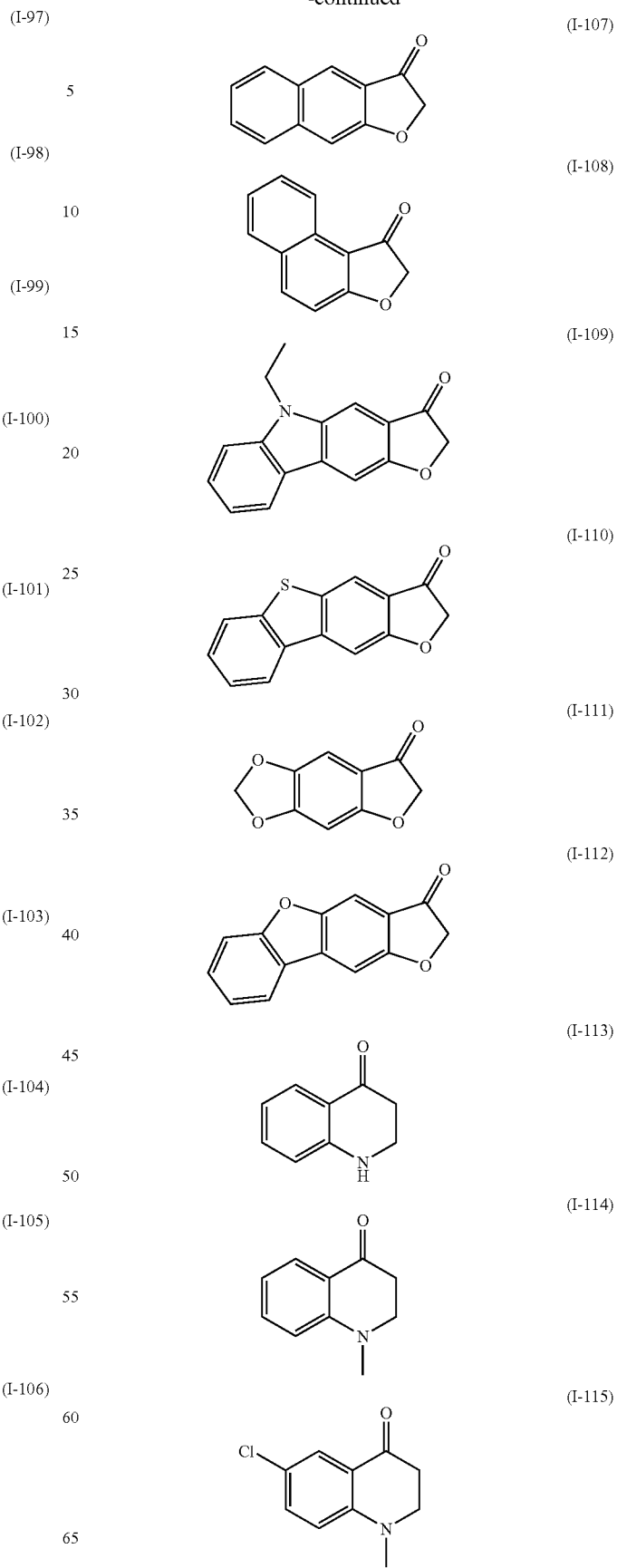

-continued
(I-116) 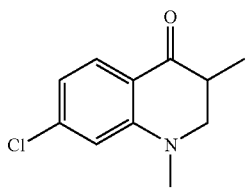
(I-117) 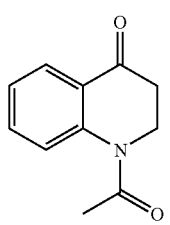
(I-118) 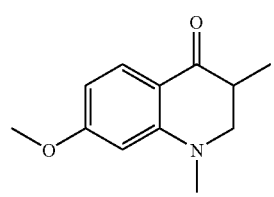
(I-119) 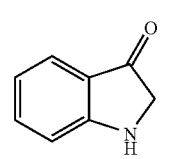
(I-120) 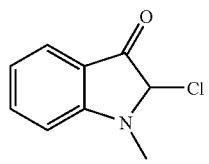
(I-121) 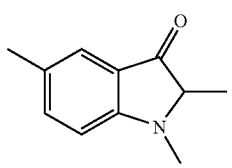
(I-122) 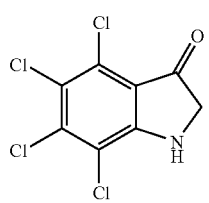
(I-123) 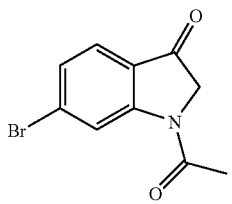
-continued
(I-124) 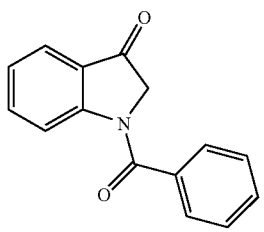
(I-125) 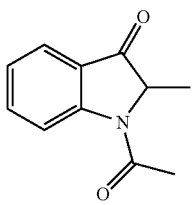
(I-126) 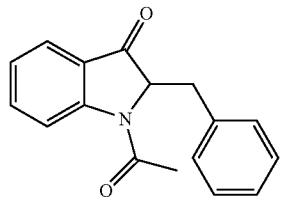
(I-127) 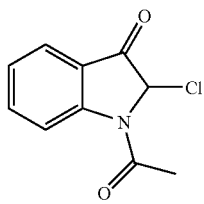
(I-128) 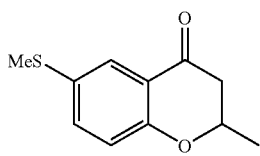
(I-129) 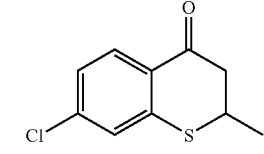
(I-130) 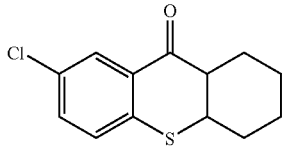
(I-131) 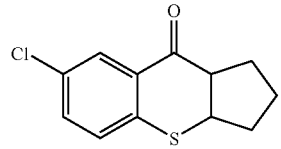

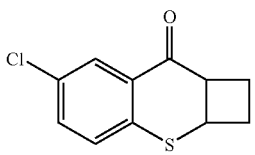

(I-132)

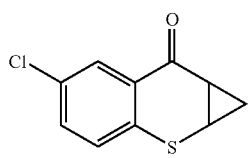

(I-133)

The specific sensitizing colorants in the invention can be synthesized according to the known methods described, e.g., in JP-A No. 2004-189695, "Tetrahedron", Vol. 49, p. 939 (1993), "Journal of Organic Chemistry", p. 893 (1945), and "Journal of Organic Chemistry", p. 4939 (1965).

The content of the specific sensitizing colorants in the photo-curable composition in the invention is preferably 0.05 to 30 mass % or so as solid content based on the photo-curable composition, more preferably 0.1 to 20 mass %, and still more preferably 0.2 to 10 mass %.

Incidentally, since the specific sensitizing colorants hardly have absorption in the visible ray region, they also have an advantage such that even when the amount capable of exhibiting the effect is added, there is no anxiety to affect the hue of the photo-curable composition.

In connection with the content, describing in relationship with the later-described onium salts, the content of the specific sensitizing colorants is in a mass ratio of onium salt/specific sensitizing colorants of 200/1 to 1/200, preferably 50/1 to 1/50, and more preferably 20/1 to 1/5.

[Other Sensitizing Colorants]

In the invention, in addition to the specific sensitizing colorants, other known sensitizing colorants can be used in combination so far as the effect of the invention is not impaired.

It is possible to add other sensitizing colorants to the specific sensitizing colorants in a mass ratio of the specific sensitizing colorants/other sensitizing colorants of 1/5 to 100/1, preferably 1/1 to 100/1, and more preferably 2/1 to 100/1.

Known sensitizing colorants that can be used in combination belong to the compounds exemplified below, and those having absorption wavelength in the wavelength region of 300 to 450 nm are exemplified.

For example, polynuclear aromatic compounds (e.g., phenanthrene, anthracene, pyrene, perylene, triphenylene, 9,10-dialkoxyanthracene), xanthenes (e.g., fluorescein, Eosine, Erythrocin, Rhodamine B, Rose Bengal), thioxanthones other than the specific sensitizing colorants (e.g., isopropylthioxanthone, diethylthioxanthone, chlorothioxanthone), cyanines (e.g., thiacarbocyanine, oxacarbocyanine), merocyanines (e.g., merocyanine, carbomerocyanine), phthalocyanines, thiazines (e.g., Thionine, Methylene Blue, Toluidine Blue), acridines (e.g., Acridine Orange, chloroflavine, acriflavine), anthraquinones (e.g., anthraquinone), squaryliums (e.g., squarylium), Acridine Orange, coumarins (e.g., 7-diethylamino-4-methylcoumarin), ketocoumarin, phenothiazines, phenazines, styrylbenzenes, azo compounds, diphenylmethane, triphenylmethane, distyrylbenzenes, carbazoles, porphyrin, spiro compounds, quinacridone, indigo, styryl, pyrylium compounds, pyrromethene compounds, pyrazolotriazole compounds, benzothiazole compounds, barbituric acid derivatives, and thiobarbituric acid derivatives are exemplified. Further, the compounds disclosed in EP 568, 993, U.S. Pat. Nos. 4,508,811, 5,227,227, JP-A Nos. 2001-125255 and 11-271969 are exemplified.

Above all in the invention, polynuclear aromatic compounds (e.g., phenanthrene, anthracene, pyrene, perylene, triphenylene, 9,10-dialkoxyanthracene), thioxanthones other than the specific sensitizing colorants, distyrylbenzenes, styrylbenzenes, and diphenylbutadienes are preferred, and distyrylbenzenes, styrylbenzenes, and diphenylbutadienes are most preferred.

As the sensitizing colorants that can be used in the invention, the following compounds are specifically exemplified.

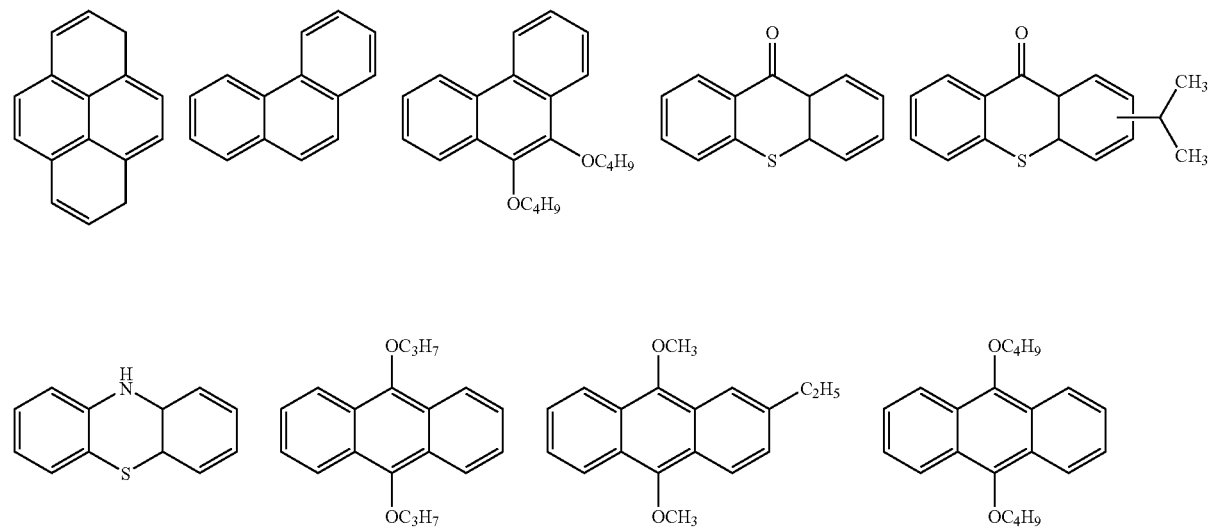

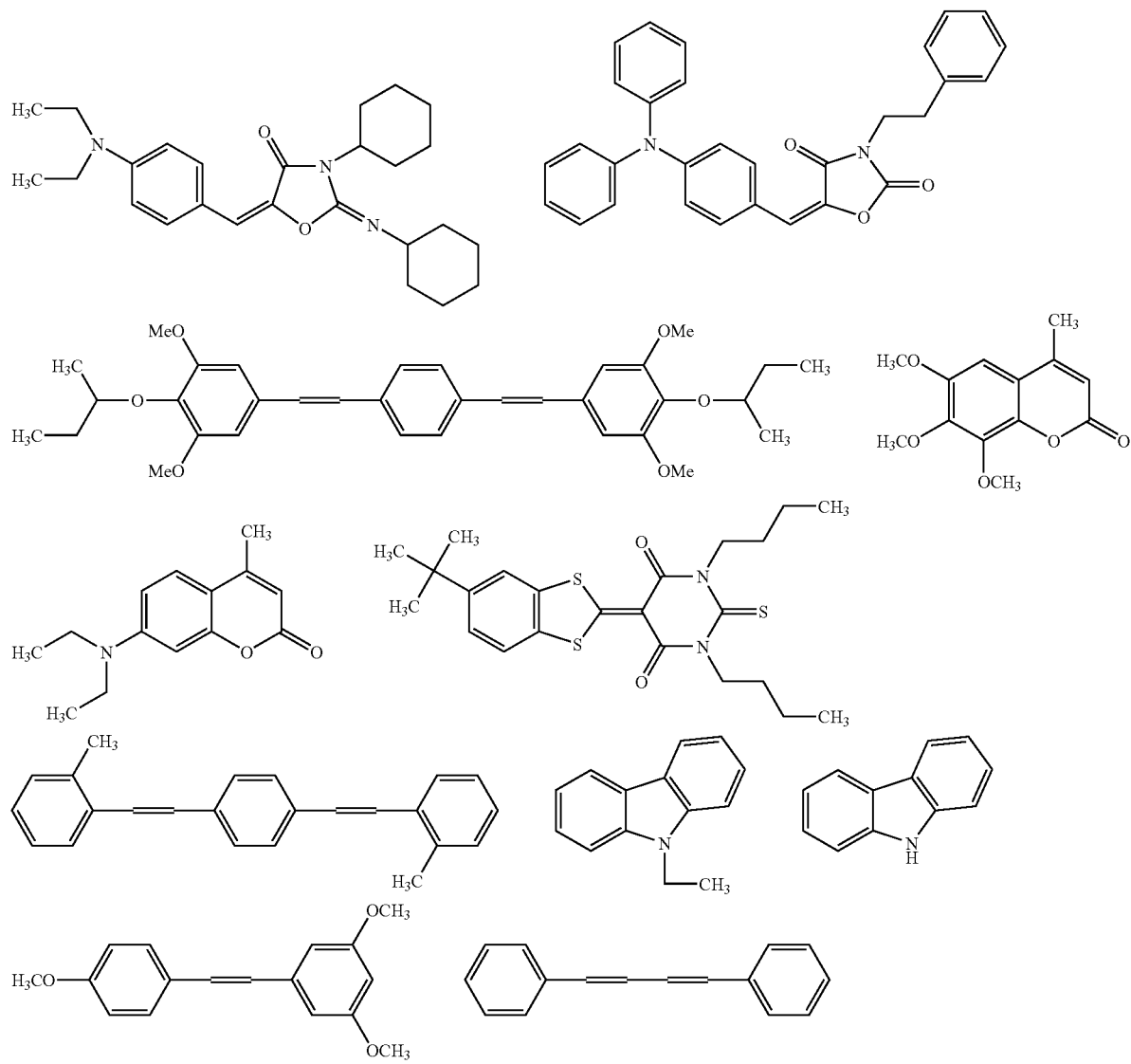

<Onium Salt (C)>

The photo-curable composition of the invention contains onium salt (C).

As representative onium salts in the invention, diazonium salts, sulfonium salts, sulfoxonium salts, iodonium salts, phosphonium salts, pyridinium salts, benzoxazolium salts, benzothiazolium salts, and ammonium salts are exemplified. For example, diazonium salts described in S. I. Schlesinger, Photogr. Sci. Eng., 18, 387 (1974), and T. S. Bal et al., Polymer, 21, 423 (1980), ammonium salts disclosed in U.S. Pat. Nos. 4,069,055, 4,069,056, Re27,992, and JP-A No. 3-140140, phosphonium salts disclosed in D. C. Necker et al, Macromolecules, 17, 2468 (1984), C. S. Wen et al., Teh, Proc. Conf. Rad. Curing ASIA, p. 478, Tokyo, (October, 1988), U.S. Pat. Nos. 4,069,055 and 4,069,056, iodonium salts described in J. V. Crivello et al., Macromolecules, 10 (6), 1307 (1977), Chem. & Eng. News, p. 31 (28 Nov. 1988), EP Nos. 104,143, 339,049, 410,201, JP-A Nos. 2-150848 and 2-296514, and sulfonium salts described in J. V. Crivello et al., Polymer J. 17, 73 (1985), J. V. Crivello et al., J. Org. Chem., 43, 3055 (1978), W. R. Watt et al., J. Polymer Sci., Polymer Chem. Ed., 22, 1789 (1984), J. V. Crivello et al., Polymer Bull., 14, 279 (1985), J. V. Crivello et al., Macromolecules, 14 (5), 1141 (1981), J. V. Crivello et al., J. Polymer Sci., Polymer Chem. Ed., 17, 2877 (1979), EP Nos. 370,693, 161,811, 410,201, 339,049, 233,567, 297,443, 297,442, U.S. Pat. Nos. 3,902,114, 4,933,377, 4,760,013, 4,734,444, 2,833,827, GP Nos. 2,904,626, 3,604,580, 3,604,581, JP-A Nos. 7-28237 and 8-27102 can be exemplified.

The onium salts in the invention are preferably the ones selected from the group consisting of the compounds represented by any of the following formulae (C1) to (C5).

(C1)

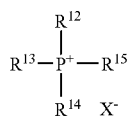
(C2)

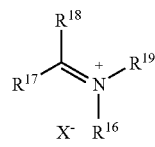
(C3)

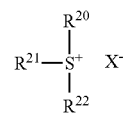
(C4)

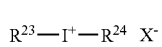
(C5)

In formulae (C1) to (C5), $R^{11}$ represents an aryl group; each of $R^{12}$, $R^{13}$, $R^{14}$, $R^{15}$ and $R^{16}$ independently represents an alkyl group, an alkenyl group, an alkynyl group, an aryl group, a hydrocarbocyclic group, a heterocyclic group, an alkoxy group, or an aryloxy group; each of $R^{17}$, $R^{18}$ and $R^{19}$ independently represents a hydrogen atom, a halogen atom, or a monovalent organic group; each of $R^{20}$, $R^{21}$ and $R^{22}$ independently represents a monovalent organic group; each of $R^{23}$ and $R^{24}$ independently represents an aryl group, an alkyl group, or a cycloalkyl group; and $X^-$ represents a non-nucleophilic anion.

The alkyl group represented by any of $R^{12}$ to $R^{16}$ is preferably an alkyl group having 1 to 30 carbon atoms, more preferably 1 to 20 carbon atoms, and especially preferably 1 to 8 carbon atoms, which may be straight chain or may have a substituent.

The alkenyl group represented by any of $R^{12}$ to $R^{16}$ is preferably an alkenyl group having 2 to 30 carbon atoms, more preferably 2 to 20 carbon atoms, and especially preferably 2 to 8 carbon atoms, which may further have a substituent.

The alkynyl group represented by any of $R^{12}$ to $R^{16}$ is preferably an alkynyl group having 2 to 30 carbon atoms, more preferably 2 to 20 carbon atoms, and especially preferably 2 to 8 carbon atoms, which may further have a substituent.

The aryl group represented by $R^{11}$, $R^{12}$ to $R^{16}$ is preferably an aryl group having 6 to 30 carbon atoms, more preferably 6 to 20 carbon atoms, and especially preferably 6 to 10 carbon atoms, which may further have a substituent.

The hydrocarbocyclic group represented by any of $R^{12}$ to $R^{16}$ is preferably a hydrocarbocyclic group having 3 to 30 carbon atoms, more preferably 3 to 20 carbon atoms, and especially preferably 3 to 10 carbon atoms, which may further have a substituent.

The heterocyclic group represented by any of $R^{12}$ to $R^{16}$ is preferably a heterocyclic group having 4 to 30 carbon atoms, more preferably 4 to 20 carbon atoms, and especially preferably 4 to 10 carbon atoms, which may further have a substituent. The hetero atom contained in the heterocyclic group is preferably a nitrogen atom, an oxygen atom or a sulfur atom.

The alkoxy group represented by any of $R^{12}$ to $R^{16}$ is preferably an alkoxy group having 1 to 30 carbon atoms, more preferably 1 to 20 carbon atoms, and especially preferably 1 to 8 carbon atoms, which may further have a substituent as described later. The alkyl portion of the alkoxy group may be an alkenyl group, an alkynyl group, a hydrocarbocyclic group, or a heterocyclic group not aromatic.

The aryloxy group represented by any of $R^{12}$ to $R^{16}$ is preferably an aryloxy group having 6 to 30 carbon atoms, more preferably 6 to 20 carbon atoms, and especially preferably 6 to 10 carbon atoms. The aryloxy group may further have a substituent as described later. The aryl portion of the aryloxy group may be an aromatic heterocyclic group.

In formula (C2), two or more of $R^{12}$, $R^{13}$, $R^{14}$ and $R^{15}$ may be bonded to form a ring, if possible.

In formula (C3), two or more of $R^{17}$, $R^{18}$ and $R^{19}$ may be bonded to form a ring, if possible.

As the substituents that the alkyl group, alkenyl group, alkynyl group, aryl group, hydrocarbocyclic group, heterocyclic group, alkoxy group, or aryloxy group may have, monovalent nonmetal atomic groups exclusive of hydrogen are used, and as preferred examples, the groups described in the above substituents are exemplified. These substituents may further be substituted with the above substituents, or they may form a ring, if possible.

As the halogen atom represented by $R^{17}$, $R^{18}$ and $R^{19}$, a fluorine atom, a chlorine atom, a bromine atom, and an iodine atom are exemplified, but preferably a fluorine atom, a chlorine atom, and a bromine atom are preferred.

The monovalent organic group represented by $R^{17}$, $R^{18}$ and $R^{19}$ is a hydroxyl group, an alkyl group, an alkenyl group, an alkynyl group, an aryl group, a hydrocarbocyclic group, a heterocyclic group, an alkoxy group, an aryloxy group, an acyl group, an alkoxycarbonyl group, an acyloxy group, —SO$_3$—Ra, —NRbRc, a cyano group, —SiRdReRf, —SORg, —SO$_2$Rg, or a nitro group, where Ra represents a hydrogen atom, an alkyl group, an alkenyl group, an alkynyl group, an aryl group, an arylalkyl group, an alkali metal atom, or a quaternary ammonium; each of Rb, Rc and Rg independently represents an alkyl group, an alkenyl group, an alkynyl group, an aryl group, a hydrocarbocyclic group, or a heterocyclic group; and each of Rd, Re and Rf independently represents an alkyl group, an alkenyl group, an alkynyl group, an aryl group, a hydrocarbocyclic group, a heterocyclic group, an alkoxy group, or an aryloxy group.

The alkyl group, alkenyl group, alkynyl group, aryl group, hydrocarbocyclic group, heterocyclic group, alkoxy group, and aryloxy group represented by $R^{17}$, $R^{18}$ and $R^{19}$ have the same meanings as those in $R^{12}$ to $R^{16}$ above, and preferred ranges are also the same. Each of these groups may be a straight chain or may have a substituent as described above.

The acyl group or alkoxycarbonyl group represented by $R^{17}$, $R^{18}$ and $R^{19}$ preferably has carbon atoms on the carbon chain side of 1 to 30, and especially preferably 1 to 12 carbon atoms, which may be a straight chain or may have the above substituent.

The acyloxy group represented by $R^{17}$, $R^{18}$ and $R^{19}$ preferably has carbon atoms of 1 to 30, and especially preferably 1 to 12 carbon atoms, which may have the above substituent even when it is straight chain.

Ra in —SO$_3$—Ra represented by $R^{17}$, $R^{18}$ and $R^{19}$ is preferably a hydrogen atom, the alkyl group that may have the substituent, the aryl group that may have the substituent, a lithium atom, a sodium atom, or a potassium atom.

The alkyl group, alkenyl group, alkynyl group, aryl group, hydrocarbocyclic group, and heterocyclic group in Rb and Rc in —NRbRc are the same meanings as those in $R^{12}$ to $R^{16}$ and preferred ranges are also the same. These groups may have the substituents.

The alkyl group, alkenyl group, alkynyl group, aryl group, hydrocarbocyclic group, heterocyclic group, alkoxy group, and aryloxy group in Rd, Re and Rf in —SiRdReRf are the same meanings as those in $R^{12}$ to $R^{16}$, and preferred ranges are also the same. These groups may have the substituents.

In addition, the alkyl group, alkenyl group, alkynyl group, aryl group, hydrocarbocyclic group, and heterocyclic group in Rg in —SORg or —SO$_2$Rg are the same meanings as those in $R^{12}$ to $R^{16}$, and preferred ranges are also the same. These groups may have the substituents.

In formula (C4), each of $R^{20}$, $R^{21}$ and $R^{22}$ independently represents a monovalent organic group.

The carbon atom number of the monovalent organic group represented by $R^{20}$, $R^{21}$ and $R^{22}$ is generally 1 to 30, and preferably 1 to 20.

Two of $R^{20}$, $R^{21}$ and $R^{22}$ may be bonded to form a ring structure, and an oxygen atom, a sulfur atom, an ester bond, an amido bond, or a carbonyl group may be contained in the ring. As the group to be formed by bonding two of $R^{20}$, $R^{21}$ and $R^{22}$, an alkylene group (e.g., a butylenes group, a pentylene group) can be exemplified.

As the specific examples of the monovalent organic groups represented by $R^{20}$, $R^{21}$ and $R^{22}$, corresponding groups in the later-described compounds (c1-1), (c1-2) and (c1-3) can be exemplified.

The compound represented by formula (C4) may be a compound having a plurality of structures represented by formula (C4). For example, the compound may have such a structure that at least one of $R^{20}$, $R^{21}$ and $R^{22}$ of the compound represented by formula (C4) may be bonded to at least one of $R^{20}$, $R^{21}$ and $R^{22}$ of other compound represented by formula (C4) directly or via a linking group.

In formula (C5), each of $R^{23}$ and $R^{24}$ independently represents an aryl group, an alkyl group, or a cycloalkyl group.

The aryl group represented by $R^{23}$ and $R^{24}$ is preferably a phenyl group or a naphthyl group, and more preferably a phenyl group.

The alkyl group represented by $R^{23}$ and $R^{24}$ may be straight chain or branched, and is preferably a straight chain or branched alkyl group having 1 to 10 carbon atoms (e.g., a methyl group, an ethyl group, a propyl group, a butyl group, and a pentyl group).

The cycloalkyl group represented by $R^{23}$ and $R^{24}$ is preferably a cycloalkyl group having 3 to 10 carbon atoms (e.g., a cyclopentyl group, a cyclohexyl group, and a norbonyl group).

As the examples of the substituents that $R^{23}$ and $R^{24}$ may have, for example, an alkyl group (e.g., having 1 to 15 carbon atoms), a cycloalkyl group (e.g., having 3 to 15 carbon atoms), an aryl group (e.g., having 6 to 15 carbon atoms), an alkoxy group (e.g., having 1 to 15 carbon atoms), a halogen atom, a hydroxyl group, and a phenylthio group can be exemplified.

In formulae (C1) to (C5), X$^-$ represents a non-nucleophilic anion, preferably a sulfonate anion, a carboxylate anion, a bis(alkylsulfonyl)amido anion, a tris(alkylsulfonyl)methide anion, BF$_4^-$, PF$_6^-$, SbF$_6^-$, and a group shown below are exemplified, and more preferably an organic anion having a carbon atom.

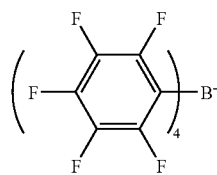

As preferred organic anions, organic anions as shown below are exemplified.

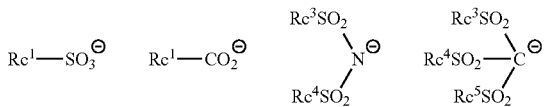

In the above formulae, Rc$^1$ represents an organic group.

As the organic group represented by Rc$^1$, a group having 1 to 30 carbon atoms is exemplified, and preferably an alkyl group, a cycloalkyl group, an aryl group, or a group obtained by linking a plurality of these groups via a linking group such as a single bond, —O—, —CO$_2$—, —S—, —SO$_3$—, —SO$_2$N(Rd$^1$)— are exemplified.

Rd$^1$ represents a hydrogen atom or an alkyl group.

Each of Rc$^3$, Rc$^4$ and Rc$^5$ independently represents an organic group.

As the organic groups represented by Rc$^3$, Rc$^4$ and Rc$^5$, the preferred organic groups as in Rc$^1$ can be preferably exemplified. The most preferred organic group is a perfluoroalkyl group having 1 to 4 carbon atoms.

Rc$^3$ and Rc$^4$ may be bonded to form a ring.

As the groups formed by Rc$^3$ and Rc$^4$ by bonding, an alkylene group and an arylene group are exemplified, and a preferred group is a perfluoroalkylene group having 2 to 4 carbon atoms.

As the organic groups represented by Rc$^1$, Rc$^3$, Rc$^4$ and Rc$^5$, an alkyl group substituted with a fluorine atom or a fluoroalkyl group at the 1-position, and a phenyl group substituted with a fluorine atom or a fluoroalkyl group are exemplified as the most preferable examples. By having a fluorine atom or a fluoroalkyl group, the acidity of acid generated by irradiation with light increases and sensitivity is bettered.

As preferred compounds represented by formula (C4), compounds represented by any of formulae (c1-1), (c1-2) and (c1-3) can be exemplified.

Compound (c1-1) is a compound represented by formula (C4) wherein at least one of $R^{20}$, $R^{21}$ and $R^{22}$ is an aryl group, that is, an arylsulfonium compound having arylsulfonium as the cation.

All of $R^{20}$, $R^{21}$ and $R^{22}$ of the arylsulfonium compound may be aryl groups, or a part of $R^{20}$, $R^{21}$ and $R^{22}$ may be an aryl group(s) and the remaining may be an alkyl group or a cycloalkyl group.

As the arylsulfonium compound, for example, a triarylsulfonium compound, a diarylalkylsulfonium compound, an aryldialkylsulfonium compound, a diarylcycloalkylsulfonium compound, and an aryldicycloalkylsulfonium compound are exemplified.

As the aryl groups of the arylsulfonium compound, an aryl group such as a phenyl group and a naphthyl group, and a heteroaryl group such as an indole residue and a pyrrole residue are preferred, and a phenyl group and an indole residue are more preferred. When the arylsulfonium compound has two or more aryl groups, these two or more aryl groups may be the same with or different from each other.

As the alkyl group that the arylsulfonium compound may have according to necessity, a straight chain or branched alkyl group having 1 to 15 carbon atoms is preferred and, e.g., a methyl group, an ethyl group, a propyl group, an n-butyl group, a sec-butyl group, and a t-butyl group can be exemplified.

As the cycloalkyl group that the arylsulfonium compound may have according to necessity, a cycloalkyl group having 3 to 15 carbon atoms is preferred and, e.g., a cyclopropyl group, a cyclobutyl group, and a cyclohexyl group can be exemplified.

The aryl group, alkyl group, and cycloalkyl group represented by $R^{20}$, $R^{21}$ and $R^{22}$ may have an alkyl group (e.g., having 1 to 15 carbon atoms), a cycloalkyl group (e.g., having 3 to 15 carbon atoms), an aryl group (e.g., having 6 to 14 carbon atoms), an alkoxy group (e.g., having 1 to 15 carbon atoms), a halogen atom, a hydroxyl group, or a phenylthio group as the substituent. Preferred substituents are a straight chain or branched alkyl group having 1 to 12 carbon atoms, a cycloalkyl group having 3 to 12 carbon atoms, and a straight chain, branched, or cyclic alkoxy group having 1 to 12 carbon atoms, and most preferred substituents are an alkyl group having 1 to 4 carbon atoms, and an alkoxy group having 1 to 4 carbon atoms. The substituent may be substituted with either one of $R^{20}$, $R^{21}$ and $R^{22}$, or may be substituted with all of the three. When $R^{20}$, $R^{21}$ and $R^{22}$ are aryl groups, it is preferred that the substituent be substituted on the p-position of the aryl groups.

The compound represented by formula (c1-2) will be described.

The compound (c1-2) is a compound represented by formula (C4) wherein each of $R^{20}$, $R^{21}$ and $R^{22}$ independently represents an organic group not containing an aromatic ring. The aromatic ring here means to include an aromatic ring containing a hetero atom also.

The organic group not containing an aromatic ring represented by $R^{20}$, $R^{21}$ and $R^{22}$ generally has 1 to 30 carbon atoms, and preferably 1 to 20 carbon atoms.

Each of $R^{20}$, $R^{21}$ and $R^{22}$ independently preferably represents an alkyl group, a cycloalkyl group, an allyl group, or a vinyl group, more preferably a straight chain, branched or cyclic 2-oxoalkyl group, or an alkoxycarbonylmethyl group, and especially preferably a straight chain or branched 2-oxoalkyl group.

The alkyl group represented by $R^{20}$, $R^{21}$ and $R^{22}$ may be either straight chain or branched, preferably a straight chain or branched alkyl group having 1 to 10 carbon atoms (e.g., a methyl group, an ethyl group, a propyl group, a butyl group, a pentyl group), and more preferably a straight chain or branched 2-oxoalkyl group, or an alkoxycarbonylmethyl group.

The cycloalkyl group represented by $R^{20}$, $R^{21}$ and $R^{22}$ is preferably a cycloalkyl group having 3 to 10 carbon atoms (e.g., a cyclopentyl group, a cyclohexyl group, a norbonyl group), and more preferably a cyclic 2-oxoalkyl group.

As the straight chain, branched or cyclic 2-oxoalkyl group represented by $R^{20}$, $R^{21}$ and $R^{22}$, a group having >C=O on the 2-position of the above alkyl group or cycloalkyl group can be preferably exemplified.

As the alkoxy group in the alkoxycarbonylmethyl group represented by $R^{20}$, $R^{21}$ and $R^{22}$, preferably an alkoxy group having 1 to 5 carbon atoms (e.g., a methoxy group, an ethoxy group, a propoxy group, a butoxy group, a pentoxy group) can be exemplified. $R^{20}$, $R^{21}$ and $R^{22}$ may further be substituted with a halogen atom, an alkoxy group (e.g., having 1 to 5 carbon atoms), a hydroxyl group, a cyano group, or a nitro group.

The compound (c1-3) is a compound represented by the following formula (c1-3), which is a compound having a phenacylsulfonium salt structure.

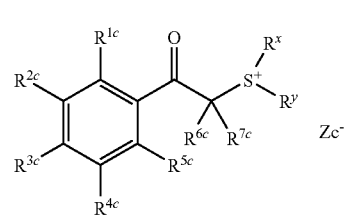

(c1-3)

In formula (c1-3), each of $R^{1c}$, $R^{2c}$, $R^{3c}$, $R^{4c}$ and $R^{5c}$ independently represents a hydrogen atom, an alkyl group, a cycloalkyl group, an alkoxy group, or a halogen atom.

Each of $R^{6c}$ and $R^{7c}$ independently represents a hydrogen atom, an alkyl group, a cycloalkyl group.

Each of $R^x$ and $R^y$ independently represents an alkyl group, a cycloalkyl group, an allyl group, or a vinyl group.

Any two or more of $R^{1c}$ to $R^{5c}$, $R^{6c}$ and $R^{7c}$ and $R^x$ and $R^y$ may be bonded to each other to form a ring structure.

$Zc^-$ represents a non-nucleophilic anion, and the same anions as the non-nucleophilic anions represented by $X^-$ in formulae (C1) to (C5).

The alkyl group represented by $R^{1c}$ to $R^{7c}$ may be either straight chain or branched, and, e.g., a straight chain or branched alkyl group having 1 to 20, preferably 1 to 12, carbon atoms (e.g., a methyl group, an ethyl group, a straight chain or branched propyl group, a straight chain or branched butyl group, a straight chain or branched pentyl group) can be exemplified.

As the cycloalkyl group represented by $R^{1c}$ to $R^{7c}$, preferably a cycloalkyl group having 3 to 8 carbon atoms (e.g., a cyclopentyl group, a cyclohexyl group) can be exemplified.

The alkoxy group represented by $R^{1c}$ to $R^{5c}$ may be any of straight chain, branched and cyclic, and, e.g., an alkoxy group having 1 to 10 carbon atoms, and preferably a straight chain or branched alkoxy group having 1 to 5 carbon atoms (e.g., a methoxy group, an ethoxy group, a straight chain or branched propoxy group, a straight chain or branched butoxy group, a straight chain or branched pentoxy group), a cyclic alkoxy group having 3 to 8 carbon atoms (e.g., a cyclopentyloxy group, a cyclohexyloxy group) can be exemplified.

As the groups formed by bonding two or more of $R^{1c}$ to $R^{5c}$, $R^{6c}$ and $R^{7c}$, and $R^x$ and $R^y$, a butylene group and a pentylene group can be exemplified. These ring structures may contain an oxygen atom, a sulfur atom, an ester bond, or an amido bond.

Any of $R^{1c}$ to $R^{5c}$ is (are) preferably a straight chain or branched alkyl group, a cycloalkyl group, or a straight chain, branched or cyclic alkoxy group, and more preferably the sum total of the carbon atoms of $R^{1c}$ to $R^{5c}$ is 2 to 15, by which solubility in a solvent is improved and generation of particles during preservation can be restrained.

As the alkyl group and cycloalkyl group represented by $R^x$ and $R^y$, the same alkyl group and cycloalkyl group represented by $R^{1c}$ to $R^{7c}$ can be exemplified.

$R^x$ and $R^y$ are preferably a 2-oxoalkyl group and an alkoxycarbonyl methyl group.

As the 2-oxoalkyl group, a group having >C=O at the 2-position of the alkyl group or cycloalkyl group represented by $R^{1c}$ to $R^{5c}$ can be exemplified.

As the alkoxy group in the alkoxycarbonylmethyl group, the same group as the alkoxy group represented by $R^{1c}$ to $R^{5c}$ can be exemplified.

$R^x$ and $R^y$ are preferably an alkyl group having 4 or more carbon atoms, or a cycloalkyl group having 4 or more carbon atoms, more preferably having 6 or more carbon atoms, and still more preferably an alkyl group having 8 or more carbon atoms, or a cycloalkyl group having 8 or more carbon atoms.
The preferred examples of the onium salts usable in the invention are shown below, but the invention is not restricted to these compounds.
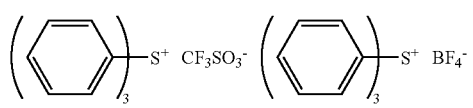
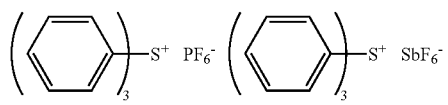
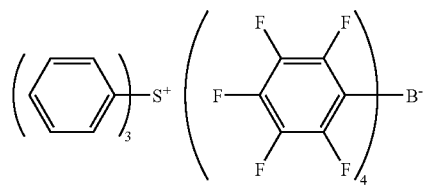
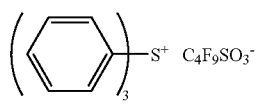
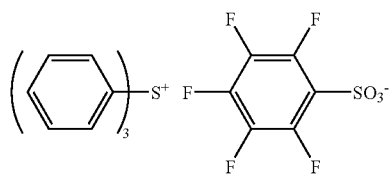
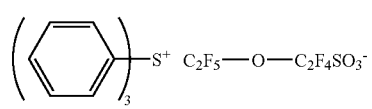
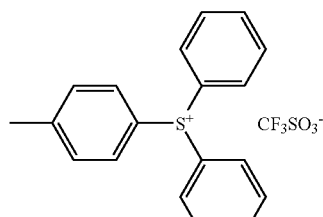
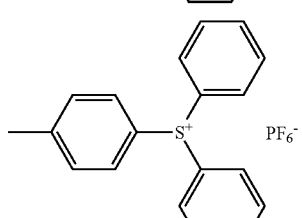
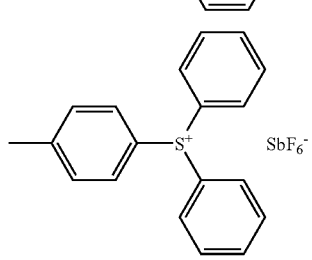
-continued
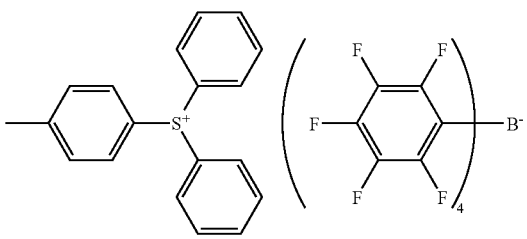
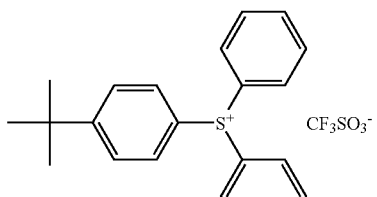
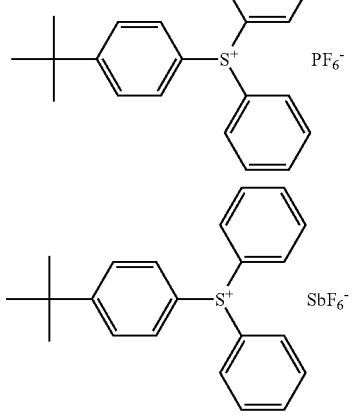
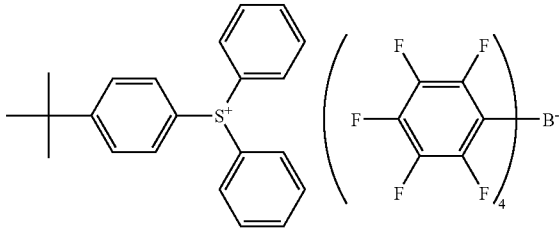
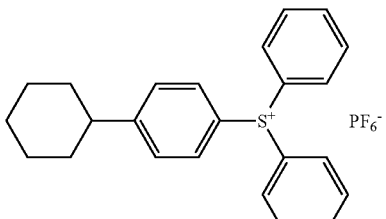
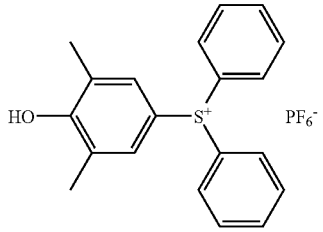

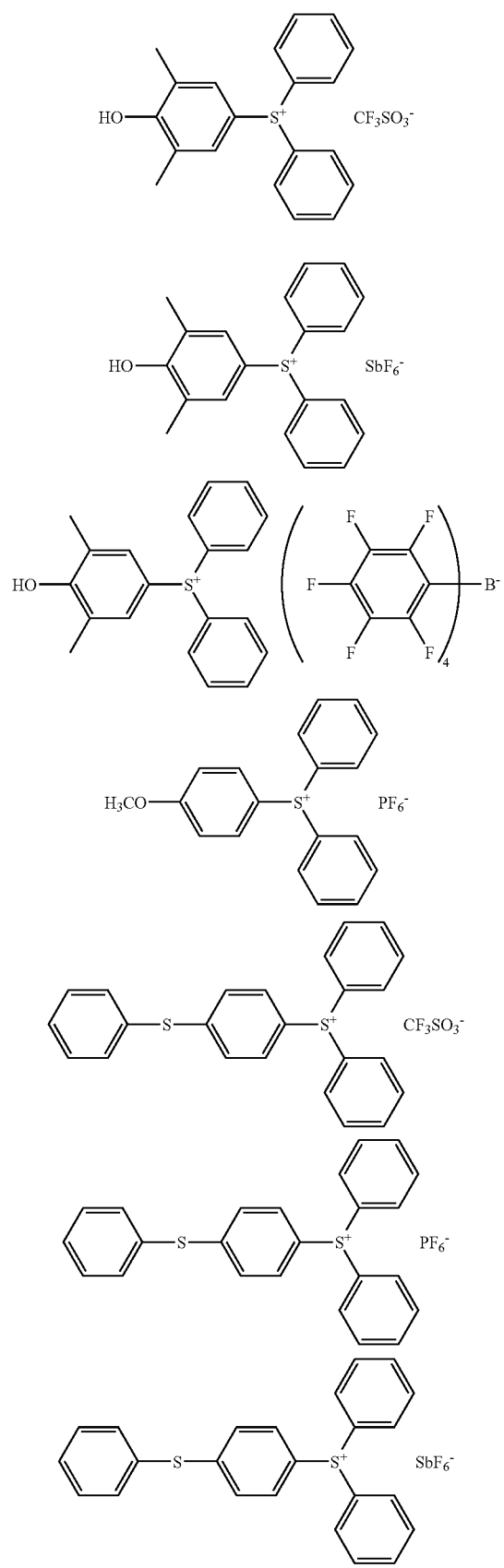
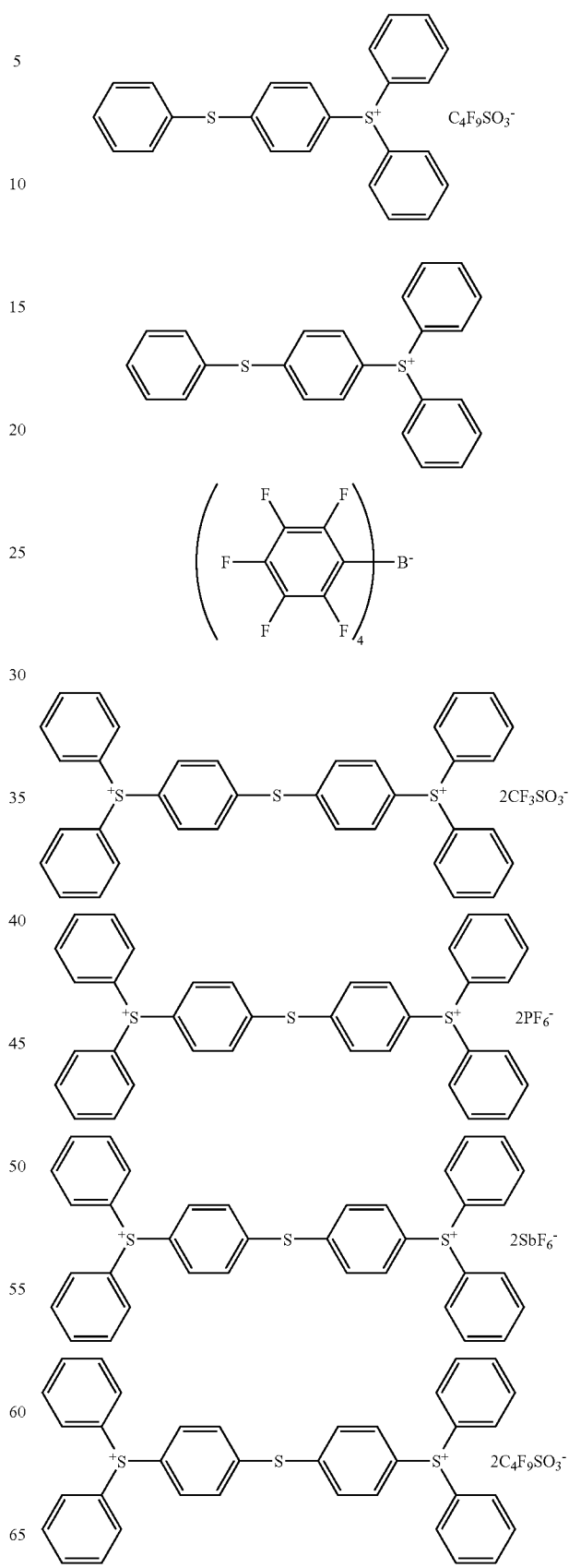

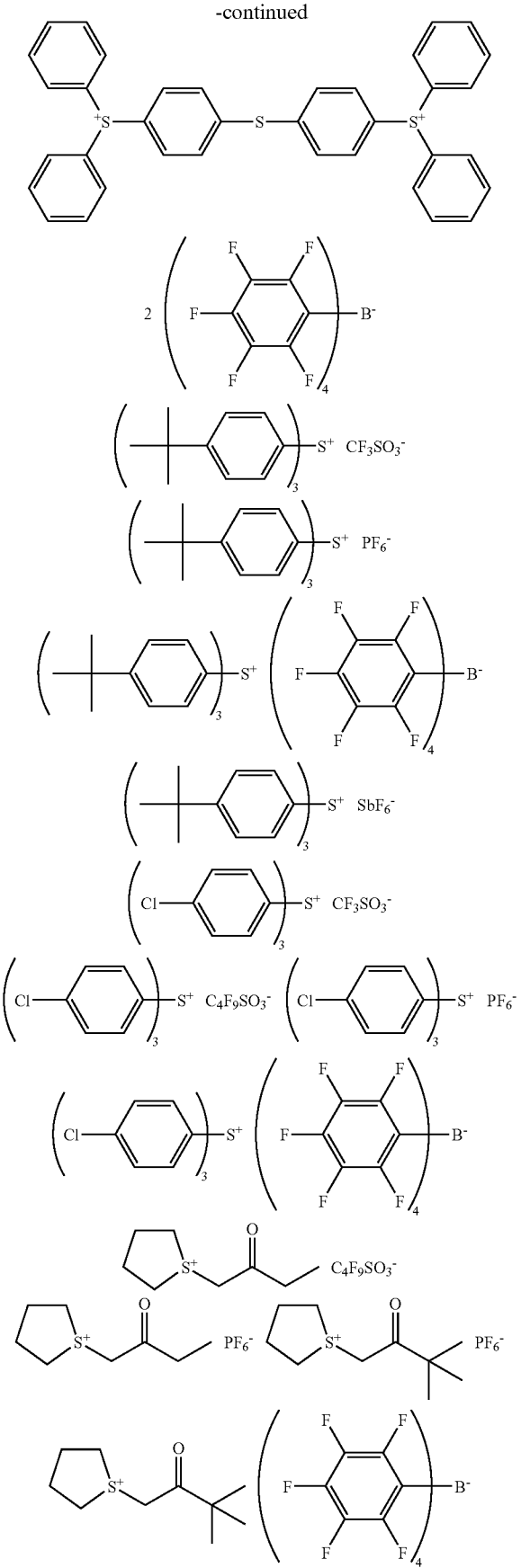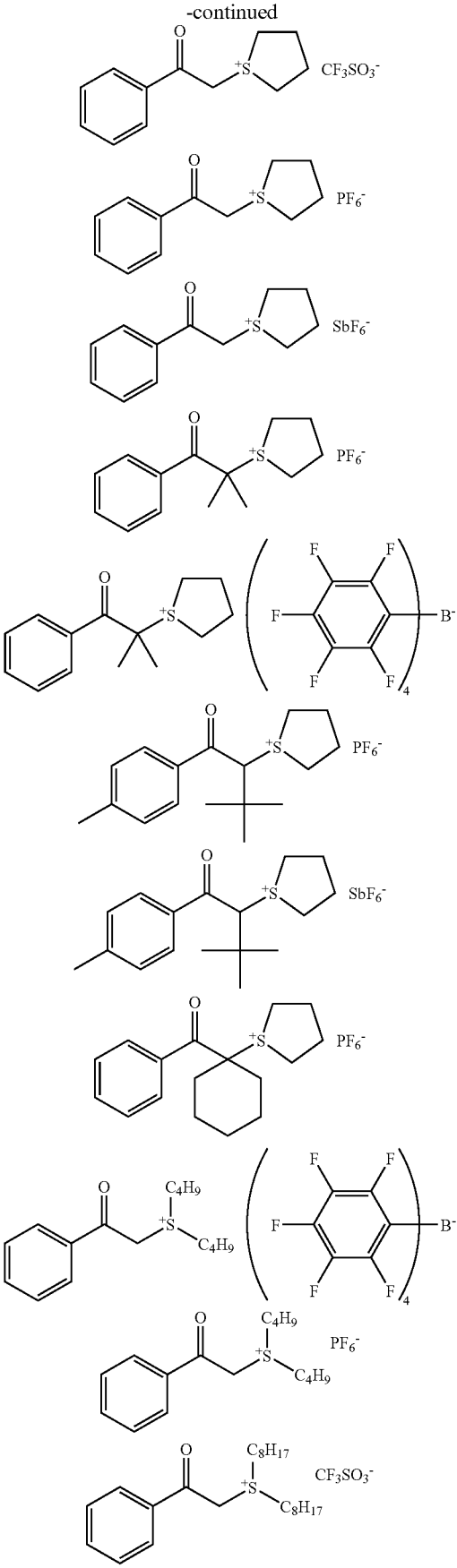

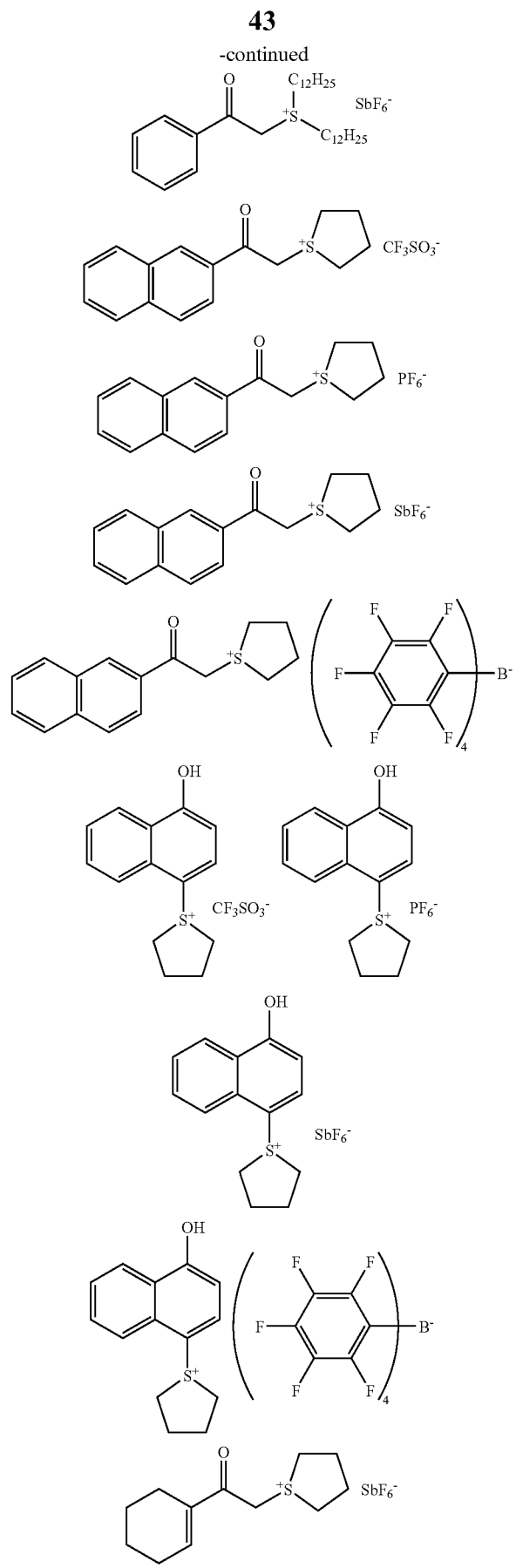
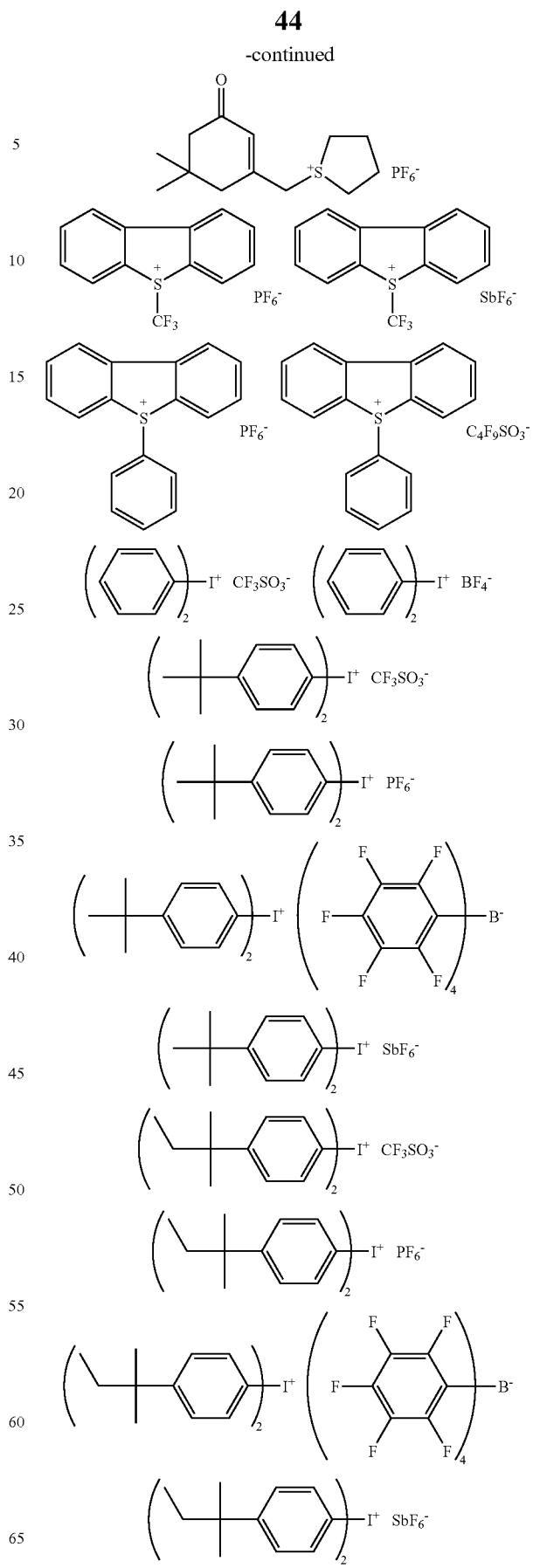

-continued

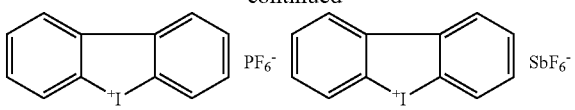
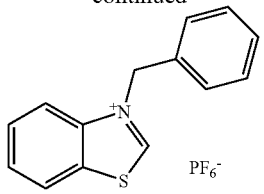
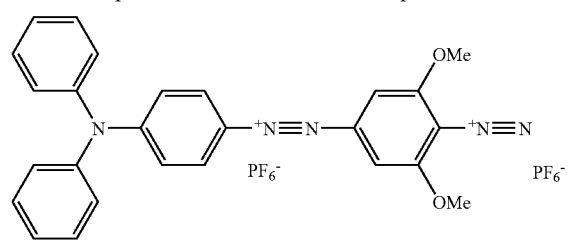
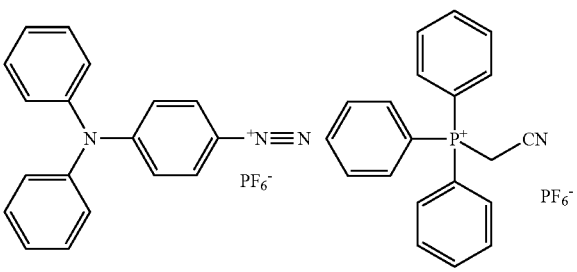
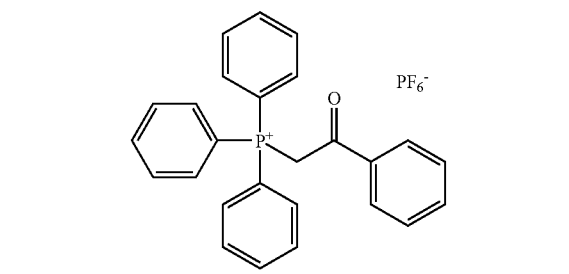
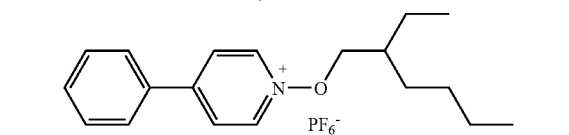
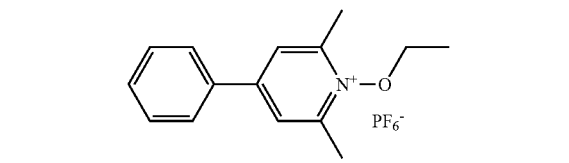
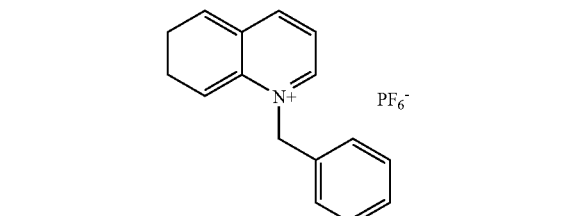
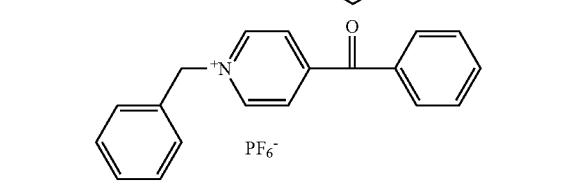
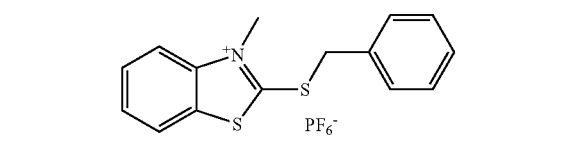

The sulfonium salts disclosed in JP-A No. 2007-254454 are also preferably used.

In the light of sensitivity, a diaryl iodonium salt is most preferably used as the iodonium salt. The iodonium salts disclosed in JP-A No. 2001-181221, and the diaryl iodonium salts disclosed in JP-A No. 2007-186568, paragraphs [0010] to [0027] can also be preferably used besides the compound represented by formula (C5).

As onium salts that can be preferably used in the invention, sulfonium salts, iodonium salts and phosphonium salts not containing basic structure having the possibility of hindering cationic polymerization are preferably used, and iodonium salts are preferred in the point of sensitivity.

The content of the onium salt in the photo-curable composition of the invention is preferably in the range of 0.1 to 30 mass % in terms of the solid content, and more preferably in the range of 0.2 to 15 mass %.

<(D) Colorant>

The photo-curable composition in the invention may contain (D) colorant.

Especially when the photo-curable composition in the invention is used as an ink composition, colorants having various hues are preferably used.

The colorants that can be used in the photo-curable composition of the invention are not especially restricted, but considering the cases applicable to ink composition, pigments and oil-soluble dyes excellent in weather resistance and color reproducibility are preferably used, and they can be arbitrarily used by selecting from known colorants such as soluble dyes.

Incidentally, it is preferred that the colorants that can be preferably used in the photo-curable composition of the invention do not function as a polymerization inhibitor in polymerization reaction of curing reaction. This is for the purpose of not reducing the sensitivity of curing reaction by actinic radiation.

(D-1) Pigment

The pigments that can be used in the photo-curable composition of the invention are not especially restricted, but, for example, organic or inorganic pigments of the following numbers described in Color Index can be used.

That is, as red or magenta pigments, Pigment Red 3, 5, 19, 22, 31, 38, 43, 48:1, 48:2, 48:3, 48:4, 48:5, 49:1, 53:1, 57:1, 57:2, 58:4, 63:1, 81, 81:1, 81:2, 81:3, 81:4, 88, 104, 108, 112, 122, 123, 144, 146, 149, 166, 168, 169, 170, 177, 178, 179, 184, 185, 208, 216, 226, 257, Pigment Violet 3, 19, 23, 29, 30, 37, 50, 88, Pigment Orange 13, 16, 20, 36, As blue or cyan pigments, Pigment Blue 1, 15, 15:1, 15:2, 15:3, 15:4, 15:6, 16, 17-1, 22, 27, 28, 29, 36, 60, As green pigments, Pigment Green, 7, 26, 36, 50, As yellow pigments, Pigment Yellow, 1, 3, 12, 13, 14, 17, 34, 35, 37, 55, 74, 81, 83, 93, 94, 95, 97, 108, 109, 110, 137, 138, 139, 153, 154, 155, 157, 166, 167, 168, 180, 185, 193, As black pigments, Pigment Black 7, 28, 26, As white pigments, Pigment White 6, 18, 21 can be used according to purpose.

(D-2) Oil-Soluble Dye

Oil-soluble dyes that can be used in the invention will be described below.

Oil-soluble dyes that can be used in the invention mean dyes substantially insoluble in water. Specifically, oil-soluble dyes indicate dyes whose solubility in water at 25° C. (the mass of a dye that is soluble in 100 g of water) is 1 g or lower, preferably 0.5 g or lower, and more preferably 0.1 g or lower. Accordingly, oil-soluble dyes mean what are called water-insoluble pigments and oil-soluble dyestuffs, and oil-soluble dyestuffs are preferred of these colorants.

In the invention, oil-soluble dyes may be used by one kind alone, or several kinds of oil-soluble dyes may be used as mixture. Further, colorants such as other water-soluble dyes, disperse dyes and pigments may be contained so long as the advantage of the invention is not hindered if necessary.

Of the oil-soluble dyes that can be used in the invention, arbitrary dyes can be used as yellow dyes. Yellow dyes include arylazo or heterylazo dyes having, for example, phenols, naphthols, anilines, pyrazolones, pyridones, or an open chain active methylene compound as a coupling component; azomethine dyes having, for example, an open chain active methylene compound as a coupling component; methine dyes such as benzylidene dyes and monomethine oxonol dyes; and quinone dyes such as naphthoquinone dyes and anthraquinone dyes are exemplified, and as dye kinds other than these dyes, quinophthalone dyes, nitro•nitroso dyes, acridine dyes, and acridinone dyes can be exemplified.

Of the oil-soluble dyes that can be used in the invention, arbitrary dyes can be used as magenta dyes. Magenta dyes include arylazo or heterylazo dyes having, for example, phenols, naphthols, or anilines as a coupling component; azomethine dyes having, for example, pyrazolones or pyrazolotriazoles as a coupling component; methine dyes such as arylidene dyes, styryl dyes, merocyanine dyes, and oxonol dyes; carbonium dyes such as diphenylmethane dyes, triphenylmethane dyes, and xanthene dyes; quinone dyes such as naphthoquinone, anthraquinone, and anthrapyridone; and condensed polycyclic dyes such as dioxazine dyes.

Of the oil-soluble dyes that can be used in the invention, arbitrary dyes can be used as cyan dyes. Cyan dyes include as indoaniline dyes, indophenol dyes, and azomethine dye having pyrrotriazole as a coupling component; polymethine dyes such as cyanine dyes, oxonol dyes, and merocyanine dyes; carbonium dyes such as diphenylmethane dyes, triphenylmethane dyes, and xanthene dyes; phthalocyanine dyes; anthraquinone dyes; arylazo or heterylazo dyes having, for example, phenols, naphthols, or anilines as a coupling component; and indigo•thioindigo dyes.

Each of the above dyes may be the ones developing each of yellow, magenta and cyan colors only after the chromophores partly dissociate. In that case, counter cations may be either inorganic cations such as alkali metals and ammonium or organic cations such as pyridinium and quaternary ammonium salts. Alternatively, counter cations may also be polymer cations having those as partial structures.

Although not limitative, preferred specific examples include, e.g., C.I. Solvent Black 3, 7, 27, 29 and 34; C.I. Solvent Yellow 14, 16, 19, 29, 30, 56, 82, 93 and 162; C.I. Solvent Red 1, 3, 8, 18, 24, 27, 43, 49, 51, 72, 73, 109, 122, 132 and 218; C.I. Solvent Violet 3; C.I. Solvent Blue 2, 11, 25, 35, 38, 67 and 70; C.I. Solvent Green 3 and 7; and C.I. Solvent Orange 2. Of these, the especially preferred are Nubian Black PC-0850, Oil Black HBB, Oil Yellow 129, Oil Yellow 105, Oil Pink 312, Oil Red 5B, Oil Scarlet 308, Vali Fast Blue 2606, Oil Blue BOS (manufactured by Orient Chemical Industries, Ltd.), Aizen Spilon Blue GNH (manufactured by Hodogaya Chemical Co., Ltd.), Neopen Yellow 075, Neopen Mazenta SE1378, Neopen Blue 808, Neopen Blue FF4012, and Neopen Cyan FF4238 (manufactured by BASF Japan Ltd.).

Further, in the invention, disperse dyes can also be used within the range of capable of being dissolved in a water-immiscible organic solvent.

The specific examples thereof include C.I. Disperse Yellow 5, 42, 54, 64, 79, 82, 83, 93, 99, 100, 119, 122, 124, 126, 160, 184:1, 186, 198, 199, 201, 204, 224, and 237; C.I. Disperse Orange 13, 29, 31:1, 33, 49, 54, 55, 66, 73, 118, 119, and 163; C.I. Disperse Red 54, 60, 72, 73, 86, 88, 91, 92, 93, 111, 126, 127, 134, 135, 143, 145, 152, 153, 154, 159, 164, 167:1, 177, 181, 204, 206, 207, 221, 239, 240, 258, 277, 278, 283, 311, 323, 343, 348, 356, and 362; C.I. Disperse Violet 33; C.I. Disperse Blue 56, 60, 73, 87, 113, 128, 143, 148, 154, 158, 165, 165:1, 165:2, 176, 183, 185, 197, 198, 201, 214, 224, 225, 257, 266, 267, 287, 354, 358, 365, and 368; and C.I. Disperse Green 6:1 and 9.

As preferred oil-soluble dyes, an azo or azomethine dye represented by the following formula (i) or (ii) can be exemplified. The dye represented by formula (ii) is known as a dye generated from a coupler and a developing agent by oxidation in a photographic material.

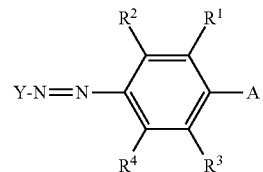

Formula (i)

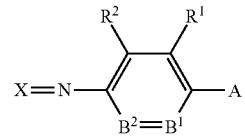

Formula (ii)

In formulae (i) and (ii), each of $R^1$, $R^2$, $R^3$ and $R^4$ independently represents a hydrogen atom, a halogen atom, an aliphatic group, an aromatic group, a heterocyclic group, a cyano group, a hydroxyl group, a nitro group, an amino group, an alkylamino group, an alkoxy group, an aryloxy group, an amido group, an arylamino group, a ureido group, a sulfamoylamino group, an alkylthio group, an arylthio group, an alkoxycarbonylamino group, a sulfonamide group, a carbamoyl group, a sulfamoyl group, a sulfonyl group, an alkoxycarbonyl group, a heterocyclic oxy group, an azo group, an acyloxy group, a carbamoyloxy group, a silyloxy group, an aryloxycarbonyl group, an aryloxycarbonylamino group, an imido group, a heterocyclic thio group, a sulfinyl group, a phosphoryl group, an acyl group, a carboxyl group, or a sulfo group.

In formulae (i) and (ii), of the above substituents, $R^2$ especially preferably represents a hydrogen atom, a halogen atom, an aliphatic group, an alkoxy group, an aryloxy group, an amido group, a ureido group, a sulfamoylamino group, an alkoxycarbonylamino group, or a sulfonamide group.

Further, in the invention, the aliphatic group means an alkyl group, a substituted alkyl group, an alkenyl group, a substituted alkenyl group, an alkynyl group, a substituted alkynyl group, an aralkyl group, and a substituted aralkyl group. These aliphatic groups may have branches or form a ring.

The number of carbon atoms of the aliphatic groups is preferably 1 to 20, and more preferably 1 to 18.

The aryl portion of the aralkyl group and substituted aralkyl group is preferably phenyl or naphthyl, and especially preferably phenyl.

As the examples of the substituents of alkyl portions of the substituted alkyl group, substituted alkenyl group, substituted alkynyl group, and substituted aralkyl group, the substituents exemplified in the description of $R^1$ to $R^4$ can be exemplified.

The examples of the substituents of aryl portions of the substituted aralkyl group are the same as the examples of the substituents of the following substituted aryl group.

Further, in the invention, the aromatic group means an aryl group and a substituted aryl group. The aryl group is preferably a phenyl group or a naphthyl group, and especially preferably a phenyl group.

The aryl portion of the substituted aryl group is the same as the above aryl group.

As the examples of the substituents of the substituted aryl group, the substituents exemplified in the description of $R^1$ to $R^4$ can be exemplified.

In formulae (i) and (ii), A represents —$NR^5R^6$ or a hydroxyl group. Each of $R^5$ and $R^6$ independently represents a hydrogen atom, an aliphatic group, an aromatic group, or a heterocyclic group. $R^5$ and $R^6$ may be bonded to each other to form a ring.

A preferably represents —$NR^5R^6$. Each of $R^5$ and $R^6$ more preferably independently represents a hydrogen atom, an alkyl group, a substituted alkyl group, an aryl group, or a substituted aryl group, and most preferably a hydrogen atom, an alkyl group having 1 to 18 carbon atoms, or a substituted alkyl group having 1 to 18 carbon atoms.

In formula (ii), $B^1$ represents =$C(R^3)$— or =N—, and $B^2$ represents —$C(R^4)$= or —N=. The case where $B^1$ and $B^2$ do not represent —N= at the same time is preferred, and the case where $B^1$ represents =$C(R^3)$—, and $B^2$ represents —$C(R^4)$= is more preferred.

Further, in formulae (i) and (ii), any of $R^1$ and $R^5$, $R^3$ and $R^6$, and $R^1$ and $R^2$ may be bonded to each other to form an aromatic or heterocyclic ring.

In formula (i), Y represents an unsaturated heterocyclic group. Y preferably represents a 5- or 6-membered unsaturated heterocyclic group. The heterocyclic ring may be condensed with an aliphatic ring, an aromatic ring or other heterocyclic ring. The examples of the hetero atoms of the heterocyclic group include N, O and S.

The unsaturated heterocyclic group is preferably a monovalent group obtained by removing one hydrogen atom from a heterocyclic ring such as a pyrazole ring, an imidazole ring, a thiazole ring, an isothiazole ring, a thiadiazole ring, a thiophene ring, a benzothiazole ring, a benzoxazole ring, a benzisothiazole ring, a pyrimidine ring, a pyridine ring, and a quinoline ring. The unsaturated heterocyclic group may have a substituent such as described above in $R^1$ to $R^4$.

In formula (ii), X represents a residue of a color photographic coupler. As the residue of the color photographic coupler, the following couplers are preferably exemplified.

Yellow couplers: U.S. Pat. Nos. 3,933,501, 4,022,620, 4,326,024, 4,401,752, 4,248,961, Japanese National Phase Publication (JP-B) No. 58-10739, British Patent Nos. 1,425, 020, 1,476,760, U.S. Pat. Nos. 3,973,968, 4,314,023, 4,511, 649, couplers represented by formula (I) or (II) of EP-A No. 249,473, 502,424, couplers represented by formula (1) or (2) (in particular Y-28 on page 18) of EP-A No. 513,496, the coupler represented by formula (I) of claim 1 of EP-A No. 568,037, the coupler represented by formula (I), lines 45-55, column 1 of U.S. Pat. No. 5,066,576, the coupler represented by formula (I) in paragraph [0008] of JP-A No. 4-274425, the coupler described in claim 1, page 40 of EP-A No. 498,381 (in particular D-35 on page 18), the couplers represented by formula (Y) on page 4 of EP-A No. 447,969 (in particular, Y-1 (p. 17), Y-54 (p. 41)), and the couplers represented by any of formulae (II) to (IV), lines 36-58, column 7 of U.S. Pat. No. 4,476,219 (in particular, II-17, 19 (column 17), 11-24 (column 19)).

Magenta couplers: U.S. Pat. Nos. 4,310,619, 4,351,897, EP No. 73,636, U.S. Pat. Nos. 3,061,432, 3,725,067, Research Disclosure, Nos. 24220 (June, 1984), 24230 (June, 1984), JP-A Nos. 60-33552, 60-43659, 61-72238, 60-35730, 55-118034, 60-185951, U.S. Pat. Nos. 4,500,630, 4,540,654, 4,556,630, WO 88/04795, JP-A No. 3-39737 (line 57 (page 11, the right lower part), line 68 (page 12, the right lower part), line 77 (page 13, the right lower part)), [A-4]-63 (page 134), [A-4]-73, -75 (page 139) of EP No. 456,257, M-4, -6 (page 26), M-7 (page 27) of EP No. 486,965, M-45 (page 19) of EP-A No. 571,959, M-1 (page 6) of JP-A No. 5-204106, M-22 in paragraph [0237] of JP-A No. 4-362631, and U.S. Pat. Nos. 3,061,432, and 3,725,067.

Cyan coupler: U.S. Pat. Nos. 4,052,212, 4,146,396, 4,228, 233, 4,296,200, EP No. 73,636, CX-1, 3, 4, 5, 11, 12, 14, 15 (pages 14-16) of JP-A No. 4-204843; C-7, 10 (page 35), 34, 35 (page 37), (I-1), (I-17) (pages 42-43) of JP-A No. 4-43345; and the coupler represented by formula (Ia) or (Ib) in claim 1 of JP-A No. 6-67385.

In addition, the couplers disclosed on page 91 of JP-A No. 62-215272, pages 3 and 30 of JP-A No. 2-33144, and pages 4, 5, 45 and 47 of EP-A No. 355,660 are also useful.

Of the oil-soluble dyes represented by formula (i), the dyes represented by the following formula (iii) are especially preferred as magenta dyes.

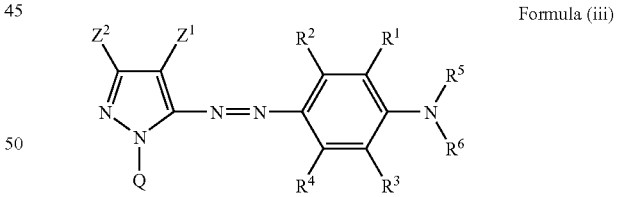

Formula (iii)

In formula (iii), $Z^1$ represents an electron attracting group having Hammett's substituent constant σp value of 0.20 or more. $Z^1$ preferably represents an electron attracting group having Hammett's substituent constant σp value of 0.30 or more and 1.0 or less. As preferred specific substituents, the later-described electron attracting substituents can be exemplified. Of the substituents, an acyl group having 2 to 12 carbon atoms, an alkyloxycarbonyl group having 2 to 12 carbon atoms, a nitro group, a cyano group, an alkylsulfonyl group having 1 to 12 carbon atoms, an arylsulfonyl group having 6 to 18 carbon atoms, a carbamoyl group having 1 to 12 carbon atoms, and a halogenated alkyl group having 1 to 12 carbon atoms are preferred, a cyano group, an alkylsulfonyl group having 1 to 12 carbon atoms, and an arylsulfonyl group having 6 to 18 carbon atoms are especially preferred, and a cyano group is most preferred.

In formula (iii), $Z^2$ represents a hydrogen atom, an aliphatic group or an aromatic group.

In formula (iii), $R^1$ to $R^6$ have the same meanings as those in $R^1$ to $R^6$ in formula (i), and the preferred ranges are also the same.

In formula (iii), Q represents a hydrogen atom, an aliphatic group, an aromatic group, or a heterocyclic group, and preferably represents a group selected from a nonmetal atomic group necessary to form a 5- to 8-membered ring. Above all, an aromatic group or a heterocyclic group is preferred. The 5- to 8-membered ring may be substituted, may be a saturated ring, or may have an unsaturated bond. Preferred nonmetal atoms include a nitrogen atom, an oxygen atom, a sulfur atom, and a carbon atom.

The specific examples of such ring structures include, e.g., a benzene ring, a cyclopentane ring, a cyclohexane ring, a cycloheptane ring, a cyclooctane ring, a cyclohexene ring, a pyridine ring, a pyrimidine ring, a pyrazine ring, a pyridazine ring, a triazine ring, an imidazole ring, a benzimidazole ring, an oxazole ring, a benzoxazole ring, an oxane ring, a sulforan ring, and a thian ring. When these rings further have a substituent, the groups represented by the substituents $R^1$ to $R^6$ in formula (i) can be exemplified as the examples of the substituents.

The preferred structure of the compound represented by formula (iii) is disclosed in JP-A No. 2001-335714.

Of the dyes represented by formula (ii), the dyes represented by the following formula (iv) are especially preferred as magenta dyes.

Formula (iv)

In formula (iv), G represents a hydrogen atom, an aliphatic group, an aromatic group, a heterocyclic group, a cyano group, an alkoxy group, an aryloxy group, an alkylthio group, an arylthio group, an ester group, an amino group, a carbamoyl group, a sulfonyl group, a sulfamoyl group, a ureido group, a urethan group, an acyl group, an amido group, or a sulfonamide group.

In formula (iv), $R^1$, $R^2$, A, $B^1$ and $B^2$ have the same meanings as $R^1$, $R^2$, A, $B^1$ and $B^2$ in formula (ii), and preferred ranges of them are also the same.

In formula (iv), L represents an atomic group to form a 5- or 6-membered nitrogen-containing heterocyclic ring which may be substituted with at least one of an aliphatic group, an aromatic group, a heterocyclic group, a cyano group, an alkoxy group, an aryloxy group, an alkylthio group, an arylthio group, an ester group, an amino group, a carbamoyl group, a sulfonyl group, a sulfamoyl group, a ureido group, a urethane group, an acyl group, an amido group, and a sulfonamido group, and the nitrogen-containing heterocyclic ring may further form a condensed ring with other ring.

In the compound represented by formula (iv), A preferably represents —$NR^5R^6$, and L preferably represents a 5-membered nitrogen-containing heterocyclic ring. The examples of the 5-membered nitrogen-containing heterocyclic ring include an imidazole ring, a triazole ring and a tellurazole ring.

Of the dyes represented by formula (i) or (ii), exemplified compounds of magenta dyes (M-0-6 and a-21-25) are shown below, but these compounds are shown for explaining the invention in detail and the invention is not restricted thereto. Note that, n represents that the hydrocarbon is a normal structure and t represents that the hydrocarbon is a tertiary structure.

(M-0)

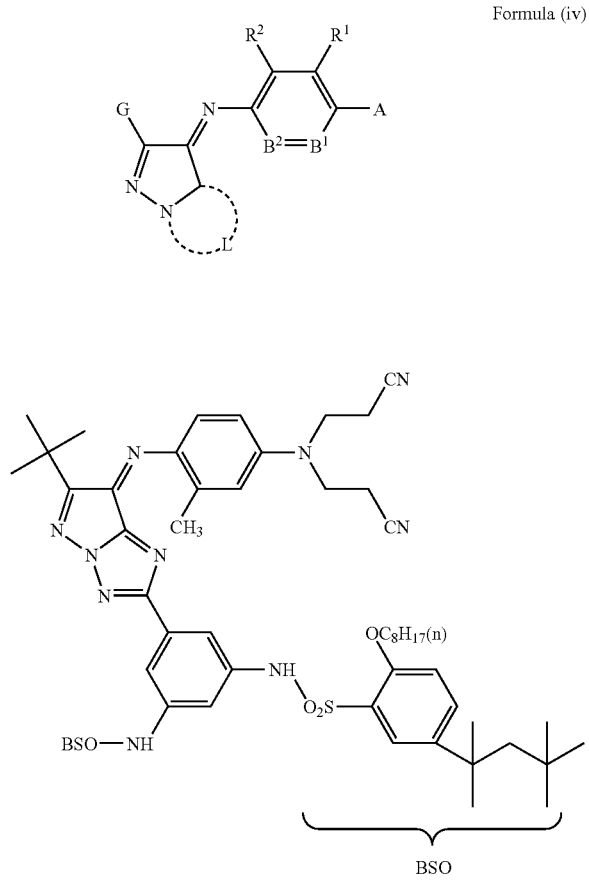

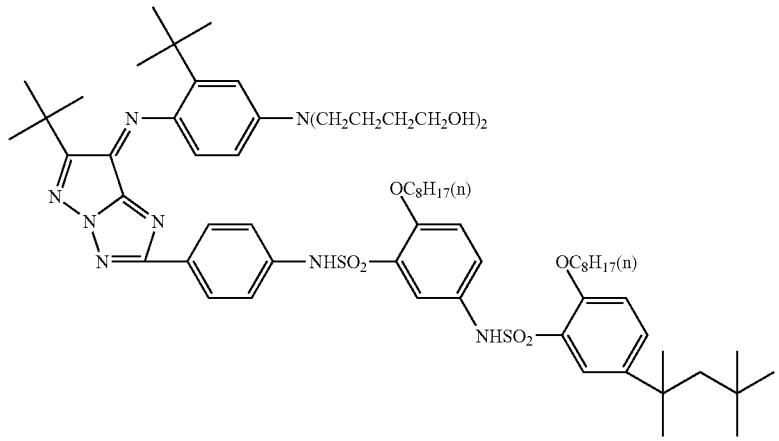
(M-1)
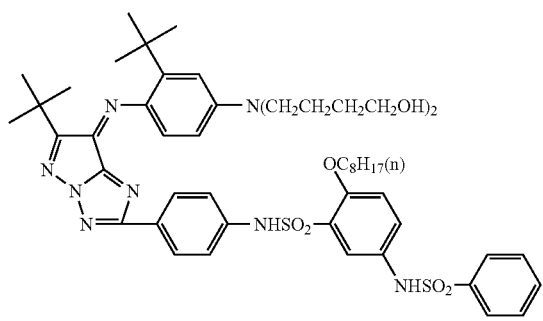
(M-2)
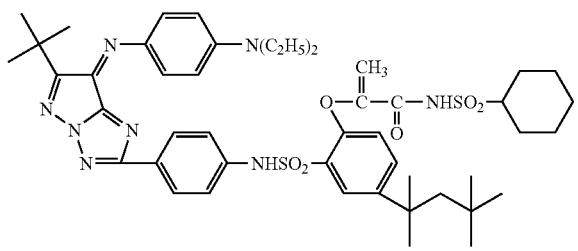
(M-3)
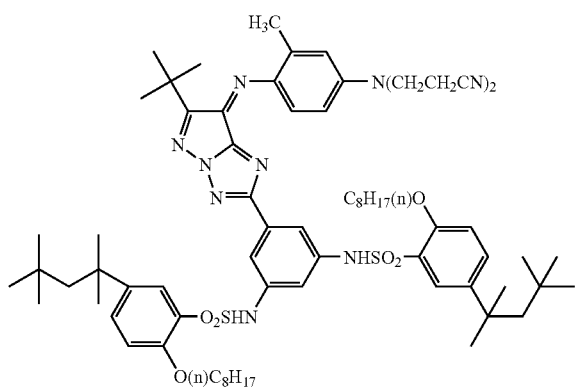
(M-4)
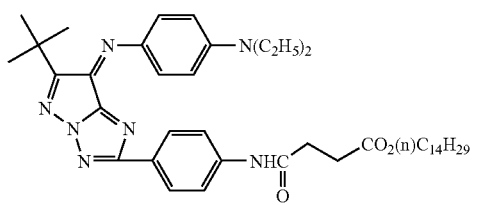
(M-5)
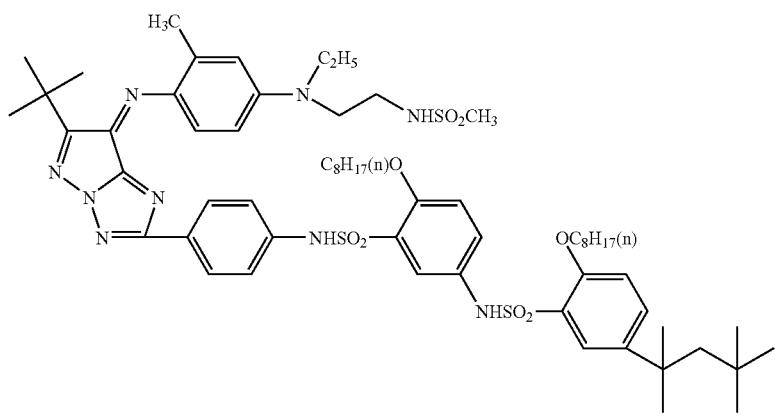
(M-6)

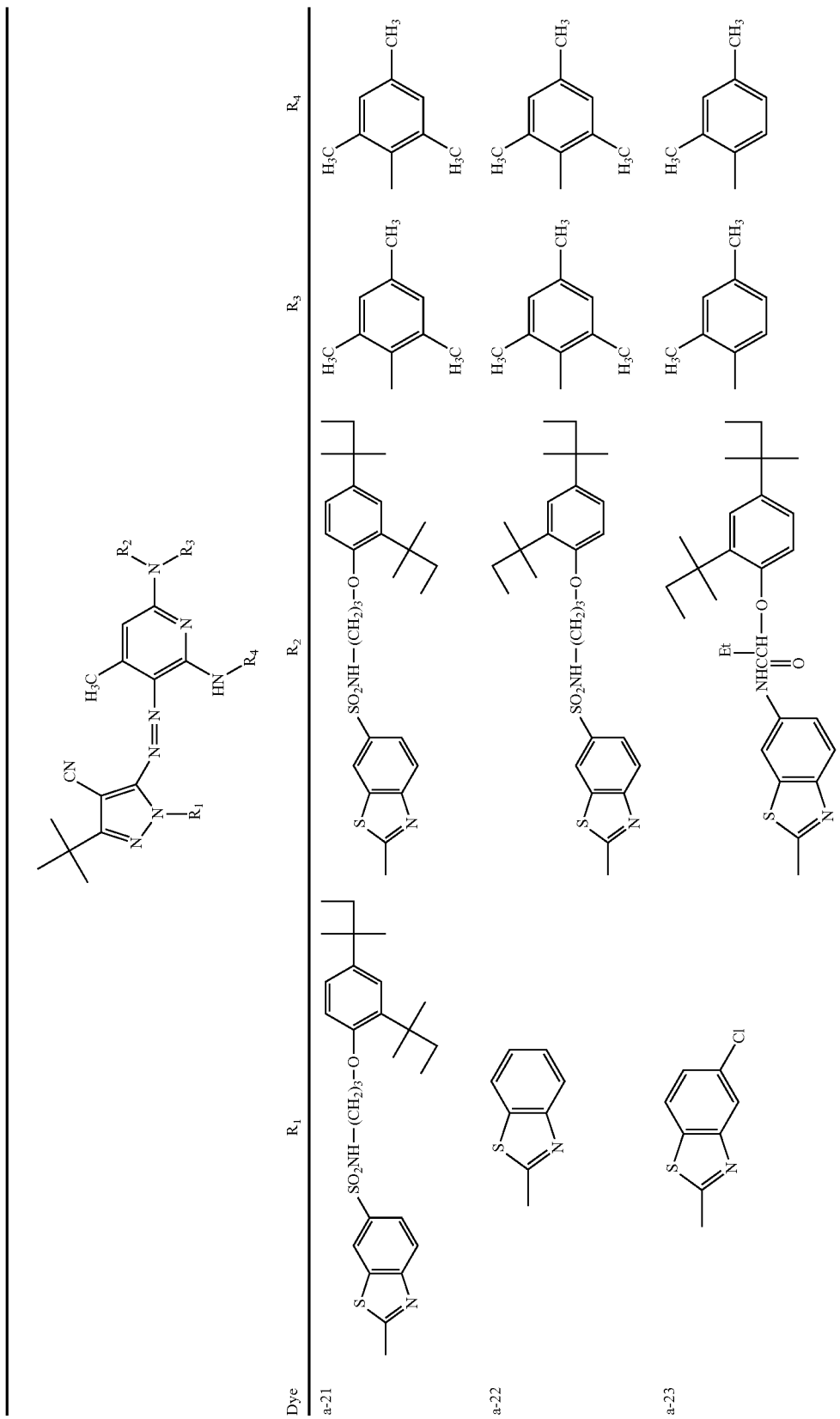

-continued
| Dye | R1 | R2 | R3 | R4 |
|---|---|---|---|---|
| a-24 | 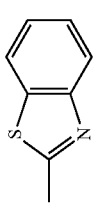 | 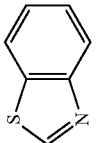 | 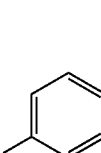 |  |
| a-25 | 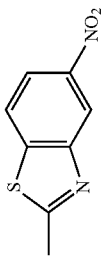 |  | 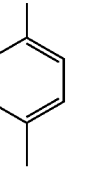 | 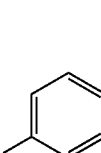 |

As other colorants usable in the invention, those disclosed in JP-A Nos. 2001-240763, 2001-181549, and 2001-335714 are exemplified, but the invention is not restricted thereto.

The compounds represented by formula (iii) can be synthesized according to the methods disclosed in JP-A Nos. 2001-335714 and 55-161856.

The compounds represented by formula (iv) can be synthesized according to the methods disclosed in JP-A No. 4-126772, JP-B No. 7-94180, and JP-A No. 2001-240763.

Of the dyes represented by formula (ii), as the cyan dye, a pyrrolotriazole azomethine dye represented by the following formula (v) can be especially preferably used.

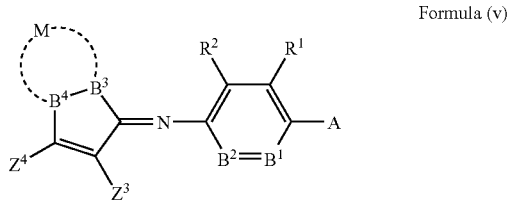

Formula (v)

In formula (v), A, $R^1$, $R^2$, $B^1$ and $B^2$ have the same meanings as A, $R^1$, $R^2$, $B^1$ and $B^2$ in formula (ii), and preferred ranges of them are also the same.

In formula (v), each of $Z^3$ and $Z^4$ independently has the same meaning as G in formula (iv), and $Z^3$ and $Z^4$ may be bonded to each other to form a ring structure.

Those in which $Z^3$ is an electron attracting group having Hammett's substituent constant σp value of 0.30 or more are sharp in absorption and more preferred. Further, an electron attracting group having Hammett's substituent constant σp value of 0.45 or more is more preferred, and an electron attracting group having Hammett's substituent constant σp value of 0.60 or more is most preferred. Those having the sum total of an electron attracting group having Hammett's substituent constant σp values of $Z^3$ and $Z^4$ of 0.70 or more show excellent hue of a cyan color and still yet preferred.

In formula (v), M represents an atomic group to form a 1,2,4-triazole ring condensed to the 5-membered ring in formula (v), and either one of the two atoms $B^3$ and $B^4$ of the condensed parts of the 5-membered ring is a nitrogen atom and the other is a carbon atom.

The compound represented by formula (v) is preferably used as a cyan dye, but it can also be used as a magenta dye.

Hammett's substituent constant σp value used in the specification will be described. Hammett's rule is a rule of thumb lectured by L. P. Hammett in 1935 to quantitatively discuss the influence of substituents on the reaction or equilibrium of benzene derivatives, and the appropriateness of which is now widely recognized. In the substituent constant required of Hammett's rule are σp value and σm value, and these values can be found in many ordinary publications, for example, these are described in detail in J. A. Dean compiled, "Lange's Handbook of Chemistry", Ed. 12 (1979), McGraw Hill, and "Kagaku no Ryoiki (Region of Chemistry)", Extra Edition, Vol. 122, pp. 96-103 (1979), Nankodo Co., Ltd. Incidentally, in the invention, each substituent is limited or explained by Hammett's substituent constant σp value, but this does not mean to be limited to solely the substituents having known values as found in the above publications. A substituent that is supposed to be included within the range if measured in conformity with Hammett's rule is also included of course, even when the value thereof is unknown in the publications. Further, those not benzene derivatives are also included in formulae (i) to (v), but σp value is used as an index showing the electronic effect of the substituent irrespective of substitution position. In the invention, σp value is used in such a meaning.

As electron attracting groups having Hammett's substituent constant σp value of 0.60 or more, a cyano group, a nitro group, an alkylsulfonyl group (e.g., a methanesulfonyl group), and an arylsulfonyl group (e.g., a benzenesulfonyl group) can be exemplified.

As electron attracting groups having Hammett's substituent constant σp value of 0.45 or more, in addition to the above, an acyl group (e.g., an acetyl group), an alkoxycarbonyl group (e.g., a dodecyloxycarbonyl group), an aryloxycarbonyl group (e.g., an m-chlorophenoxycarbonyl group), an alkylsulfinyl group (e.g., an n-propylsulfinyl group), an arylsulfinyl group (e.g., a phenylsulfinyl group), a sulfamoyl group (e.g., an N-ethylsulfamoyl group, an N,N-dimethylsulfamoyl group), and a halogenated alkyl group (e.g., a trifluoromethyl group) can be exemplified.

As electron attracting groups having Hammett's substituent constant σp value of 0.30 or more, in addition to the above, an acyloxy group (e.g., an acetoxy group), a carbamoyl group (e.g., an N-ethylcarbamoyl group, an N,N-dibutylcarbamoyl group), a halogenated alkoxy group (e.g., a trifluoromethyloxy group), a halogenated aryloxy group (e.g., pentafluorophenyloxy group), a sulfonyloxy group (e.g., a methylsulfonyloxy group), a halogenated alkylthio group (e.g., a difluoromethylthio group), an aryloxy group substituted with two or more electron attracting groups having σp value of 0.15 or more (e.g., a 2,4-dinitrophenyl group, a pentachlorophenyl group), and a heterocyclic group (e.g., a 2-benzoxazolyl group, a 2-benzothiazolyl group, a 1-phenyl-2-benzimidazolyl group) can be exemplified.

As the specific examples of electron attracting groups having σp value of 0.20 or more, a halogen atom and the like can be exemplified, in addition to the above.

An oil-soluble dye represented by the following formula (A-I) can be preferably used in the invention.

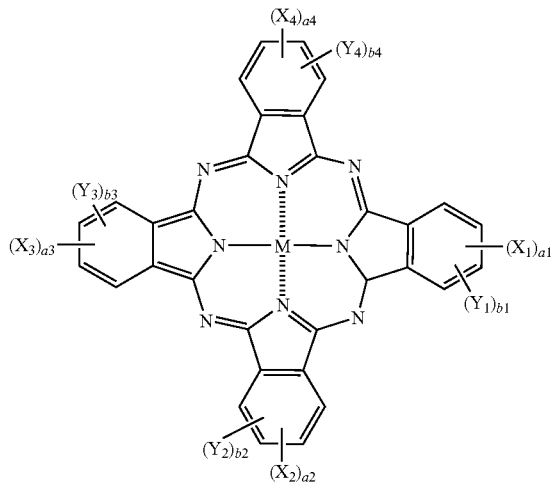

Formula (A-I)

In formula (A-I), each of $X_1$, $X_2$, $X_3$ and $X_4$ independently represents a group selected from —SO-Z, —$SO_2$-Z, —$SO_2NR_1R_2$, —$CONR_1R_2$, —$CO_2R_1$ and a sulfo group. Z represents a substituted or unsubstituted alkyl group, a substituted or unsubstituted cycloalkyl group, a substituted or unsubstituted alkenyl group, a substituted or unsubstituted aralkyl group, a substituted or unsubstituted aryl group, or a substituted or unsubstituted heterocyclic group. Each of $R_1$ and $R_2$ independently represents a hydrogen atom, a substituted or unsubstituted alkyl group, a substituted or unsubstituted cycloalkyl group, a substituted or unsubstituted alkenyl group, a substituted or unsubstituted aralkyl group, a substituted or unsubstituted aryl group, or a substituted or unsubstituted heterocyclic group, provided that $R_1$ and $R_2$ do not represent hydrogen atoms at the same time. M represents a hydrogen atom, a metal element, a metal oxide, a metal hydroxide, or a metal halide. Each of $Y_1$, $Y_2$, $Y_3$ and $Y_4$ independently represents a hydrogen atom or a monovalent substituent. a1, a2, a3, a4, b1, b2, b3 and b4 represent the number of $X_1$, $X_2$, $X_3$, $X_4$, $Y_1$, $Y_2$, $Y_3$ and $Y_4$, respectively, and each is independently an integer of 0 to 4, provided that the sum total of a1 to a4 is 2 or more. Of the oil-soluble dyes, an oil-soluble dye represented by the following formula (A-II) can be especially preferably used.

Formula (A-II)

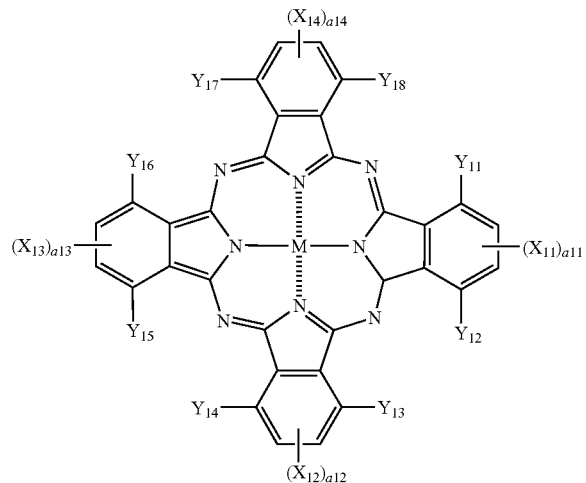

In formula (A-II), $X_{11}$ to $X_{14}$, $Y_{11}$ to $Y_{18}$, and M have the same meanings as $X_1$ to $X_4$, $Y_1$ to $Y_4$, and M of the formula (A-I). Each of a11 to a14 independently represents an integer of 1 or 2.

As the specific example of (A-II), an exemplified compound (AII-17) is shown below, which is to explain the invention in detail, so that the invention is not restricted thereto.

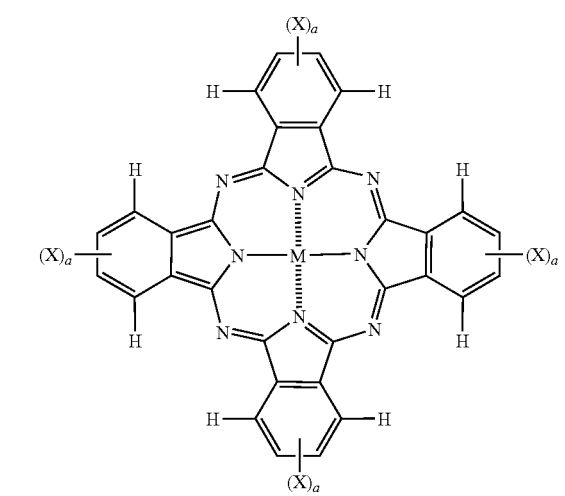

| Compound No. | M | X | a |
|---|---|---|---|
| AII-17 | Cu | —$SO_2$—$(CH_2)_3$—$SO_2NH$—$(CH_2)_3$—O—CH($CH_3$)$CH_3$ | 1 |

In the invention it is preferred to use oil-soluble dyes having oxidation potential of nobler than 1.0 V (SCE). The nobler the oxidation potential, the more preferred is the oil-soluble dye is. The oxidation potential is more preferably nobler than 1.1 V (SCE), and most preferably nobler than 1.2 V (SCE).

The value of oxidation potential (Eox) can easily be measured by those skilled in the art. The measuring method is described, e.g., in P. Delahay, "New Instrumental Methods in Electrochemistry", Interscience Publishers (1954), A. J. Bard et al., "Electrochemical Methods", John Wiley & Sons (1980), and Akira Fujishima et al., "Denki Kagaku Sokuteiho (Electrochemical Measurement Methods)", Gihodo Shuppan Co., Ltd. (1984).

Specifically describing, the oxidation potential is measured by dissolving a test sample in a solvent such as dimethylformamide or acetonitrile containing a support electrolyte such as sodium perchlorate or tetrapropylammonium perchlorate in concentration of $1 \times 10^{-4}$ to $1 \times 10^{-6}$ mol/liter, and approximating an oxidation wave to a straight line when sweeping toward the oxidation side (noble side) by using carbon (GC) as a working electrode and a rotating platinum electrode as the counter electrode by means of cyclic voltammetry or direct current polarographic equipment. The intermediate potential value of a line segment formed by an intersection of the straight line and a residual current/potential straight line and an intersection of the straight line and a saturated current straight line (or an intersection with a straight line parallel to the axis of ordinate passing through the potential peak value) is measured as a value to the SCE (saturated calomel electrode). The value sometimes deviates by of the order of tens of millivolts under the influence of the liquid junction potential, the liquid resistance of the sample solution, and the like. However, the reproducibility of the potential can be ensured by the addition of a standard sample (e.g., hydroquinone). The support electrolyte and the solvent to be used can be appropriately selected according to the oxidation potential and the solubility of the test sample. In connection with the support electrolyte and the solvent that can be used, Akira Fujishima et al., "Electrochemical Measurement Methods", pp. 101-118, Gihodo Shuppan Co., Ltd. (1984) can be referred to.

In the concentration range of the measuring solvent and the sample, the oxidation potential in a non-association state is measured.

The value of Eox represents easiness of electron transfer from the sample to the electrode, and the greater the value (the nobler the oxidation potential), the more difficult is the electron transfer from the sample to the electrode, in other words, the more difficult is it to be oxidized.

When a dye having a low oxidation potential is used, polymerization hindrance by the dye is great and a curing property lowers. When a dye having a noble oxidation potential is used, polymerization is hardly hindered.

The colorant that can be used in the invention is preferably added to a composition and then appropriately dispersed in the composition. For the dispersion of colorants, various dispersers such as a ball mill, a sand mill, an attritor, a roll mill, an agitator, a Henschel mixer, a colloid mill, an ultrasonic homogenizer, a pearl mill, a wet jet mill, and a paint shaker can be used.

It is also possible to use a dispersant at the time of dispersion of colorants. As the dispersants, the kinds are not especially restricted, but it is preferred to use polymer dispersants. As polymer dispersants, for example, Solsperse series manufactured by Zeneca can be exemplified. Further, as auxiliary dispersants, it is also possible to use synergists according to various kinds of pigments. In the invention, these dispersants and auxiliary dispersants are preferably used in an amount of 1 to 50 mass parts per 100 mass parts of the colorant.

Colorants may be directly added to the photo-curable composition in the invention, but for the purpose of improving dispersibility, they may be added in advance to a solvent or a dispersion medium such as a polymerizable compound for use in the invention. In the invention, for the purpose of avoiding the problem of solvent resistance deterioration when the solvent remains in a cured image and the problem of VOC (Volatile Organic Compound) of the residual solvent, the colorant is preferably added to a polymerizable compound. As a polymerizable compound to be used, it is preferred to select a monomer having the lowest viscosity in view of dispersion suitability.

In the invention, it is preferred for the average particle size of the colorant particles to be in the range of 0.005 to 0.5 µm, more preferably 0.01 to 0.45 µm, and still more preferably 0.015 to 0.3 µm. Further, the largest particle size of the colorant particles is preferably 0.3 to 10 µm, and more preferably 0.3 to 3 µm. In order to make the largest particle size as above, it is preferred to select the colorant, the dispersant and the dispersion medium, and set the dispersion condition and filtration condition. By such particle size control, when the photo-curable composition of the invention is applied to an ink composition for inkjet recording, clogging of head nozzles can be suppressed, preservation stability and transparency of the ink and sensitivity for curing can be preferably maintained.

These colorants are added to the photo-curable composition in terms of solids content of preferably 1 to 30 mass %, and more preferably 2 to 25 mass %.

In addition to the above components, the photo-curable composition of the invention may contain other components in combination for the purpose of the improvement of physical properties so long as they do not impair the advantage of the invention.

These optional components will be described below.

In order to prevent sensitivity reduction due to shading effect in the case where the colorants are used, the photo-curable composition of the invention may be a hybrid type radical/cationic composition using a radical polymerizable compound and a radical polymerization initiator in combination in addition to the combination of cationic polymerizable compound and the onium salt.

<Radical Polymerizable Compound>

The photo-curable composition in the invention can contain a radical polymerizable compound.

The radical polymerizable compound is a radical polymerizable organic compound that is subjected to polymerization reaction or crosslinking reaction upon irradiation with actinic radiation in the presence of a radical polymerization initiator, and preferably has at least one ethylenically unsaturated double bond in one molecule.

As the radical polymerizable compound, for example, the compounds for use in a photo-polymerizable composition as disclosed in JP-A No. 7-159983, JP-B No. 7-31399, JP-A Nos. 8-224982, 10-863 and 9-80675 are known.

As the radical polymerizable compounds, for example, an acrylate compound, a methacrylate compound, an allylurethane compound, an unsaturated polyester compound, and a styrene compound are preferably exemplified.

Of these radical polymerizable compounds, compounds having a (meth)acryl group are easily synthesizable, available and handlable, and so preferred. Specifically, for example, epoxy(meth)acrylate, urethane(meth)acrylate, polyester (meth)acrylate, polyether(meth)acrylate, and (meth)acrylates of alcohols are exemplified.

Incidentally, (meth)acrylic acid indicates acrylic acid, methacrylic acid, or the mixture thereof, and (meth)acrylate indicates acrylate, methacrylate, or the mixture thereof.

Here, epoxy(meth)acrylate is (meth)acrylate obtained by the reaction of conventionally known aromatic epoxy resin, alicyclic epoxy resin, or aliphatic epoxy resin with (meth) acrylic acid.

Of these epoxy acrylates, acrylate of aromatic epoxy resin is especially preferred, which is (meth)acrylate obtained by the reaction of polyhydric phenol having at least one aromatic nucleus, or polyglycidyl ether of alkylene oxide adduct thereof with (meth)acrylic acid. For example, (meth)acrylate obtained by the reaction of bisphenol A, or glycidyl ether obtained by the reaction of alkylene oxide adduct of bisphenol A and epichlorohydrin with (meth)acrylic acid, and (meth)acrylate obtained by the reaction of epoxy novolak resin with (meth)acrylic acid are exemplified.

Especially preferred urethane(meth)acrylates are (meth) acrylates obtained by the reaction of one or two or more of hydroxyl group-containing polyester or hydroxyl group-containing polyether with hydroxyl group-containing (meth) acrylate and isocyanates, and (meth)acrylate obtained by the reaction of hydroxyl group-containing (meth)acrylate with isocyanates.

The hydroxyl group-containing polyesters preferably used for obtaining the urethane(meth)acrylate are hydroxyl group-containing polyesters that can be obtained by the reaction of one or more polyhydric alcohols with one or more polybasic acids.

As the polyhydric alcohols, e.g., 1,3-butanediol, 1,4-butanediol, 1,6-hexanediol, diethylene glycol, triethylene glycol, neopentyl glycol, polyethylene glycol, polypropylene glycol, polybutylene glycol, trimethylolpropane, glycerol, pentaerythritol, and dipentaerythritol are exemplified. As the polybasic acids, e.g., adipic acid, terephthalic acid, phthalic anhydride, and trimellitic acid are exemplified.

The hydroxyl group-containing polyethers preferably used for obtaining the urethane(meth)acrylate are hydroxyl group-containing polyethers that can be obtained by the addition of one or more alkylene oxides to polyhydric alcohols.

As the polyhydric alcohols, the same compounds as described above can be exemplified. As the alkylene oxides, ethylene oxide, propylene oxide, and butylene oxide are exemplified.

The hydroxyl group-containing (meth)acrylates preferably used for obtaining the urethane(meth)acrylate are hydroxyl group-containing (meth)acrylates that can be obtained by the esterification reaction of polyhydric alcohol with (meth) acrylic acid.

As the polyhydric alcohols, the same compounds as described above can be exemplified.

Of the hydroxyl group-containing (meth)acrylates, hydroxyl group-containing (meth)acrylate obtained by the esterification reaction of divalent alcohol with (meth)acrylic acid is especially preferred, and specifically, e.g., 2-hydroxyethyl(meth)acrylate is exemplified.

The isocyanates preferably used for obtaining the urethane (meth)acrylate are compounds having at least one isocyanate group in the molecule, and divalent isocyanate compounds, e.g., tolylene diisocyanate, hexamethylene diisocyanate, and isophorone diisocyanate are especially preferred.

The preferred polyester(meth)acrylates are polyester (meth)acrylates that can be obtained by the reaction of hydroxyl group-containing polyester with (meth)acrylic acid.

The hydroxyl group-containing polyesters preferably used for obtaining the polyester(meth)acrylates are hydroxyl group-containing polyesters that can be obtained by the esterification reaction of one or more polyhydric alcohols with one or more monobasic acids or polybasic acids.

As the polyhydric alcohols, the same compounds as described above can be exemplified. As the monobasic acids, e.g., formic acid, acetic acid, butyric acid and benzoic acid are exemplified. As the polybasic acids, e.g., adipic acid, terephthalic acid, phthalic anhydride, and trimellitic acid are exemplified.

The preferred polyether(meth)acrylates are polyether (meth)acrylates that can be obtained by the reaction of hydroxyl group-containing polyether with (meth)acrylic acid.

The hydroxyl group-containing polyethers preferably used for obtaining the polyether(meth)acrylates are hydroxyl group-containing polyethers that can be obtained by adding one or more alkylene oxides to polyhydric alcohols.

As the polyhydric alcohols, the same compounds as described above can be exemplified. As the alkylene oxides, ethylene oxide, propylene oxide, and butylenes oxide are exemplified.

The preferred (meth)acrylates of alcohols are (meth)acrylates that can be obtained by the reaction of aromatic or aliphatic alcohol having at least one hydroxyl group in the molecule, and alkylene oxide adduct thereof, with (meth) acrylic acid.

Specifically, for example, 2-ethylhexyl(meth)acrylate, 2-hydroxyethyl(meth)acrylate, 2-hydroxypropyl(meth)acrylate, isoamyl(meth)acrylate, lauryl(meth)acrylate, stearyl (meth)acrylate, isooctyl(meth)acrylate, tetrahydrofurfuryl (meth)acrylate, isobonyl(meth)acrylate, benzyl(meth) acrylate, 1,3-butanediol di(meth)acrylate, 1,4-butanediol di(meth)acrylate, 1,6-hexanediol di(meth)acrylate, diethylene glycol di(meth)acrylate, triethylene glycol di(meth)acrylate, neopentyl glycol di(meth)acrylate, polyethylene glycol di(meth)acrylate, polypropylene glycol di(meth)acrylate, trimethylolpropane tri(meth)acrylate, ethylene oxide-modified trimethylolpropane tri(meth)acrylate, propylene oxide-modified trimethylolpropane tri(meth)acrylate, pentaerythritol tetra(meth)acrylate, dipentaerythritol hexa(meth)acrylate, and ε-caprolactone-modified dipentaerythritol hexa(meth) acrylate are exemplified.

These radical polymerizable compounds may be used by one kind alone, or two or more kinds may be blended according to desired performance.

It is preferred that 50 mass parts or more of 100 mass parts of the radical polymerizable compound be a compound having a (meth)acryl group in the molecule.

The radical polymerizable compound is preferably contained in the photo-curable composition of the invention in the range of 5 to 50 mass %, and more preferably in the range of 10 to 30 mass % based on total solid content.

<Radical Polymerization Initiator>

The photo-curable composition of the invention can contain a radical polymerization initiator.

Further, when the radical polymerizable compound is used in the photo-curable composition of the invention, it is preferred to contain a radical polymerization initiator.

The radical polymerization initiator is a compound capable of initiating radical polymerization upon irradiation of energy. The radical polymerization initiators that can be preferably used in the invention include (a) aromatic ketones, (b) organic peroxides, (c) thio compounds, (d) hexaarylbiimidazole compounds, (e) keto oxime ester compounds, (f) borate compounds, (g) azinium compounds, (h) metallocene compounds, (i) active ester compounds, (j) compounds having a carbon-halogen bond, and (k) alkylamine compounds. As radical polymerization initiators, these compounds (a) to (k) may be used alone or in combination.

The radical polymerization initiator can be blended preferably in the range of 0.05 to 20 mass % based on the radical polymerizable compound, and more preferably 0.1 to 10 mass %. When radical polymerization initiator is used in the above range, the composition can be sufficiently cured and a cured product having sufficient strength can be obtained and so preferred.

<Hydroxyl Group-containing Organic Compound>

Although not essential but if necessary, an organic compound having two or more hydroxyl groups in the molecule (hereinafter referred to as a hydroxyl group-containing organic compound) can be blended with the photo-curable composition of the invention.

By blending the organic compound having two or more hydroxyl groups in the molecule (the hydroxyl group-containing organic compound), e.g., a polyhydric alcohol, a hydroxyl group-containing polyether, a hydroxyl group-containing polyester, or a polyhydric phenol, with the photo-curable composition of the invention, the mechanical strength of a cured film can be heightened.

As the examples of polyhydric alcohol that is one of hydroxyl group-containing organic compounds, ethylene glycol, propylene glycol, neopentyl glycol, trimethylolpropane, glycerol, pentaerythritol, dipentaerythritol, 1,3-butanediol, 1,4-butanediol, and 1,6-hexanediol are exemplified.

The hydroxyl group-containing polyether, which is one of the hydroxyl group-containing organic compounds, is a compound that can be obtained by adding one or more alkylene oxides to one or more polyhydric alcohols or polyhydric phenols.

Examples of polyhydric alcohols to be used therein include ethylene glycol, propylene glycol, neopentyl glycol, trimethylolpropane, glycerol, pentaerythritol, dipentaerythritol, 1,3-butanediol, 1,4-butanediol, and 1,6-hexanediol. Examples of polyhydric phenols include bisphenol A, bisphenol F, phenol-novolak resin, and cresol-novolak resin. Examples of alkylene oxides include butylene oxide, propylene oxide, and ethylene oxide.

The hydroxyl group-containing polyester, which is one of the hydroxyl group-containing organic compounds, is a hydroxyl group-containing polyester that can be obtained by the esterification reaction of one or more polyhydric alcohols or polyhydric phenols with one or more monobasic acids or polybasic acids, or a hydroxyl group-containing polyester that can be obtained by the esterification reaction of one or more polyhydric alcohols or polyhydric phenols with one or more lactones.

As the examples of polyhydric alcohols and polyhydric phenols to be used therein, the same compounds as described above can be exemplified. As the monobasic acids, e.g., formic acid, acetic acid, butyric acid and benzoic acid are exemplified. As the polybasic acids, e.g., adipic acid, terephthalic acid, and trimellitic acid are exemplified. In addition to the above, as lactones, β-propiolactone, γ-butyrolactone, and ε-caprolactone are exemplified.

The polyhydric phenol that is one of hydroxyl group-containing organic compounds is a compound containing two or more hydroxyl groups directly bonded to aromatic rings in one molecule, and the same polyhydric phenols used in obtaining the hydroxyl group-containing polyethers described above can be exemplified.

<Other Additives>

If necessary, the photo-curable composition of the invention can contain additives other than the components described above.

As other additives, for example, a polymerization inhibitor, a basic compound, a fluorine and/or silicon surfactant(s) and a solvent are exemplified.

[Polymerization Inhibitor]

It is preferred for the photo-curable composition of the invention to contain a polymerization inhibitor in view of the improvement of preservation stability.

The polymerization inhibitor is preferably added in 200 to 20,000 ppm in terms of the entire amount of the photo-curable composition of the invention.

As the polymerization inhibitors, hydroquinone, benzoquinone, p-methoxyphenol, TEMPO, TEMPOL, and Cupferron A1 are exemplified.

When the photo-curable composition of the invention is used as the ink composition for inkjet recording, it is preferred to heat the composition in the range of 40 to 80° C. to lower the viscosity and then eject the composition. The addition of the polymerization inhibitor is also preferred in the light of prevention of head clogging due to thermal polymerization.

[Basic Compound]

It is preferred for the photo-curable composition of the invention to contain a basic compound for reducing performance variation due to aging from exposure to heating.

The basic compound is preferably contained from the aspect of the improvement of preservation stability of the photo-curable composition of the invention. Known basic compounds can be used in the invention, for example, basic inorganic compounds such as inorganic salts, and basic organic compounds such as amines can be preferably used.

As preferred structure of the basic compound, a compound having a structure represented by any of the following formulae (A') to (E'), or a compound including the structure can be exemplified.

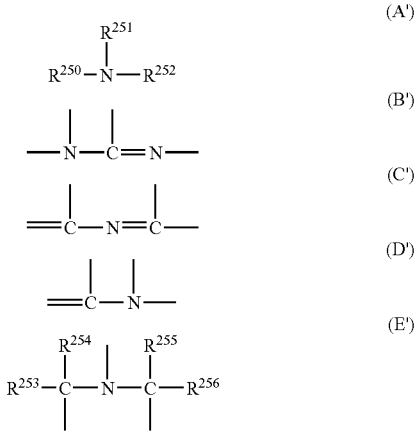

In formula (A'), each of $R^{250}$, $R^{251}$ and $R^{252}$ represents a hydrogen atom, an alkyl group having 1 to 20 carbon atoms, a cycloalkyl group having 3 to 20 carbon atoms, or an aryl group having 6 to 20 carbon atoms, and $R^{250}$ and $R^{251}$ may be bonded to each other to form a ring. These groups may each have a substituent. As the alkyl group and cycloalkyl group having a substituent, an aminoalkyl group having 1 to 20 carbon atoms, an aminocycloalkyl group having 3 to 20 carbon atoms, a hydroxyalkyl group having 1 to 20 carbon atoms, and a hydroxycycloalkyl group having 3 to 20 carbon atoms are preferred. These groups may contain an oxygen atom, a sulfur atom, or a nitrogen atom in the alkyl chain.

In formula (E'), each of $R^{253}$, $R^{254}$, $R^{255}$ and $R^{256}$ independently represents an alkyl group having 1 to 6 carbon atoms, or a cycloalkyl group having 3 to 6 carbon atoms.

As preferred basic compounds, guanidine, aminopyrrolidine, pyrazole, pyrazoline, piperazine, aminomorpholine, aminoalkylmorpholine, and piperidine can be exemplified, and they may have a substituent.

As more preferred basic compounds, a compound having an imidazole structure, a diazabicyclo structure, an onium hydroxide structure, an onium carboxylate structure, a trialkylamine structure, an aniline structure, or a pyridine structure, an alkylamine derivative having a hydroxyl group and/or an ether bond, and an aniline derivative having a hydroxyl group and/or an ether bond can be exemplified.

As the compound having an imidazole structure, imidazole, 2,4,5-triphenyl-imidazole and benzimidazole are exemplified.

As the compound having a diazabicyclo structure, 1,4-diazabicyclo[2.2.2]octane, 1,5-diazabicyclo[4.3.0]nona-5-ene, and 1,8-diazabicyclo[5.4.0]undeca-7-ene are exemplified.

As the compound having an onium hydroxide structure, triarylsulfonium hydroxide, phenacylsulfonium hydroxide, and sulfonium hydroxide having a 2-oxoalkyl group, specifically triphenylsulfonium hydroxide, tris(t-butylphenyl)sulfonium hydroxide, bis(t-butylphenyl)iodonium hydroxide, phenacylthiophenium hydroxide, and 2-oxopropylthiophenium hydroxide are exemplified.

As the compound having an onium carboxylate structure, a compound having an onium hydroxide structure in which the anion portion is replaced with carboxylate, e.g., acetate, adamantane-1-carboxylate, and perfluoroalkylcarboxylate are exemplified.

As the compound having a trialkylamine structure, tri(n-butyl)amine and tri(n-octyl)amine are exemplified.

As the compound having an aniline structure, 2,6-diisopropylaniline and N,N-dimethylaniline are exemplified.

As the alkylamine derivative having a hydroxyl group and/or an ether bond, ethanolamine, diethanolamine, triethanolamine, and tris(methoxyethoxyethyl)amine are exemplified.

As the aniline derivative having a hydroxyl group and/or an ether bond, N,N-bis(hydroxyethyl)aniline and the like are exemplified.

These basic compounds are used alone or two or more in combination.

The use amount of the basic compounds is generally 0.001 to 10 mass % based on the solids content of the photo-curable composition of the invention, and preferably 0.01 to 5 mass %. For achieving sufficient addition effect, the amount is preferably 0.001 mass % or more, and in view of sensitivity and stability, 10 mass % or less is preferred.

[Fluorine and/or Silicon Surfactants]

It is preferred for the photo-curable composition of the invention to further contain either one or two or more of fluorine and/or silicon surfactants (a fluorine surfactant and a silicon surfactant, a surfactant containing both a fluorine atom and a silicon atom).

By the addition of fluorine and/or silicon surfactants to the photo-curable composition of the invention, good sensitivity is obtained, and the adhesion of a cured product to the surface of a solid is further improved with the resolution of the cured product being excellent.

Fluorine and/or silicon surfactants are disclosed, e.g., in JP-A Nos. 62-36663, 61-226746, 61-226745, 62-170950, 63-34540, 7-230165, 8-62834, 9-54432, 9-5988, 2002-277862, U.S. Pat. Nos. 5,405,720, 5,360,692, 5,529,881, 5,296,330, 5,436,098, 5,576,143, 5,294,511, and 5,824,451. The following commercially available surfactants can also be used as they are.

The commercially available fluorine surfactants and silicon surfactants usable in the invention include, e.g., Eftop EF301, EF303 (manufactured by Shin-Akitakasei Co., Ltd.), Fluorad FC430, 431 (manufactured by Sumitomo 3M Limited), Megafac F 171, F 173, F 176, F189, R08 (manufactured by Dainippon Ink and Chemicals Inc.), Sarfron S-382, SC 101, 102, 103, 104, 105, 106 (manufactured by Asahi Glass Co., Ltd.), and Toroy Sol S-366 (manufactured by Toroy Chemical Co., Ltd.). Polysiloxane Polymer KP-341 (manufactured by Shin-Etsu Chemical Co., Ltd.) can also be used as a silicon surfactant.

In addition to the above known surfactants, surfactants comprising a polymer having a fluoro aliphatic group derived from a fluoro aliphatic compound manufactured by a telomerization method (also called a telomere method) or an oligomerization method (also called an oligomer method) can be used. The fluoro aliphatic compound can be synthesized according to a method disclosed in JP-A No. 2002-90991.

The polymer having a fluoro aliphatic group is preferably a copolymer of a monomer having a fluoro aliphatic group and at least one of (poly(oxyalkylene))acrylate and (poly(oxyalkylene))methacrylate, which copolymer may be irregularly distributed or block copolymerized.

As the poly(oxyalkylene) group, a poly(oxyethylene) group, a poly(oxypropylene) group, and a poly(oxybutylene) group are exemplified. Units comprising alkylenes having different chain lengths in the same chain length such as a poly(oxyethylene-oxypropylene-oxyethylene block unit), and a poly(oxyethylene-oxypropylene block unit) may also be used. Further, a copolymer of a monomer having a fluoro aliphatic group and (poly(oxyalkylene))acrylate (or methacrylate) may be not only a copolymer or a dimer but also a trimer or a higher copolymer obtained by copolymerization of two or more different monomers having a fluoro aliphatic group, or different two or more (poly(oxyalkylene))acrylates (or methacrylates) at the same time.

As commercially available surfactants, e.g., Megafac F-178, F-470, F-473, F-475, F-476, F-472 (manufactured by Dainippon Ink and Chemicals Inc.) can be exemplified. Further, a copolymer of acrylate (or methacrylate) having a $C_6F_{13}$ group and (poly(oxyalkylene))acrylate (or methacrylate), a copolymer of acrylate (or methacrylate) having a $C_6F_{13}$ group, (poly(oxyethylene))acrylate (or methacrylate), and (poly(oxypropylene))acrylate (or methacrylate), a copolymer of acrylate (or methacrylate) having a $C_8F_{17}$ group and (poly(oxyalkylene))acrylate (or methacrylate), and a copolymer of acrylate (or methacrylate) having a $C_8F_{17}$ group, (poly(oxyethylene))acrylate (or methacrylate), and (poly(oxypropylene))acrylate (or methacrylate) can be exemplified.

The use amount of fluorine and/or silicon surfactants is preferably 0.0001 to 5 mass % based on the total amount of the photo-curable composition of the invention, and more preferably 0.001 to 3 mass %.

[Solvent]

Organic solvents and water can be used as the solvents in the photo-curable composition of the invention. In particular, organic solvents are added for the purpose of improving an adhering property to the solid surface of a cured product (e.g., a recording medium such as paper).

[Other Components]

In addition to the above, if necessary, known compounds can be added to the photo-curable composition of the invention.

For example, for the purpose of regulating the physical properties of films, polyester resins, polyurethane resins, vinyl resins, acrylic resins, rubber resins, and waxes can be arbitrarily selectively used. Further, in order to improve an adhering property of polyolefin, PET and the like to the surface of a solid such as a recording medium, it is also preferred to contain tackifiers not hindering polymerization. Specifically, the adhesive polymers having a high molecular weight as disclosed in JP-A No. 2001-49200, pages 5-6 (e.g., a copolymer comprising an ester of (meth)acrylic acid and an alcohol having an alkyl group having 1 to 20 carbon atoms, an ester of (meth)acrylic acid and an alicyclic alcohol having 3 to 14 carbon atoms, and an ester of (meth)acrylic acid and an aromatic alcohol having 6 to 14 carbon atoms), and low molecular weight adhesive-giving resins having a polymerizable unsaturated bond are exemplified.

In the range of not hindering the advantage of the invention, if necessary, various kinds of resin additives can be used in ordinary use ranges, such as thermoplastic polymer compounds, fillers, leveling agents, defoaming agents, tackifiers, flame retardants, antioxidants, stabilizers, and the like.

Besides the radiation-curable type ink composition, the photo-curable composition of the invention can be used as image-forming materials, such as three dimensional stereolithography, holography, planographic printing plates, color proof, photoresists, and color filters, and uses of photo-curable resin materials such as coatings and adhesives. The composition of the invention can be preferably used as an alternate thioxanthone sensitizer in coating for UV-curing type white coat where whiteness is regarded as important, in particular in the use for white coat of the outer surfaces of cans.

[Ink composition]

An ink composition in the invention contains the photo-curable composition of the invention.

That is, the ink composition in the invention contains (A) a cationic polymerizable compound, (B) a sensitizing colorant represented by formula (I) (a specific sensitizing colorant), and (C) an onium salt, and if necessary, contains a colorant, a radical polymerizable compound, and a radical polymerization initiator.

These components are contained such that the specific sensitizing colorant is preferably 0.1 to 20 mass %, and more preferably 0.3 to 10 mass %, the cationic polymerizable compound is preferably 10 to 95 mass %, more preferably 30 to 93 mass %, and still more preferably 50 to 90 mass %, and when the colorant is used, the colorant is preferably 1 to 20 mass %, and more preferably 2 to 10 mass %, each based on the total mass of the photo-curable composition of the invention. It is preferred that the sum total of the components comes to 100 mass %.

The specific sensitizing colorant used in the ink composition of the invention is higher in solubility than those of generally used thioxanthone compounds and anthracene compounds and low in crystallizability, so that excellent in stability as the solution of an ink composition. Accordingly, when an ink composition containing the specific sensitizing colorant is used for inkjet recording, it is thought that excellent ejection stability can be obtained.

[Properties of Ink Composition]

Preferred physical properties of the ink composition of the invention will be described below.

When the ink composition of the invention is used for inkjet recording, considering the ejecting property, the viscosity of the composition at the temperature of the time of ejection (e.g., 25 to 80° C., and preferably 25 to 50° C.) is preferably 7 to 30 mPa·s, and more preferably 7 to 20 mPa·s. The viscosity of the ink composition of the invention at room temperature (25 to 30° C.) is, e.g., preferably 35 to 500 mPa·s, and more preferably 35 to 200 mPa·s.

The composition ratio of the ink composition of the invention is preferably arbitrarily adjusted so as to bring the viscosity into the above range. By setting the viscosity at room temperature high, penetration of ink into a recording medium can be avoided even when a porous recording medium is used, and uncured monomer can be reduced and odor can be decreased. Further, bleeding of ink at the time of spot of ink droplets can be inhibited, which leads to the improvement of image quality, and so preferred.

The surface tension of the ink composition of the invention is preferably 20 to 30 mN/m, and more preferably 23 to 28 mN/m. When recording is performed on various recording media such as polyolefin, PET, coat paper, non-coat paper and the like, from the viewpoint of bleeding and penetration, the surface tension is preferably 20 mN/m or more, and in the point of wettability, it is preferably 30 mN/m or less.

[Inkjet Recording Method]

An inkjet recording method in the invention and inkjet recorders applicable to the inkjet recording method are described below.

The inkjet recording method in the invention includes (a) ejecting the ink composition of the invention on a recording medium, and (b) irradiating the ejected ink composition with actinic radiation to cure the ink composition.

According to the inkjet recording method of the invention, by including processes (a) and (b), an image is formed with the cured ink composition on a recording medium.

Here, the peak wavelength of the actinic radiation in process (b) is preferably 200 to 600 nm, more preferably 300 to 450 nm, and still more preferably 350 to 420 nm. The output of the actinic radiation is preferably 2,000 mJ/cm$^2$ or less, more preferably 10 to 2,000 mJ/cm$^2$, still more preferably 20 to 1,000 mJ/cm$^2$, and especially preferably 50 to 800 mJ/cm$^2$.

In process (a) of the inkjet recording method of the invention, inkjet recording apparatus described in detail below can be used.

-Inkjet Recording Apparatus-

Inkjet recording apparatus for use in the inkjet recording method of the invention are not especially restricted, and known inkjet recording apparatus capable of achieving aiming resolution can be arbitrarily selected and used. That is, any of known inkjet recording apparatus including commercially available products can effect ink ejection to recording media in process (a) of the inkjet recording method of the invention.

As inkjet recording apparatus usable in the invention, e.g., apparatus having ink supply system, a temperature sensor, and an actinic radiation source are exemplified.

The ink supply system comprises primary tanks containing the ink composition of the invention, supply line, ink supply tanks immediately prior to inkjet heads, filters, and piezo type inkjet heads. The piezo type inkjet head can be driven to be capable of ejecting multi-size dots of 1 to 100 pl, and preferably 8 to 30 pl, by resolution of, e.g., 320×320 dpi to 4,000× 4,000 dpi, preferably 400×400 dpi to 1,600×1,600 dpi, and more preferably 720×720 dpi. Incidentally, "dpi" in the invention indicates the dot number per 2.54 cm.

Since it is preferred for ejected ink of radiation-curable type ink like the ink composition of the invention to be maintained at a fixed temperature, the parts from the ink supply tanks to the inkjet heads can be thermally insulated and heated. The method of temperature control is not especially restricted, but it is preferred to provide a plurality of temperature sensors at pipeline parts and control heating according to ink flow rate and environmental temperature. Temperature sensors can be installed in the vicinity of the ink supply tanks and nozzles of inkjet heads. Further, it is preferred that head units to be heated are preferably thermally shielded or insulated so that the apparatus main body is not affected by the temperature from outside air. For shortening the rise time of printer required for heating, or for reducing heat energy loss, it is preferred to make heat capacity of the whole heating unit small, as well as thermal insulation from other parts.

(b) A process of irradiating the ejected ink composition with actinic radiation to cure the ink composition will be explained below.

The ink composition ejected on a recording medium is cured by irradiation with actinic radiation.

As the actinic radiation, a mercury lamp, gas/solid state laser and the like are mainly used, and a mercury lamp and a metal halide lamp are widely known in a UV photo-curable type inkjet recording method. However, freedom from mercury is now strongly desired from the viewpoint of environmental protection, and replacement with GaN series semiconductor UV emitting device is industrially and environmentally very useful. Further, since LED (UV-LED) and LD (UV-LD) are small in size, high in duration of life and low in costs, they are expected as light sources for photo-curable type inkjet recording.

Further, it is also possible to use light emitting diode (LED) and laser diode (LD) as active radiation sources. In particular, when a UV source is necessary, UV LED and UV LD can be used. For example, violet LED having the main emission spectrum having wavelengths between 365 and 420 nm has been brought on the market by Nichia Corporation. Further, when further shorter wavelength is necessary, LED capable of emitting actinic radiation centered between 300 and 370 nm is disclosed in U.S. Pat. No. 6,084,250. Other UV-LED's are also available, and radiation in different UV bands can be irradiated. An actinic radiation source especially preferred in the invention is UV-LED, and UV-LED having peak wavelength in 340 to 370 nm is especially preferred.

Further, the maximum illuminance of the LED on recording media is preferably 10 to 2,000 mW/cm$^2$, more preferably 20 to 1,000 mW/cm$^2$, and especially preferably 50 to 800 mW/cm$^2$.

In the invention, the actinic radiations in process (b) are preferably UV rays having peak wavelengths between the range of 340 to 370 nm, and irradiated with a light emitting diode (UV-LED) generating UV rays capable of irradiation with the maximum illuminance on recording media of 10 to 2,000 mW/cm$^2$.

It is preferred for the ink composition of the invention to be irradiated with these actinic radiations for, e.g., 0.01 to 120 sec., and preferably for 0.1 to 90 sec.

Irradiation condition and fundamental irradiation method of actinic radiation are disclosed in JP-A No. 60-132767. Specifically, irradiation is performed by arranging light sources on both sides of the head units including ink ejector, and scanning the head unit and light sources with what is called a shuttle system. The irradiation of actinic radiation is to be performed after a fixed interval from spot of ink (e.g., 0.01 to 0.5 sec, preferably 0.01 to 0.3 sec, and more preferably 0.01 to 0.15 sec). By controlling the time from ink spotting to irradiation like this, it becomes possible to prevent the spotted ink from bleeding before curing. Further, since the deep portion of a porous recording medium where the light does not reach can be subjected to exposure before penetration of ink, the unreacted monomer can be prevented from remaining and, as a result, generation of odor can be reduced.

Further, curing may be terminated by a separate light source not accompanied by driving. A method of irradiation using optical fibers, and a method of applying collimated lights to a mirror provided on the side of the head unit and irradiating the UV rays to the recording part are disclosed in WO 99/54415, and such a method can also be applied to the inkjet recording method of the invention.

By adopting these inkjet recording methods, dot sizes of ink droplets spotted on various recording media different in wettability of the surfaces can be maintained constant, so that image quality is improved. Incidentally, for obtaining a color image, it is preferred to lay colors in order from those low in lightness. By laying inks in order from low in lightness, irradiation ray easily reaches down to the lower inks, therefore, good sensitivity for curing, decrease of residual monomers, reduction of odor, and the improvement of adhesion can be expected. Although irradiation can be done collectively after ejection of all colors, it is preferred to perform exposure at every color from the viewpoint of acceleration of curing.

Thus, by curing the ink composition of the invention in high sensitivity by means of irradiation with actinic radiation, a high-definition and strong image can be formed on the surface of a recording medium. Further, an image excellent in adhesion to a recording medium can be formed.

In addition, the ink composition of the invention is high in preservation stability, and when applied to an inkjet apparatus, the vicinities of inkjet heads are free from generation of precipitation of the components, and the ink composition is excellent in ejection stability, so that a stable image can be formed.

The exemplary embodiments according to the invention are described below.

<1> A photo-curable composition comprising:

(A) a cationic polymerizable compound, (B) a sensitizing colorant represented by the following formula (I), and (C) an onium salt:

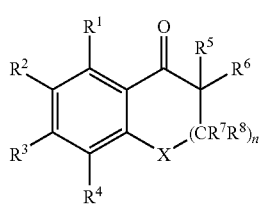

(I)

wherein, in the formula (I), X represents O, S or NR; R represents a hydrogen atom, an alkyl group, or an acyl group; n represents 0 or 1; each of $R^1$, $R^2$, $R^3$, $R^4$, $R^5$, $R^6$, $R^7$, and $R^8$ independently represents a hydrogen atom, or a monovalent substituent, contiguous two of $R^1$, $R^2$, $R^3$ and $R^4$ may be linked to each other to form a ring, and $R^5$ or $R^6$ and $R^7$ or $R^8$ may be linked to each other to form an aliphatic ring, but they do not form an aromatic ring.

<2> The photo-curable composition according to <1>, wherein the onium salt is selected from the group consisting of the following formulae (C1) to (C5):

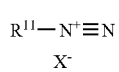

(C1)

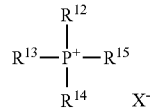

(C2)

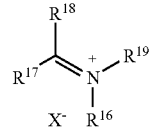

(C3)

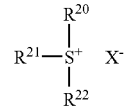

(C4)

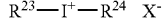

(C5)

wherein, in the formulae (C1) to (C5), $R^{11}$ represents an aryl group; each of $R^{12}$, $R^{13}$, $R^{14}$, $R^{15}$, and $R^{16}$ independently represents an alkyl group, an alkenyl group, an alkynyl group, an aryl group, a hydrocarbocyclic group, a heterocyclic group, an alkoxy group, or an aryloxy group; each of $R^{17}$, $R^{18}$ and $R^{19}$ independently represents a hydrogen atom, a halogen atom, or a monovalent organic group; each of $R^{20}$, $R^{21}$ and $R^{22}$ independently represents a monovalent organic group; each of $R^{23}$ and $R^{24}$ independently represents an aryl group, an alkyl group, or a cycloalkyl group; and $X^-$ represents a non-nucleophilic anion.

<3> The photo-curable composition according to <2>, wherein onium salt (C) is a compound represented by formula (C5).

<4> The photo-curable composition according to any one of <1> to <3>, which further contains (D) a colorant.

<5> An ink composition containing the photo-curable composition according to any one of <1> to <4>.

<6> An inkjet recording method comprising:

(a) ejecting the ink composition according to <5> on a recording medium, and (b) irradiating the ejected ink composition with actinic radiation to cure the ink composition.

<7> The inkjet recording method according to <6>, wherein the actinic radiation is ultraviolet rays emitted from a light emitting diode emitting ultraviolet rays having a light emission peak in the range of 340 to 370 nm, and a maximum intensity of illumination on the surface of a recording medium is 10 to 2,000 mW/cm².

EXAMPLES

The present invention will be described more detail with reference to examples, but the invention is by no means restricted thereto. The examples relate to the ink for a UV inkjet recording of respective colors. In the examples, "parts" means "mass parts" unless otherwise indicated.

<<Preparation of Pigment Dispersion>>

In the first place, pigment dispersions 1 of yellow, magenta, cyan, black and white, respectively, were prepared according to the following methods.

Each dispersing condition was arbitrarily regulated with a known disperser so as to obtain the average particle size of each pigment particles of the range of 0.2 to 0.3 μm, and then dispersed particles were filtered with a filter under heating to obtain each pigment dispersion 1.

| (Yellow pigment dispersion 1) | |
|---|---|
| C.I. Pigment Yellow 13 | 20 mass parts |
| Polymer dispersant (Solsperse series, manufactured by Zeneca) | 20 mass parts |
| OXT-221 (manufactured by TOAGOSEI CO., LID) | 60 mass parts |

| (Magenta pigment dispersion 1) | |
|---|---|
| C.I. Pigment Red 57:1 | 20 mass parts |
| Polymer dispersant (Solsperse series, manufactured by Zeneca) | 20 mass parts |
| OXT-221 (manufactured by TOAGOSEI CO., LTD) | 60 mass parts |

| (Cyan pigment dispersion 1) | |
|---|---|
| C.I. Pigment Blue 15:3 | 20 mass parts |
| Polymer dispersant (Solsperse series, manufactured by Zeneca) | 20 mass parts |
| OXT-221 (manufactured by TOAGOSEI CO., LTD) | 60 mass parts |

| (Black pigment dispersion 1) | |
|---|---|
| C.I. Pigment Black 7 | 20 mass parts |
| Polymer dispersant (Solsperse series, manufactured by Zeneca) | 20 mass parts |
| OXT-221 (manufactured by TOAGOSEI CO., LTD) | 60 mass parts |

| (White pigment dispersion 1) | |
|---|---|
| Titanium oxide (average particle size: 0.15 μm, refractive index: 2.52) | 25 mass parts |
| Neutral polymer dispersant PB822 (manufactured by Ajinomoto Fine-Techno Co., Ltd.) | 14 mass parts |
| OXT-221 (manufactured by TOAGOSEI CO., LTD) | 60 mass parts |

Example 1

<<Preparation of Ink>>

Ink composition of each color was obtained with each of the above-obtained pigment dispersion 1 by blending the following components.

| (Yellow ink 1) | |
|---|---|
| Yellow pigment dispersion 1 | 5 mass parts |
| Onium salt (Irgacure 250, having the following structure, manufactured by Ciba Specialty Chemicals Inc.) | 6 mass parts |
| Specific sensitizing colorant (I-14, having the following structure) | 3 mass parts |
| Cationic polymerizable compound | |
| Monomer: 3,4-epoxycyclohexylmethyl-3',4'-epoxycyclohexane carboxylate (Celloxide 2021A, manufactured by Daicel UCB Co., Ltd.) | 40 mass parts |
| Monomer: 3,7-bis(3-oxetanyl)-5-oxanonane (OXT-221, manufactured by TOAGOSEI CO., LTD) | 45 mass parts |
| Surfactant (BYK 307, manufactured by BYK Chemie) | 1 mass part |

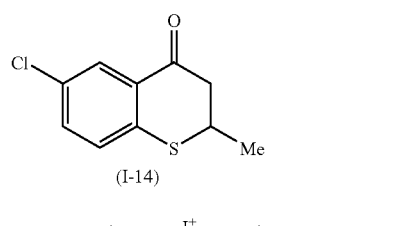

(I-14)

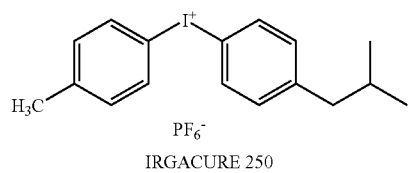

IRGACURE 250

| (Magenta ink 1) | |
|---|---|
| Magenta pigment dispersion 1 | 5 mass parts |
| Onium salt (Irgacure 250, having the above structure, manufactured by Ciba Specialty Chemicals Inc.) | 6 mass parts |
| Specific sensitizing colorant (I-14, having the above structure) | 3 mass parts |
| Cationic polymerizable compound | |
| Monomer: 3,4-epoxycyclohexylmethyl-3',4'-epoxycyclohexane carboxylate (Celloxide 2021A, manufactured by Daicel UCB Co., Ltd.) | 40 mass parts |
| Monomer: 3,7-bis(3-oxetanyl)-5-oxanonane (OXT-221, manufactured by TOAGOSEI CO., LTD) | 45 mass parts |
| Surfactant (BYK 307, manufactured by BYK Chemie) | 1 mass part |

| (Cyan ink 1) | |
|---|---|
| Cyan pigment dispersion 1 | 5 mass parts |
| Onium salt (Irgacure 250, having the above structure, manufactured by Ciba Specialty Chemicals Inc.) | 6 mass parts |
| Specific sensitizing colorant (I-14, having the above structure) | 3 mass parts |
| Cationic polymerizable compound | |
| Monomer: 3,4-epoxycyclohexylmethyl-3',4'-epoxycyclohexane carboxylate (Celloxide 2021A, manufactured by Daicel UCB Co., Ltd.) | 40 mass parts |
| Monomer: 3,7-bis(3-oxetanyl)-5-oxanonane (OXT-221, manufactured by TOAGOSEI CO., LTD) | 45 mass parts |
| Surfactant (BYK 307, manufactured by BYK Chemie) | 1 mass part |

| (Black ink 1) | |
|---|---|
| Black pigment dispersion 1 | 5 mass parts |
| Onium salt (Irgacure 250, having the above structure, manufactured by Ciba Specialty Chemicals Inc.) | 6 mass parts |
| Specific sensitizing colorant (I-14, having the above structure) | 3 mass parts |
| Cationic polymerizable compound | |
| Monomer: 3,4-epoxycyclohexylmethyl-3',4'-epoxycyclohexane carboxylate (Celloxide 2021A, manufactured by Daicel UCB Co., Ltd.) | 40 mass parts |
| Monomer: 3,7-bis(3-oxetanyl)-5-oxanonane (OXT-221, manufactured by TOAGOSEI CO., LTD) | 45 mass parts |
| Surfactant (BYK 307, manufactured by BYK Chemie) | 1 mass part |

| (White ink 1) | |
|---|---|
| White pigment dispersion 1 | 5 mass parts |
| Onium salt (Irgacure 250, having the above structure, manufactured by Ciba Specialty Chemicals Inc.) | 6 mass parts |
| Specific sensitizing colorant (I-14, having the above structure) | 3 mass parts |
| Cationic polymerizable compound | |
| Monomer: 3,4-epoxycyclohexylmethyl-3',4'-epoxycyclohexane carboxylate (Celloxide 2021A, manufactured by Daicel UCB Co., Ltd.) | 40 mass parts |
| Monomer: 3,7-bis(3-oxetanyl)-5-oxanonane (OXT-221, manufactured by TOAGOSEI CO., LTD) | 45 mass parts |
| Surfactant (BYK 307, manufactured by BYK Chemie) | 1 mass part |

Ink 1 of each color prepared above was filtered through a filter having absolute filtering accuracy of 2 μm to obtain ink 1 of each color.

<<Inkjet Image Recording>>

Next, recording was performed on a recording medium with a commercially available inkjet recording apparatus having piezo inkjet nozzles. An ink supply system comprises primary tanks, a supply line, ink supply tanks immediately prior to inkjet heads, filters, and piezo inkjet heads. The parts from the ink supply tanks to the inkjet heads were thermally insulated and heated. Temperature sensors were installed near the ink supply tanks and the nozzles of inkjet heads, and the temperature was controlled to maintain a temperature of 70° C.±2° C. at the nozzle parts. The piezo inkjet head was driven to eject multi-size dots of 8 to 30 pl with a resolution of 720×720 dpi. After the spot of ink droplets, UV rays were converged on the exposure surface at an illuminance of 100 mW/cm², and an exposure system, a fast scanning rate and an ejection frequency were adjusted so as to initiate irradiation 0.1 second after the spot of ink droplets on the recording medium. The exposure time was made a variable and radiation of exposure energy was performed. Incidentally, "dpi" in the invention indicates the dot number per 2.54 cm.

The prepared ink 1 of each color was ejected in the order of black, cyan, magenta, yellow and white at an ambient temperature of 25° C. After ejection of each color, UV rays were irradiated on each respective color with a metal halide lamp Vzero 085 (manufactured by Integration Technology). Exposure was performed with an uniform exposure energy totaling 50 mJ/cm² per one color to completely cure the ink such that it does not feel tacky when examined by touch.

As the recording media, a surface grained aluminum support, a transparent biaxially stretched polypropylene film having been subjected to surface treatment to acquire printing suitability, a soft vinyl chloride sheet, cast coat paper, and commercially available recycled paper were used. When a color image was recorded on each medium, every obtained image was free from dot bleeding and exhibited high resolution. Further, even when high quality paper was used as a recording medium, ink does not strike through, ink was sufficiently cured, and odor due to unreacted monomers was hardly present. Ink recorded on a film had sufficient flexibility, cracks were not generated in the ink by bending the film, and no problems were present in an adhesion test performed by applying and peeling off CELLOTAPE (registered trademark).

Examples 2 to 10 and Comparative Examples 1 to 7

<<Preparation of Ink>>

White inks 2 to 17 were prepared according to the following methods.

Example 2

White Ink 2

White ink 2 was prepared in the same manner as in the preparation of white ink 1 except for using (I-17) having the following structure as the specific sensitizing colorant in place of (I-14).

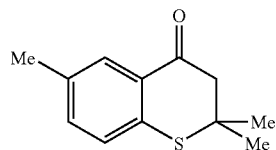

(I-17)

Example 3

White Ink 3

White ink 3 was prepared in the same manner as in the preparation of white ink 1 except for using iodonium salt A having the following structure as the onium salt in place of Irgacure 250.

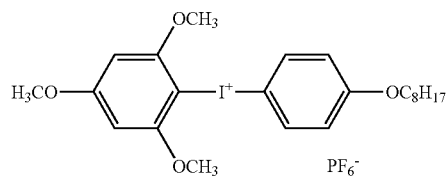

Iodonium Salt A

Example 4

White Ink 4

White ink 4 was prepared in the same manner as in the preparation of white ink 1 except for using PHOTOINITIATOR 2074 (manufactured by RHODIA) having the following structure as the onium salt in place of Irgacure 250.

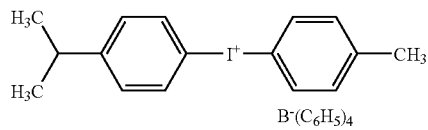

PHOTOINITIATOR 2074

Example 5

White Ink 5

White ink 5 was prepared in the same manner as in the preparation of white ink 1 except for using sulfonium salt B having the following structure as the onium salt in place of Irgacure 250.

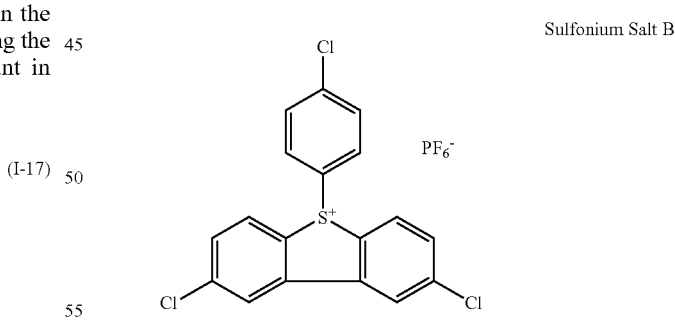

Sulfonium Salt B

Example 6

White Ink 6

White ink 6 was prepared in the same manner as in the preparation of white ink 1 except for using phosphonium salt C having the following structure as the onium salt in place of Irgacure 250.

Phosphonium Salt C

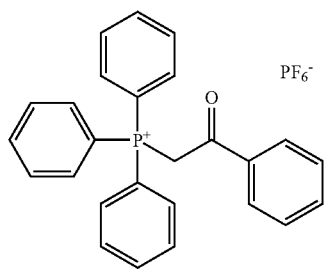

Example 7

White Ink 7

White ink 7 was prepared in the same manner as in the preparation of white ink 1 except for using pyridinium salt D having the following structure as the onium salt in place of Irgacure 250.

Pyridinium Salt D

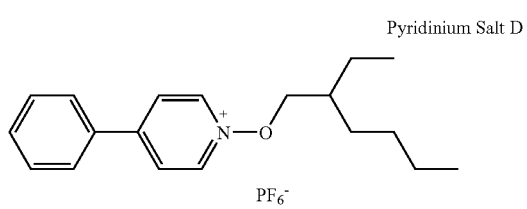

Example 8

White Ink 8

White ink 8 was prepared in the same manner as in the preparation of white ink 1 except for using thiazolium salt E having the following structure as the onium salt in place of Irgacure 250.

Thiazolium Salt E

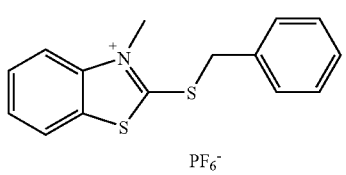

Example 9

White Ink 9

White ink 9 was prepared in the same manner as in the preparation of white ink 1 except for using diazonium salt F having the following structure as the onium salt in place of Irgacure 250.

Diazonium Salt F

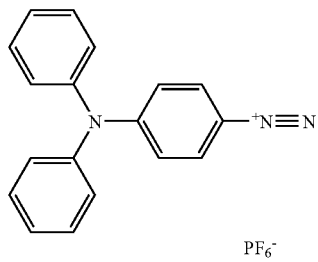

Example 10

White Ink 10

White ink 10 was prepared with the above white pigment dispersion 1 by blending the following components.

| (White ink 10) | |
|---|---|
| White pigment dispersion 1 | 5 mass parts |
| Onium salt: Irgacure 250 (having the above structure, manufactured by Ciba Specialty Chemicals Inc.) | 6 mass parts |
| Specific sensitizing colorant (I-14, having the above structure) | 3 mass parts |
| Cationic polymerizable compound Monomer: 3,4-epoxycyclohexylmethyl-3',4'-epoxycyclohexane carboxylate (Celloxide 2021A, manufactured by Daicel UCB Co., Ltd.) | 30 mass parts |
| Monomer: 3,7-bis(3-oxetanyl)-5-oxanonane (OXT-221, manufactured by TOAGOSEI CO., LTD) | 45 mass parts |
| Surfactant (BYK 307, manufactured by BYK Chemie) | 1 mass part |
| Radical polymerizable compound: 1,6-hexanediol diacrylate | 10 mass parts |

Comparative Example 1

White Ink 11

White ink 11 was prepared with the above white pigment dispersion 1 by blending the following components.

| (White ink 11) | |
|---|---|
| White pigment dispersion 1 | 5 mass parts |
| Onium salt: Irgacure 250 (having the above structure, manufactured by Ciba Specialty Chemicals Inc.) | 6 mass parts |
| Sensitizing colorant (Darocur ITX, having the following structure, manufactured by Ciba Specialty Chemicals Inc.) | 3 mass parts |
| Cationic polymerizable compound | |
| Monomer: 3,4-epoxycyclohexylmethyl-3',4'-epoxycyclohexane carboxylate (Celloxide 2021A, manufactured by Daicel UCB Co., Ltd.) | 40 mass parts |
| Monomer: 3,7-bis(3-oxetanyl)-5-oxanonane (OXT-221, manufactured by TOAGOSEI CO., LTD) | 45 mass parts |
| Surfactant (BYK 307, manufactured by BYK Chemie) | 1 mass part |

-continued

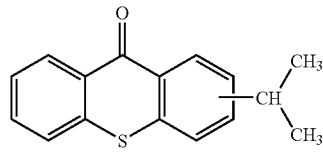

Darocur ITX
Mixture of 2-isopropylthioxanthone
and 4-isopropylthioxanthone

Comparative Example 2

White Ink 12

White ink 12 was prepared in the same manner as in the preparation of white ink 11 except for using sulfonium salt B as the onium salt in place of Irgacure 250.

Comparative Example 3

White Ink 13

White ink 13 was prepared in the same manner as in the preparation of white ink 11 except for using 9,10-dibutoxy-anthracene (manufactured by Kawasaki Kasei Chemicals Ltd.) as the sensitizing colorant in place of Darocur ITX.

Comparative Example 4

White Ink 14

White ink 14 was prepared in the same manner as in the preparation of white ink 11 except for using phosphonium salt C having the above structure as the onium salt in place of Irgacure 250.

Comparative Example 5

White Ink 15

White ink 15 was prepared in the same manner as in the preparation of white ink 11 except for using pyridinium salt D having the above structure as the onium salt in place of Irgacure 250.

Comparative Example 6

White Ink 16

White ink 16 was prepared in the same manner as in the preparation of white ink 11 except for using thiazolium salt E having the above structure as the onium salt in place of Irgacure 250.

Comparative Example 7

White Ink 17

White ink 17 was prepared in the same manner as in the preparation of white ink 11 except for using diazonium salt F having the above structure as the onium salt in place of Irgacure 250.

Crude white inks 2 to 17 prepared above were filtered through a filter having absolute filtering accuracy of 2 μm to obtain white inks 2 to 17 respectively.

<<Inkjet Image Recording>>

White images alone were formed with white inks 1 to 17 prepared above in the same manner as in Example 1.

Example 11

A white image was formed in the same manner as in Example 1 with the above white ink 1 except that a purple light-emitting diode UV-LED was used in place of a metal halide lamp Vzero 085 (manufactured by Integration Technology).

In the example, NCCU033 (manufactured by Nichia Corporation) is used as a UV-LED. This LED outputs UV rays of wavelength 365 nm from 1 chip, and about 100 mW of light is emitted from the chip by supplying a current of about 500 mA thereto. By arraying a plurality of the chips at intervals of 7 mm, power of 0.3 W/cm$^2$ can be obtained at the surface of a recording medium (hereinafter also referred to as "media"). A time after ejection and before exposure of ink, and a time of exposure may be varied by varying the transfer rate of the media and the distance in a conveyance direction between the head and the LED. In Example 11, the ink is exposed about 0.5 seconds after spotting.

The exposure energy applied to the media can be adjusted to between 0.01 J/cm$^2$ and 15 J/cm$^2$ by setting of the distance to the media and transfer rate accordingly.

Comparative Example 8

A white image was formed in the same manner as in Example 11 with the above white ink 11.

<<Evaluation of Inkjet Image>>

Evaluations of sensitivity necessary to curing, adhesion, ink bleeding, and coloring property of each of the formed images were carried out according to the following methods.

Further, ejection stability of prepared white inks 1 to 17 were evaluated according to the following methods.

1. Measurement of Sensitivity for Curing

High quality paper was put on a printed sample immediately after exposure, and transfer of the colorant to the high quality paper when a pressure roller (50 kg/cm$^2$) was rolled on the sample was evaluated. An exposure energy quantity (mJ/cm$^2$) at which no transfer is exhibited is defined as the sensitivity for curing. The smaller the numerical value, the higher the sensitivity.

2. Evaluation of Adhesion on Surface-Grained Aluminum Support

As for the formed images, samples completely free from scratches on the printed surface, and samples having on the printed surfaces thereof 11 vertical and 11 horizontal scratches at intervals of 1 mm such that 100 squares each of 1 mm×1 mm are formed, were prepared in accordance with JIS K500. A piece of CELLOTAPE (registered trademark) was adhered to each printed surface and swiftly peeled off at an angle of 90°. The printed image that remains in an unpeeled state, and the state of the square are evaluated in accordance with the following criteria.

A: Peeling of the printed image is not observed at all even in the test squares.

B: Peeling of the image is observed in the test squares, but the image is not significantly peeled if the printed surface thereof is not scratched.

C: Ready peeling by CELLOTAPE is observed both with the image free from scratches and the image in the test squares.

3. Evaluation of Bleeding of Ink on Surface-Grained Aluminum Support

Bleeding of ink of the image printed on a surface-grained aluminum support was evaluated in accordance with the following criteria.

A: Bleeding is not observed between contiguous dots.

B: A small amount of bleeding is observed between contiguous dots.

C: A large amount of bleeding is observed between contiguous dots such that the image is obviously blurred.

4. Evaluation of Coloring Properties

White ink was printed on a PET substrate, and the substrate was placed on a white mount. The optical density of yellow was measured with a densitometer, X-Rite 310 (trade name, manufactured by X-Rite), to evaluate the coloring properties of the ink in accordance with the following criteria. The lower the optical density of yellow is, the lower the degree of yellow coloring is, which is indicative of superior whiteness.

A: The value of the optical density of yellow is smaller than 0.15.

C: The value of the optical density of yellow is 0.15 or larger.

5. Evaluation of Ejection Stability

The obtained ink composition was preserved at room temperature for two weeks, and then recording on a recording medium was performed with a commercially available inkjet recorder having piezo inkjet nozzles. Non-recording of dots and the presence of splashing of ink after continuous printing for 24 hours at room temperature were visually observed and evaluated in accordance with the following criteria.

A: Non-recording of dots or ink splashing occurs 0 to 5 times.

B: Non-recording of dots or ink splashing occurs 6 to 20 times.

C: Non-recording dots or ink splashing occurs 21 times or more.

The results of the above evaluations are shown collectively in Table 2 below.

TABLE 2

| Example No. | Ink No. | Sensitivity for Curing (mJ/cm$^2$) | Adhesion | Bleeding of Ink | Coloring Property | Ejection Stability |
| --- | --- | --- | --- | --- | --- | --- |
| Example 1 | White ink 1 | 60 | A | A | A | A |
| Example 2 | White ink 2 | 60 | A | A | A | A |
| Example 3 | White ink 3 | 60 | A | A | A | A |
| Example 4 | White ink 4 | 60 | A | A | A | A |
| Example 5 | White ink 5 | 100 | A | A | A | A |
| Example 6 | White ink 6 | 400 | B | B | A | A |
| Example 7 | White ink 7 | 300 | B | B | A | A |
| Example 8 | White ink 8 | 300 | B | B | A | A |
| Example 9 | White ink 9 | 300 | B | B | A | A |
| Example 10 | White ink 10 | 60 | A | A | A | A |
| Example 11 | White ink 1 | 60 | A | A | A | A |
| Comparative Example 1 | White ink 11 | 120 | B | B | C | C |
| Comparative Example 2 | White ink 12 | 150 | B | B | C | B |
| Comparative Example 3 | White ink 13 | 90 | B | A | C | B |
| Comparative Example 4 | White ink 14 | 500 | B | B | C | C |
| Comparative Example 5 | White ink 15 | 400 | B | B | C | C |
| Comparative Example 6 | White ink 16 | 400 | B | B | C | C |
| Comparative Example 7 | White ink 17 | 400 | B | B | C | C |
| Comparative Example 8 | White ink 11 | 150 | B | B | C | C |

As is apparently seen in Table 2, all of white inks in the examples of the invention are high in sensitivity for curing and excellent in ejection stability. Further, coloring is not observed in the images obtained with white inks in the examples of the invention, excellent in adhesion to the recording medium (the surface of the solid), and free from bleeding of ink.

The invention can provide photo-curable compositions capable of forming a cured film free from coloration due to a sensitizer, showing high sensitivity to irradiation with actinic radiation, and high in adhesion to the surface of a solid.

The invention can further provide an ink composition showing high sensitivity to irradiation with actinic radiation, excellent in color reproducibility, and capable of forming an image having high adhesion to a recording medium. The invention can further provide an inkjet recording method using the ink composition.

What is claimed is:

1. A photo-curable composition comprising:
   (A) a cationic polymerizable compound,
   (B) a sensitizing colorant represented by the following formula (I), and
   (C) an onium salt:

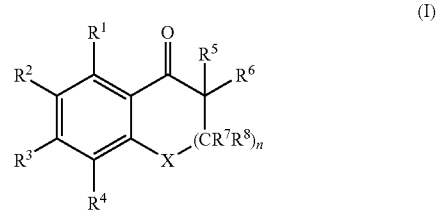

wherein, in the formula (I), X represents O, S or NR; R represents a hydrogen atom, an alkyl group, or an acyl group; n represents 0 or 1; each of $R^1$, $R^2$, $R^3$, $R^4$, $R^5$, $R^6$, $R^7$, and $R^8$ independently represents a hydrogen atom, or a monovalent substituent, contiguous two of $R^1$, $R^2$, $R^3$ and $R^4$ may be linked to each other to form a ring, and $R^5$ or $R^6$ and $R^7$ or $R^8$ may be linked to each other to form an aliphatic ring, but they do not form an aromatic ring.

2. The photo-curable composition according to claim 1, wherein the onium salt is selected from the group consisting of the following formulae (C1) to (C5):

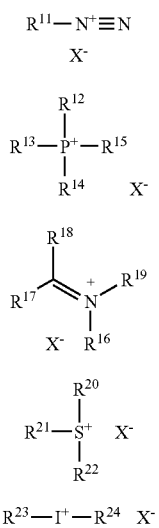

wherein, in the formulae (C1) to (C5), $R^{11}$ represents an aryl group; each of $R^{12}$, $R^{13}$, $R^{14}$, $R^{15}$, and $R^{16}$ independently represents an alkyl group, an alkenyl group, an alkynyl group, an aryl group, a hydrocarbocyclic group, a heterocyclic group, an alkoxy group, or an aryloxy group; each of $R^{17}$, $R^{18}$ and $R^{19}$ independently represents a hydrogen atom, a halogen atom, or a monovalent organic group; each of $R^{20}$, $R^{21}$ and $R^{22}$ independently represents a monovalent organic group; each of $R^{23}$ and $R^{24}$ independently represents an aryl group, an alkyl group, or a cycloalkyl group; and $X^-$ represents a non-nucleophilic anion.

3. The photo-curable composition according to claim 2, wherein onium salt (C) is a compound represented by formula (C5).

4. The photo-curable composition according to claim 1, which further contains (D) a colorant.

5. An ink composition containing the photo-curable composition according to claim 1.

6. An inkjet recording method comprising:
 (a) ejecting the ink composition according to claim 5 on a recording medium, and
 (b) irradiating the ejected ink composition with actinic radiation to cure the ink composition.

7. The inkjet recording method according to claim 6, wherein the actinic radiation is ultraviolet rays emitted from a light emitting diode emitting ultraviolet rays having a light emission peak in the range of 340 to 370 nm, and a maximum intensity of illumination on the surface of a recording medium is 10 to 2,000 mW/cm².

* * * * *